United States Patent
Zhang et al.

(10) Patent No.: US 10,781,207 B2
(45) Date of Patent: Sep. 22, 2020

(54) INHIBITORS OF MUTANT ISOCITRATE DEHYDROGENASES AND COMPOSITIONS AND METHODS THEREOF

(71) Applicant: IsoCure Biosciences Inc., Dover, DE (US)

(72) Inventors: Tinghu Zhang, Brookline, MA (US); Jianwei Che, San Diego, CA (US)

(73) Assignee: IsoCure Biosciences Inc., Dover, DE (US)

( * ) Notice: Subject to any disclaimer, the term of this patent is extended or adjusted under 35 U.S.C. 154(b) by 0 days.

(21) Appl. No.: 16/339,502

(22) PCT Filed: Oct. 10, 2017

(86) PCT No.: PCT/US2017/055910
§ 371 (c)(1),
(2) Date: Apr. 4, 2019

(87) PCT Pub. No.: WO2018/071404
PCT Pub. Date: Apr. 19, 2018

(65) Prior Publication Data
US 2019/0233414 A1 Aug. 1, 2019

Related U.S. Application Data

(60) Provisional application No. 62/406,622, filed on Oct. 11, 2016, provisional application No. 62/466,453, filed on Mar. 3, 2017.

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
None
See application file for complete search history.

(56) References Cited

U.S. PATENT DOCUMENTS 7,943,617 B2 * 5/2011 Dhar .................... C07D 487/04
514/249
2008/0275052 A1 * 11/2008 Dhar .................... C07D 487/04
514/249

OTHER PUBLICATIONS

Okoye-Okafor et al, Nature Chemical Biology, 11(11), pp. 878-886 (Year: 2015).*

* cited by examiner

*Primary Examiner* — Zinna Northington Davis
(74) *Attorney, Agent, or Firm* — Milstein Zhang & Wu LLC

(57) ABSTRACT

The invention provides novel chemical compounds useful for treating cancer, or a related disease or disorder thereof, and pharmaceutical composition and methods of preparation and use thereof.

7 Claims, 6 Drawing Sheets

A

B

SEGGFIWAC*K

INHIBITORS OF MUTANT ISOCITRATE DEHYDROGENASES AND COMPOSITIONS AND METHODS THEREOF

PRIORITY CLAIMS AND RELATED PATENT APPLICATIONS

This application is the US national phase and claims priority to PCT/US17/55910, filed Oct. 10, 2017, which claims the benefit of priority to U.S. Provisional Application Ser. No. 62/406,622, filed on Oct. 11, 2016, and 62/466,453, filed Mar. 3, 2017, the entire content of each of which is incorporated herein by reference in its entirety.

TECHNICAL FIELDS OF THE INVENTION

The invention generally relates to therapeutics and treatment methods for certain diseases and conditions. More particularly, the invention provides novel chemical compounds and pharmaceutical compositions thereof useful for treating cancer and methods of preparation and use thereof.

BACKGROUND OF THE INVENTION

Isocitrate dehydrogenase (IDH) is an enzyme that catalyzes the oxidative decarboxylation of isocitrate, producing alpha-ketoglutarate (α-ketoglutarate) and $CO_2$. IDH exists in three isoforms in humans: IDH3 catalyzes the third step of the citric acid cycle while converting NAD+ to NADH in the mitochondria. The isoforms IDH1 and IDH2 catalyze the same reaction outside the context of the citric acid cycle and use NADP+ as a cofactor instead of NAD+. IDHs localize to the cytosol as well as the mitochondrion and peroxisome.

Normal, wild type IDH enzymes help to break down nutrients and generate energy for cells. When mutated, IDH creates a molecule that alters the cells' genetic programming, and instead of maturing, the cells remain primitive and proliferate quickly. Non-mutant IDH 1/2 catalyzes the oxidative decarboxylation of isocitrate to a-ketoglutarate (a-KG) thereby reducing NAD+ (NADP+) to NADP (NADPH), e.g., in the forward reaction.

IDH1 and IDH2 are mutated in a wide range of hematologic and solid tumor malignancies. Mutations of IDH 1/2 present in certain cancer cells result in a new ability of the enzyme to catalyze the NAPH-dependent reduction of -ketoglutarate to R (-)-2-hydroxyglutarate (2 HG), which is not formed by wild-type IDH 1/2. Human IDH2 gene encodes a protein of 452 amino acids. (GenBank entries NM_002168.2 and NP_002159.2; The MGC Project Team 2004, *Genome Res.* 14:2121-2127). Human IDH1 gene encodes a protein of 414 amino acids (GenBank entries NM_005896.2 and NP_005887.2; Nekrutenko et al, 1998 *Mol. Biol. Evol.* 15:1674-1684; Geisbrecht et al, 1999 *J. Biol. Chem.* 274:30527-30533; Wiemann et al, 2001 *Genome Res.* 11:422-435; The MGC Project Team 2004 *Genome Res.* 14:2121-2127; Sjoeblom et al. 2006 *Science* 314:268-274.) 2 HG production is believed to contribute to the formation and progression of cancer. (Dang, et al. 2009 *Nature* 462:739-44.)

There is an urgent and growing need for improved cancer therapeutics and treatment methods, e.g., via effective inhibition of mutant IDH 1/2 and their alpha hydroxyl neoactivity.

SUMMARY OF THE INVENTION

The invention provides novel, orally available, selective and potent inhibitors of mutated IDH 1 and/or IDH 2 proteins. The compounds disclosed herein form irreversible covalent bond or reversible binding interactions with mutant IDH 1 and/or IDH 2 protein and effectively inhibit their respective alpha hydroxyl neoactivity.

In one aspect, the invention generally relates to a compound having the structural formula of (I):

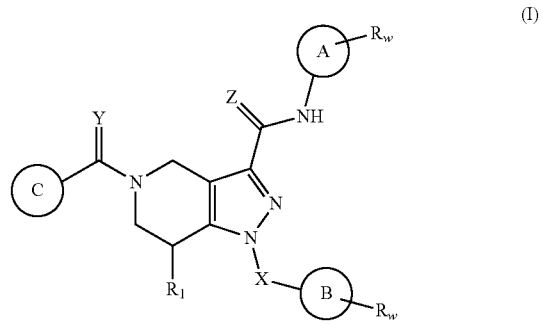

wherein,
each of Ring A, Ring B and Ring C is independently a 5- or 6-membered cyclic or bicyclic alkyl, heteroalkyl, aryl, or heteroaryl ring;
each $R_W$ is independently a hydrogen, a halide, OH, $NH_2$, alkyl, alkyl amine, alkyl amide, alkoxy, or an electrophilic group $R_E$;
$R_1$ is H or a $C_1$-$C_3$ alkyl group;
X is $CH_2$, NH, O, S or a single bond;
Y is $CH_2$, NH, O or S; and
Z is $CH_2$, NH, O or S.

In another aspect, the invention generally relates to a pharmaceutical composition comprising a compound having the structural formula of (I):

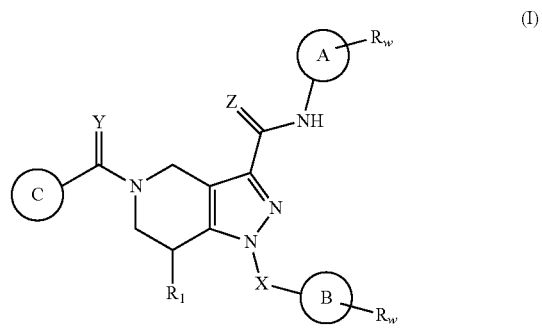

wherein,
each of Ring A, Ring B and Ring C is independently a 5- or 6-membered cyclic or bicyclic alkyl, heteroalkyl, aryl, or heteroaryl ring;
each $R_W$ is independently a hydrogen, a halide, OH, $NH_2$, alkyl, alkyl amine, alkyl amide, alkoxy, or an electrophilic group $R_E$;
$R_1$ is H or a $C_1$-$C_3$ alkyl group;
X is $CH_2$, NH, O, S or a single bond;
Y is $CH_2$, NH, O or S; and
Z is $CH_2$, NH, O or S,
or a pharmaceutically acceptable form thereof, effective to treat, prevent, or reduce one or more cancers, or a related disease or disorder thereof, in a mammal, including a human, and a pharmaceutically acceptable excipient, carrier, or diluent.

In yet another aspect, the invention generally relates to a pharmaceutical composition comprising a compound disclosed herein.

In yet another aspect, the invention generally relates to a unit dosage form comprising a pharmaceutical composition disclosed herein.

In yet another aspect, the invention generally relates to a method for treating, reducing, or preventing a disease or disorder, comprising administering to a subject in need thereof a pharmaceutical composition comprising a compound having the structural formula of (I):

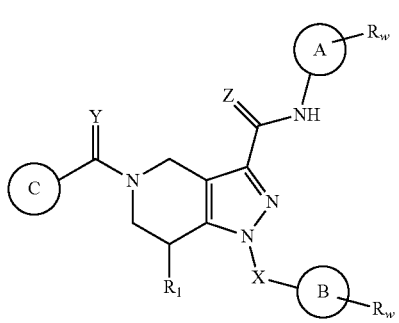

(I)

wherein,
each of Ring A, Ring B and Ring C is independently a 5- or 6-membered cyclic or bicyclic alkyl, heteroalkyl, aryl, or heteroaryl ring;
each $R_W$ is independently a hydrogen, a halide, OH, $NH_2$, alkyl, alkyl amine, alkyl amide, alkoxy, or an electrophilic group $R_E$;
$R_1$ is H or a $C_1$-$C_3$ alkyl group;
X is $CH_2$, NH, O, S or a single bond;
Y is $CH_2$, NH, O or S; and
Z is $CH_2$, NH, O or S,
or a pharmaceutically acceptable form thereof, effective to treat, prevent, or reduce one or more cancers, or a related disease or disorder thereof, in a mammal, including a human, and a pharmaceutically acceptable excipient, carrier, or diluent.

BRIEF DESCRIPTION OF THE DRAWINGS

FIG. 1A, the cysteine 379 is showed as a targetable residue; FIG. 1B the cysteine 269 is showed as targetable residue FIG. 2. Exemplary $IC_{50}$ data of representative compound in IDH1 R132H mutant biochemical assays.

DEFINITIONS

Figure 1:
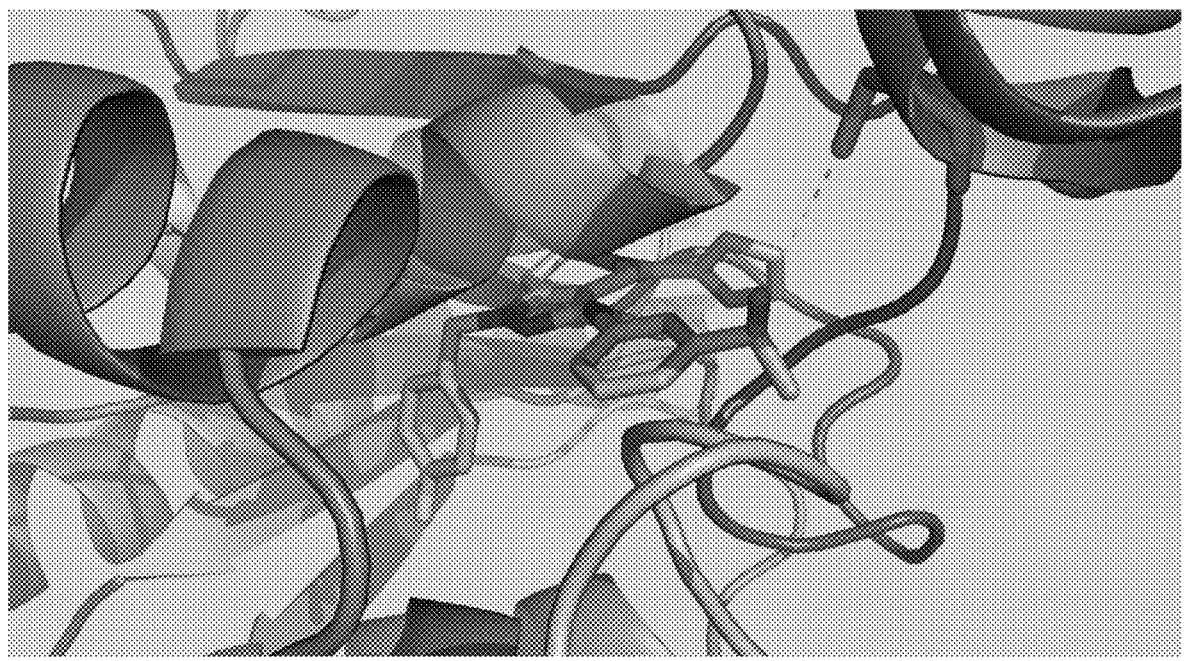
FIG. 1. Crystal structure of IDH1 with GSK321 from PDB:5DE1.
Figure 1:
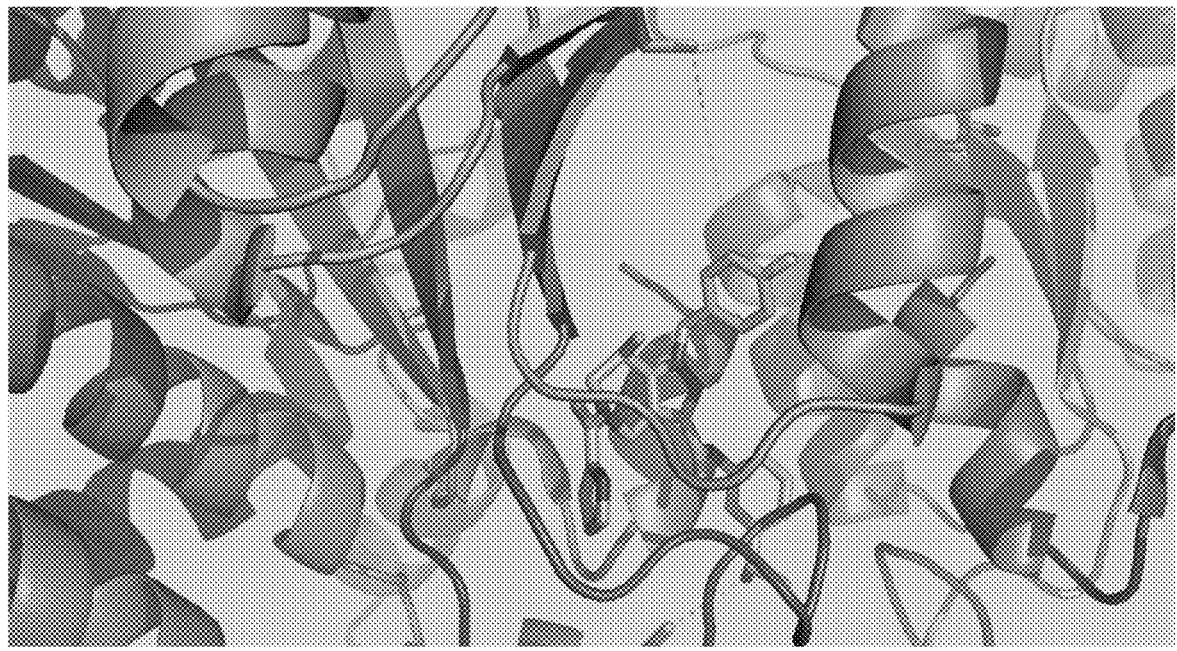
Figure 2:
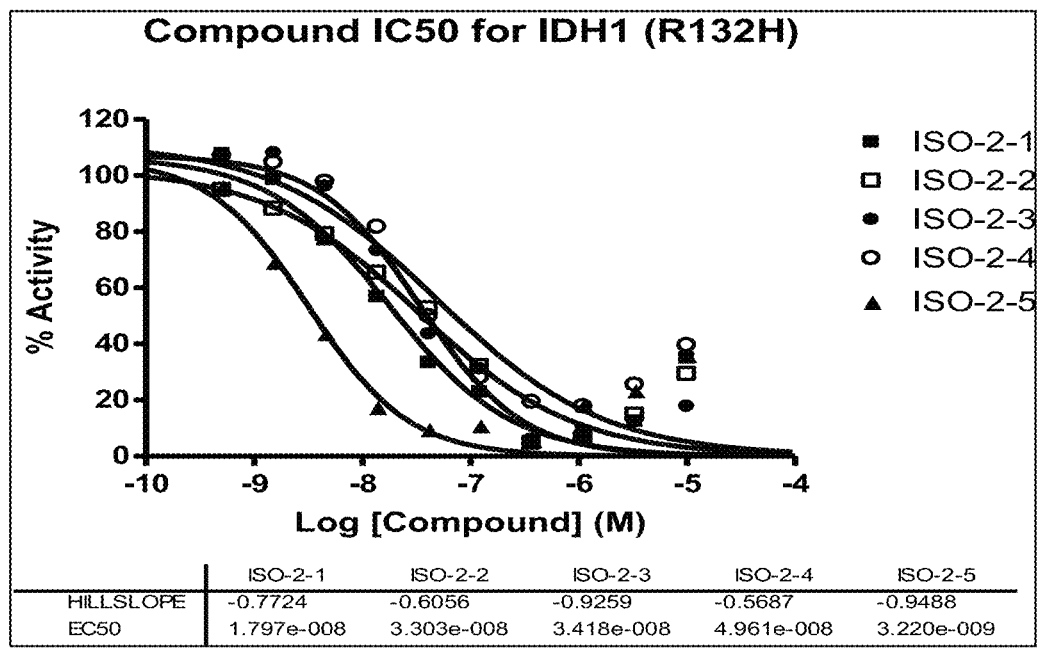
Figure 3:
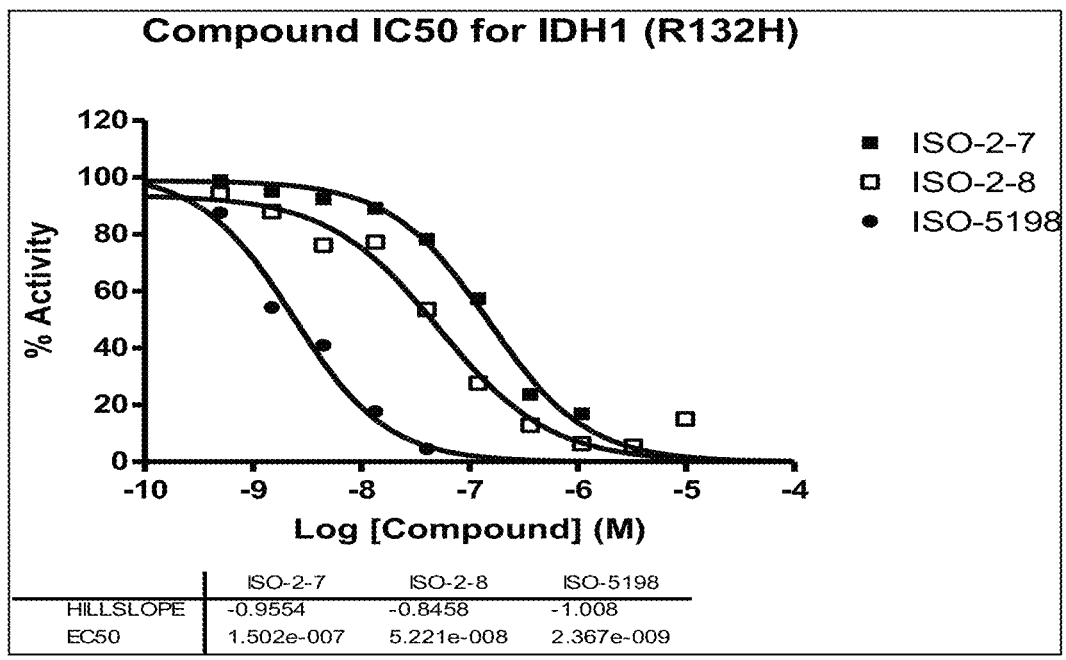
FIG. 3. Exemplary $IC_{50}$ data of representative compound in IDH1 R132H mutant biochemical assays.
Figure 4:
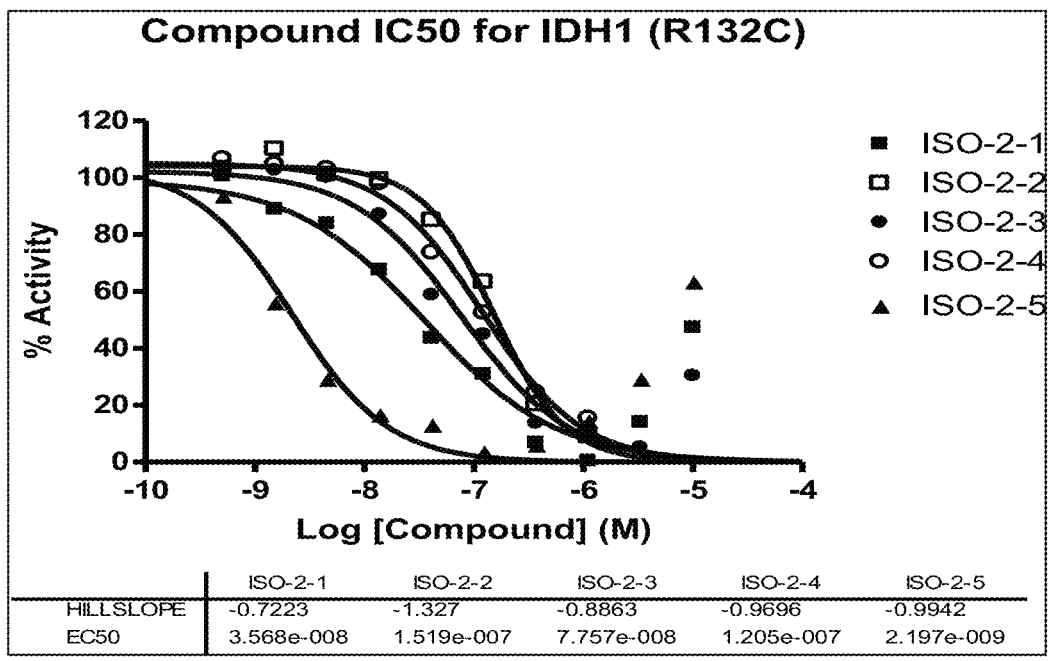
FIG. 4. Exemplary $IC_{50}$ data of representative compound in IDH1 R132C mutant biochemical assays.
Figure 5:
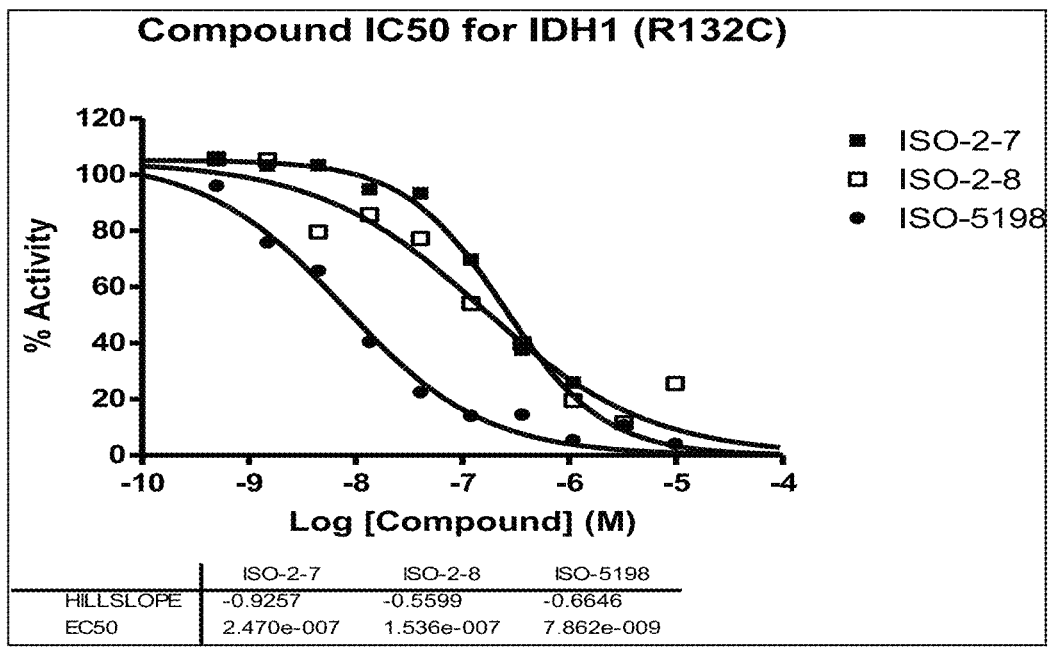
FIG. 5. Exemplary $IC_{50}$ data of representative compound in IDH1 R132C mutant biochemical assays.
Figure 6:
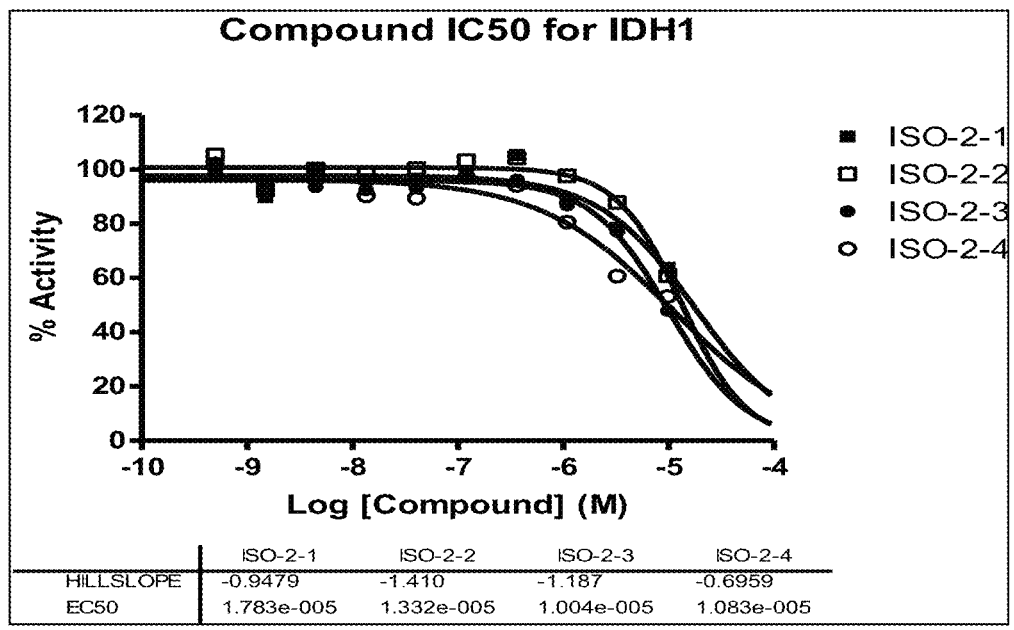
FIG. 6. Exemplary $IC_{50}$ data of representative compound in IDH1 WT biochemical assays.
Figure 7:
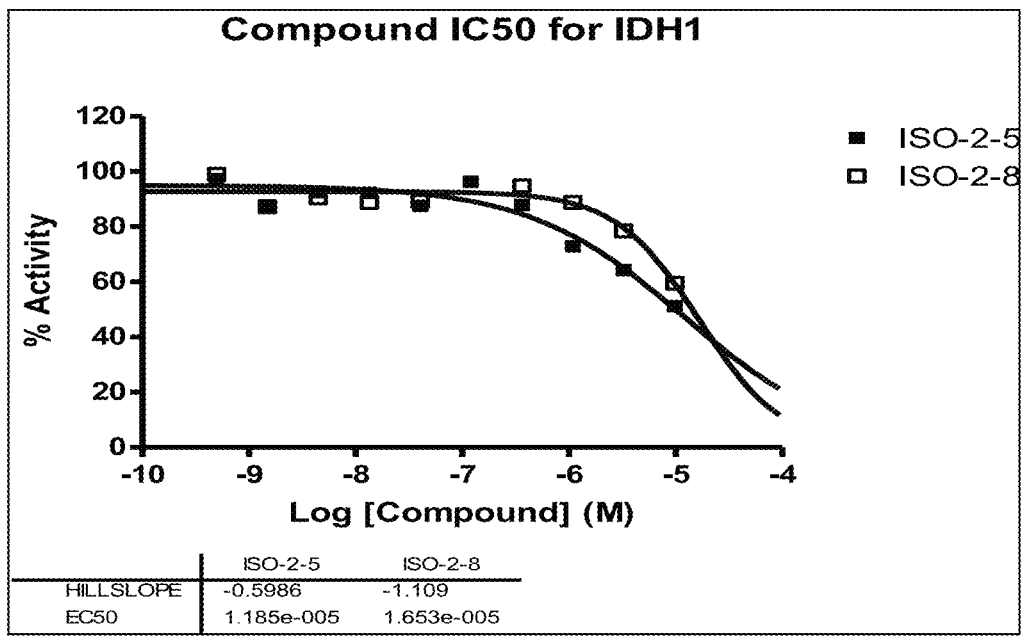
FIG. 7. Exemplary $IC_{50}$ data of representative compound in IDH1 WT biochemical assays.
Figure 8:
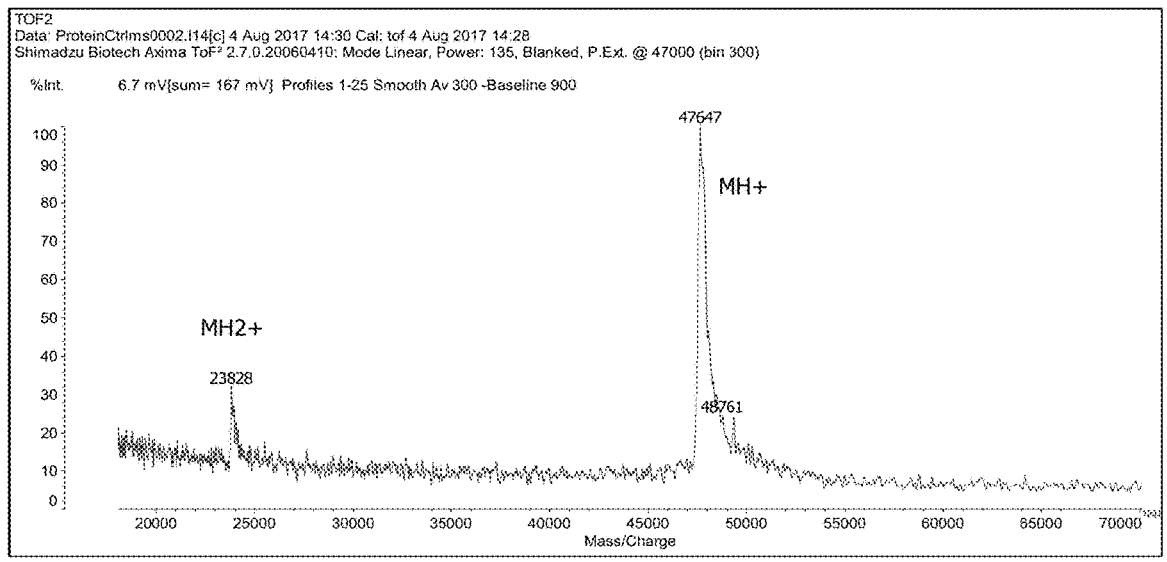
FIG. 8. Exemplary IDH1 R132C intact mass.
Figure 9:
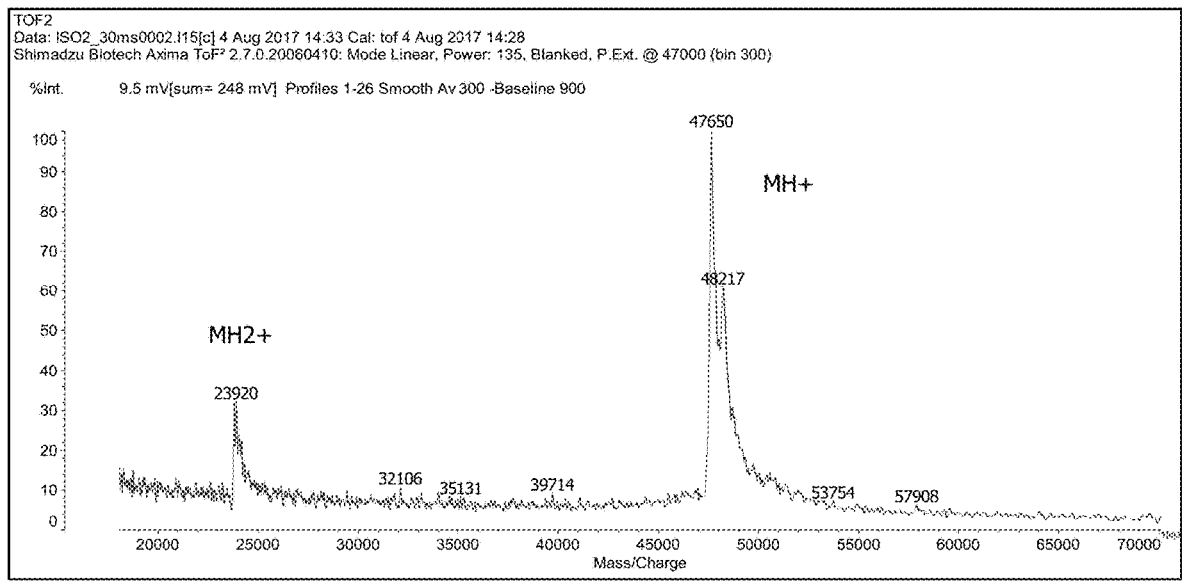
FIG. 9. Exemplary intact mass spectrum of IDH1R132C with ISO-2-30 treatment.
Figure 10:
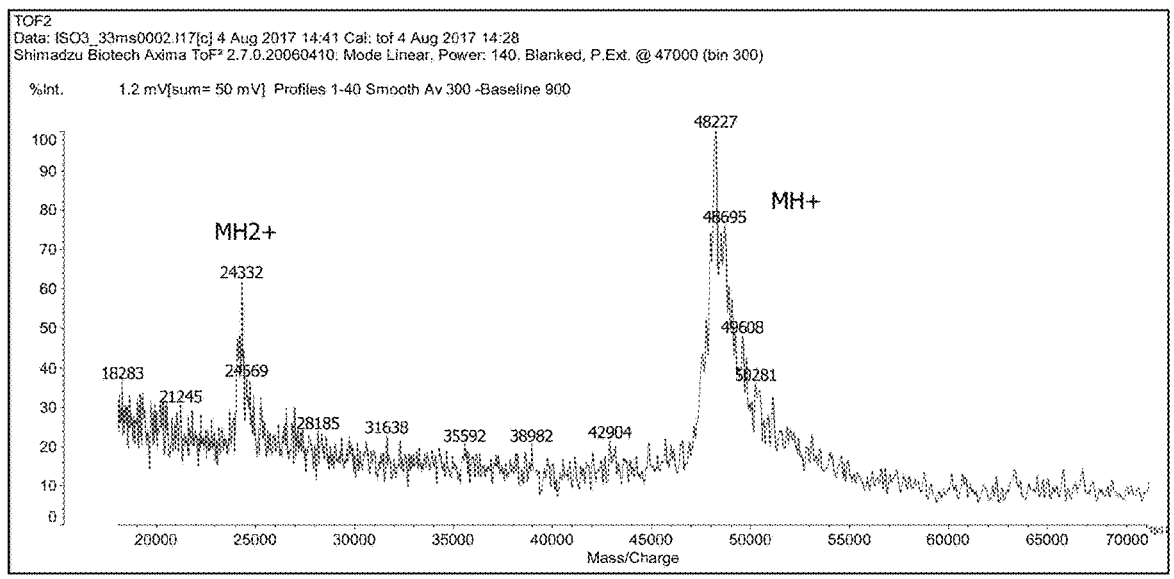
FIG. 10. Exemplary intact mass spectrum of IDH1R132C with ISO-2-38 (another name in mass spectrum:ISO-3-33).
Figure 11:
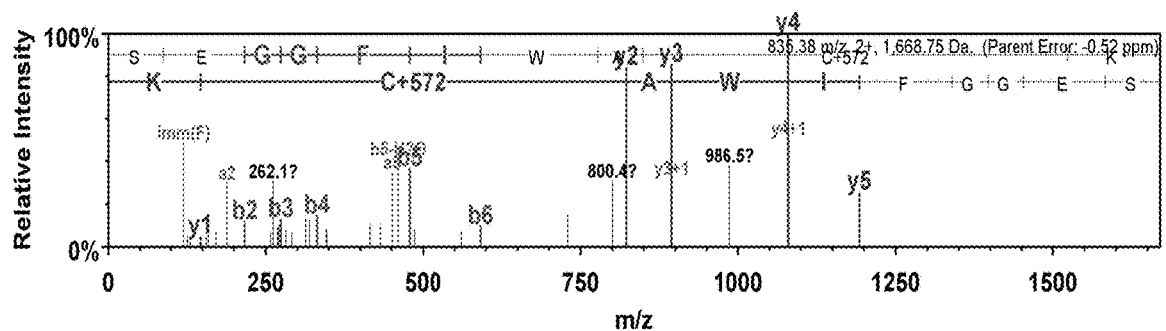
FIG. 11. Exemplary trypsin digestion of labeled IDH1 R132C protein with ISO-2-38 (another name in mass spectrum:ISO-3-33).

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito: 2006.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

As used herein, "administration" of a disclosed compound encompasses the delivery to a subject of a compound as described herein, or a prodrug or other pharmaceutically acceptable derivative thereof, using any suitable formulation or route of administration, as discussed herein.

As used herein, the term "electrophilic group" or "electrophile" refers to group or moiety that is attracted towards and capable of accepting a pair of electrons to form a new covalent bond. Exemplary electrophilic groups include an acrylamide group.

As used herein, the terms "effective amount" or "therapeutically effective amount" refer to that amount of a compound or pharmaceutical composition described herein that is sufficient to effect the intended application including, but not limited to, disease treatment, as illustrated below. In some embodiments, the amount is that effective for detectable killing or inhibition of the growth or spread of cancer cells; the size or number of tumors; or other measure of the level, stage, progression or severity of the cancer. The therapeutically effective amount can vary depending upon the intended application, or the subject and disease condition being treated, e.g., the desired biological endpoint, the pharmacokinetics of the compound, the disease being treated, the mode of administration, and the weight and age of the patient, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment" or "treating" a disease or disorder refers to a method of reducing, delaying or ameliorating such a condition before or after it has occurred. Treatment may be directed at one or more effects or symptoms of a disease and/or the underlying pathology. Treatment is aimed to obtain beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

As used herein, the term "therapeutic effect" refers to a therapeutic benefit and/or a prophylactic benefit as described herein. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the term "pharmaceutically acceptable ester" refers to esters that hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxy or carboxylic acid group of the parent compound.

As used herein, the term "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

As used herein, a "pharmaceutically acceptable form" of a disclosed compound includes, but is not limited to, pharmaceutically acceptable salts, hydrates, esters, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds. In some embodiments, a "pharmaceutically acceptable form" includes, but is not limited to, pharmaceutically acceptable salts, stereoisomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" (or "pro-drug") refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

As used herein, the term "pharmaceutically acceptable" excipient, carrier, or diluent refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Compounds of the present invention are, subsequent to their preparation, preferably isolated and purified to obtain a composition containing an amount by weight equal to or greater than 95% ("substantially pure"), which is then used or formulated as described herein. In certain embodiments, the compounds of the present invention are more than 99% pure.

Solvates and polymorphs of the compounds of the invention are also contemplated herein. Solvates of the compounds of the present invention include, for example, hydrates.

Definitions of specific functional groups and chemical terms are described in more detail below. When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(NR$^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "alkoxy" refers to the group —O-alkyl, including from 1 to 10 carbon atoms ($C_{1-10}$) of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-3}$ alkoxy is an alkoxy group which encompasses both straight and branched chain alkyls of from 1 to 3 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(NR$^a$)N($R^a$)$_2$, —N($R^a$)S(O)$_t$N($R^a$)$_2$ (where t is 1 or 2), —P(=O)($R^a$)($R^a$), or —P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(NR$^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "cycloalkyl" and "carbocyclyl" each refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —$OR^a$, —$SR^a$, —OC(O)—$R^a$, —N($R^a$)$_2$, —C(O)$R_a$, —C(O)$OR^a$, —OC(O)N($R^a$)$_2$, —C(O)N($R^a$)$_2$, —N($R^a$)C(O)$OR^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)($OR^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "halide", "halo", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

As used herein, the term "heteroalkyl" refers to an alkyl radical, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like.

As used herein, the term "heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d] pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5]thieno [2,3-d]pyrimdinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

DETAILED DESCRIPTION OF THE INVENTION

The invention is based on the unexpected discovery of novel, orally available, selective and potent inhibitors of mutated IDH 1 and/or IDH 2 proteins. The compounds disclosed here form irreversible covalent bond or reversible binding interactions with mutant IDH 1 and/or IDH 2 protein and effectively inhibit their respective alpha hydroxyl neoactivity.

Several IDH inhibitors are currently being studied including GSK321 and AG-221. These compounds reportedly bind to IDH1, IDH2, or both IDH1 and IDH2 in a reversible manner.

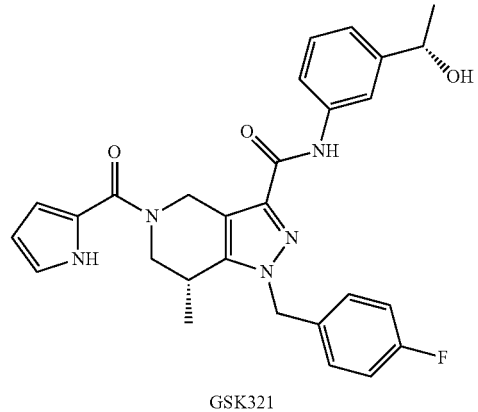 [SMILES: C[C@H](O)c1cccc(NC(=O)c2nn(Cc3ccc(F)cc3)c3c2CN(C(=O)c2ccc[nH]2)C[C@H]3C)c1]

GSK321

The reported reversible inhibitors have shown less than optimal potency, selectivity and exposure time.

In contrast, in certain aspects the present invention provides a unique, irreversible inhibition strategy that affords significant improved potency, selectivity and exposure time presumably due to the covalent bonding and a prolonged pharmacodynamics.

Additionally, in certain aspectsm the present invention provides an optimized, reversible inhibition compounds that affords significant improved potency, selectivity and exposure time.

As disclosed herein below, cysteine 379 of IDH1 (cys379: fmtkdlaacikglpnvqrsd) is selected as a target for irreversible covalent bond formation. The cysteine, which has proximity of 3.8 Å to the hydroxyl group on GSK321 (FIG. 1), is discovered to be a suitable target for irreversible covalent bond formation.

As disclosed herein below, cysteine 269 of IDH1 (cys269: seggfiwacknydgdvqsds) is also selected as a target for irreversible covalent bond formation. The cysteine, which has proximity of 8 Å to the phenyl ring on GSK321 (FIG. 1), is discovered to be a suitable target for irreversible covalent bond formation.

The new strategy disclosed herein allows the translation of a reversible IDH1/2 inhibitor to an irreversible or reversible inhibitor by incorporation an appropriate functional group, such as an electrophilic group (e.g., acrylamide) to form a covalent bond (e.g., S—C bond) or binding interaction with the targetable amino acid (e.g., cysteine).

A series of novel compounds are specifically designed, synthesized and tested. These compounds, each bearing an electrophilic group suitable for reaction with the target cysteine to form an irreversible covalent bond or a reversible binding interaction.

Advantages of the approach disclosed herein include sustained target inhibition, which can be achieved with only transient exposure of the target to the inhibitor. This approach reduces the need to achieve pharmacological properties that would allow for sustained drug levels in vivo.

In one aspect, the invention generally relates to a compound having the structural formula of (I):

(I)

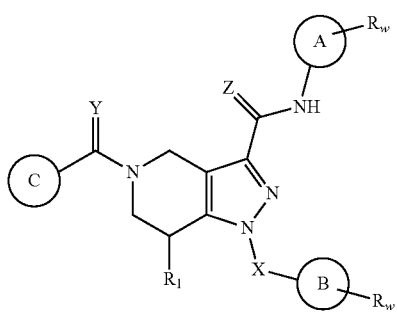

wherein,
each of Ring A, Ring B and Ring C is independently a 5- or 6-membered cyclic or bicyclic alkyl, heteroalkyl, aryl, or heteroaryl ring;
each $R_W$ is independently a hydrogen, a halide, OH, $NH_2$, alkyl, alkyl amine, alkyl amide, alkoxy, or an electrophilic group $R_E$;
$R_1$ is H, halide, alkyl amine, methoxy, hydroxy or a $C_1$-$C_3$ alkyl group;
X is $CH_2$, NH, O, S or a single bond;
Y is $CH_2$, NH, O or S; and
Z is $CH_2$, NH, O or S,
or a pharmaceutical acceptable form thereof.

In certain embodiments, each of Ring A, Ring B and Ring C is independently a 5,6-bicyclic aryl or heteroaryl, or a 6,6-bicyclic aryl or heteroaryl.

In certain embodiments, the compound has the structural formula of (II).

(II)

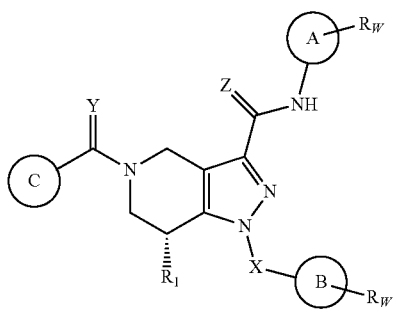

In certain embodiments, the compound has the structural formula of (I-A).

(I-A)

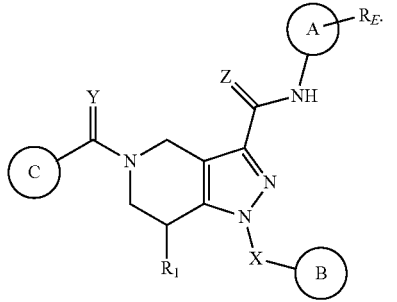

In certain embodiments, the compound has the structural formula of (II-A).

(II-A)

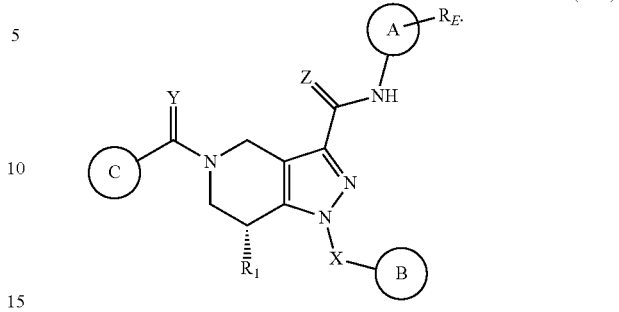

In certain embodiments, the compound has the structural formula of (I-B).

(I-B)

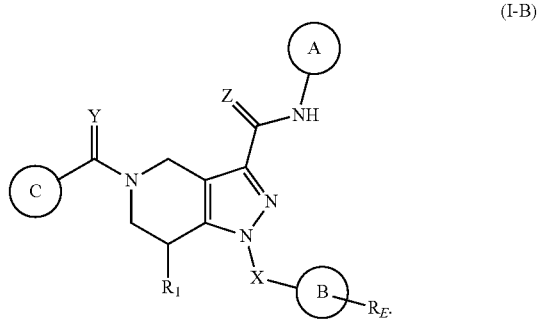

In certain embodiments, the compound has the structural formula of (II-B).

(II-B)

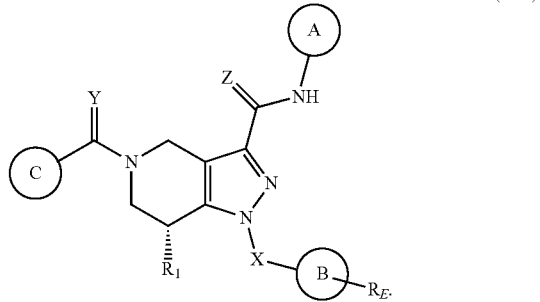

In certain embodiments, the compound has the structural formula of (I-C):

(I-C)

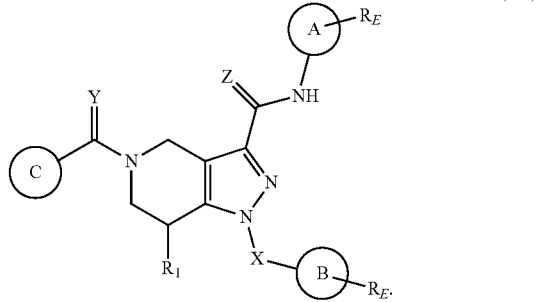

In certain embodiments, the compound has the structural formula of (II-C):

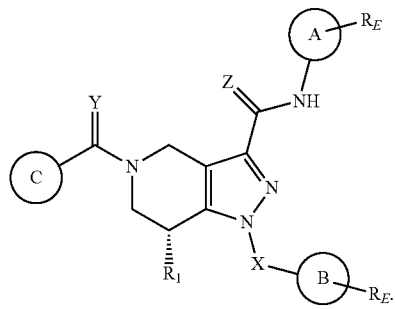

In certain embodiments, each of Ring A and Ring B is a 6-membered aryl group and Ring C is a 5-membered aryl group.

In certain embodiments, the compound has the structural formula of:

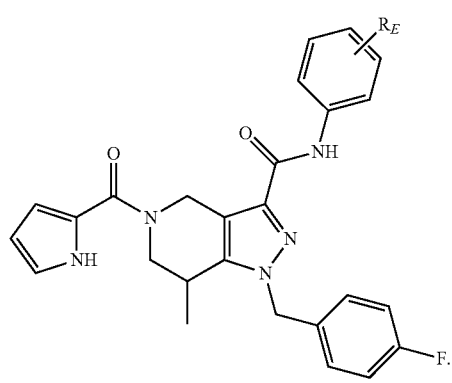

In certain embodiments, the compound has the structural formula of:

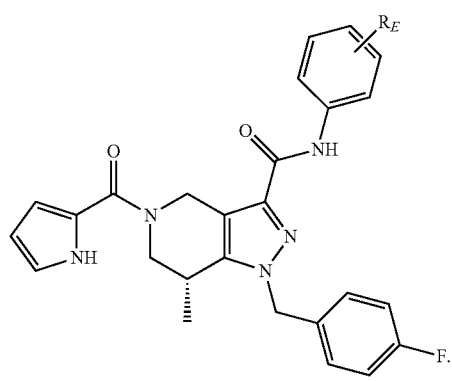

In certain embodiments, the compound has the structural formula of:

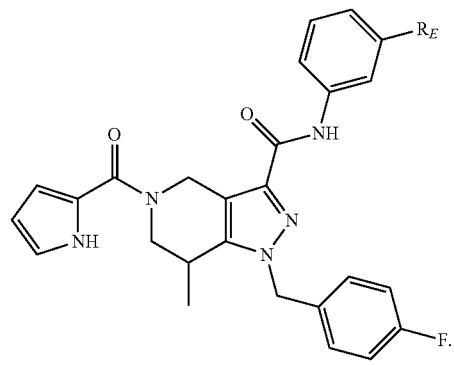

In certain embodiments, the compound has the structural formula of:

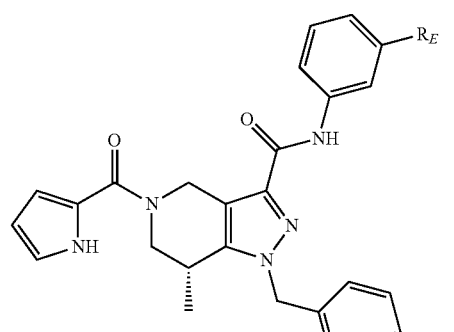

In certain embodiments, the compound has the structural formula of:

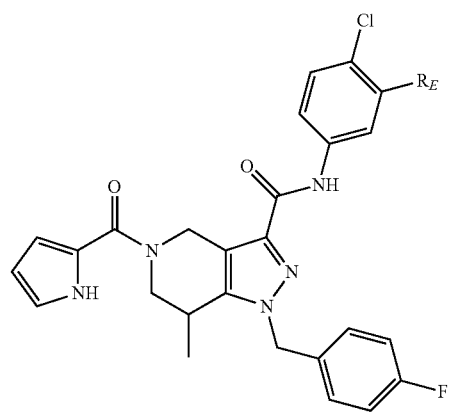

In certain embodiments, the compound has the structural formula of:

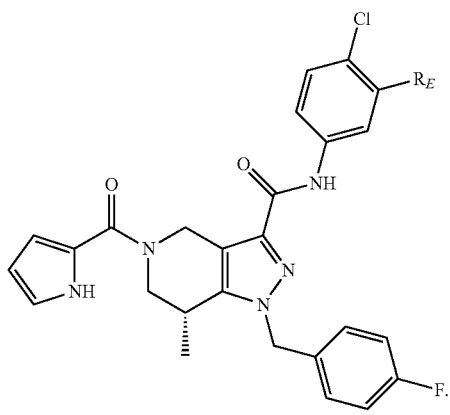

In certain embodiments, the compound has the structural formula of:

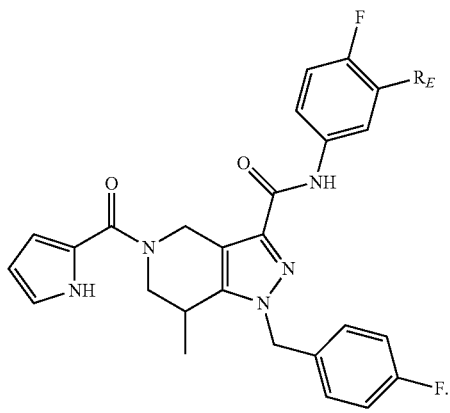

In certain embodiments, the compound has the structural formula of:

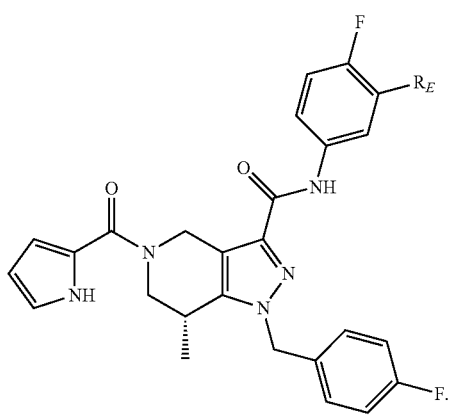

In certain embodiments, the compound has the structural formula of:

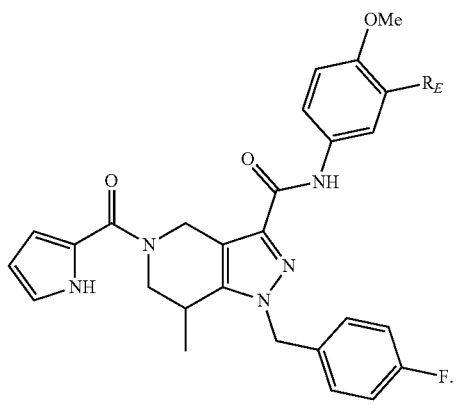

In certain embodiments, the compound has the structural formula of:

In certain embodiments, the compound has the structural formula of:

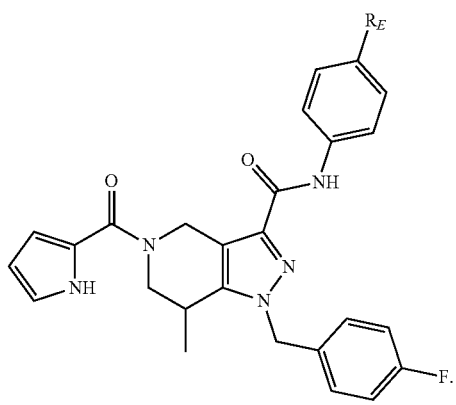

In certain embodiments, the compound has the structural formula of:

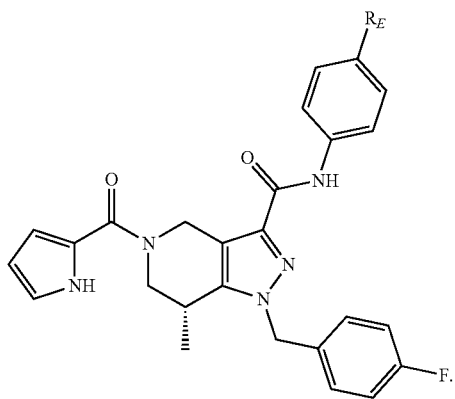

In certain embodiments, the compound has the structural formula of:

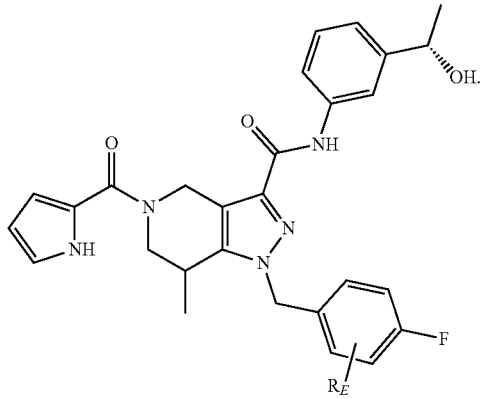

In certain embodiments, the compound has the structural formula of:

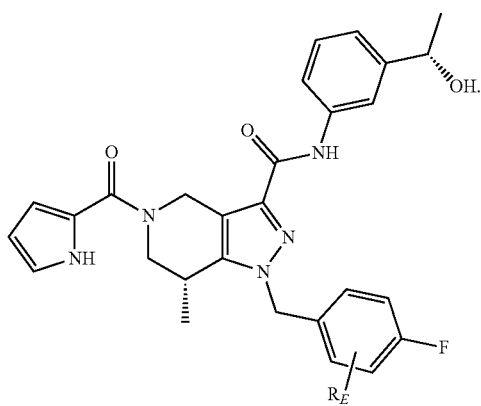

In certain embodiments, the compound has the structural formula of:

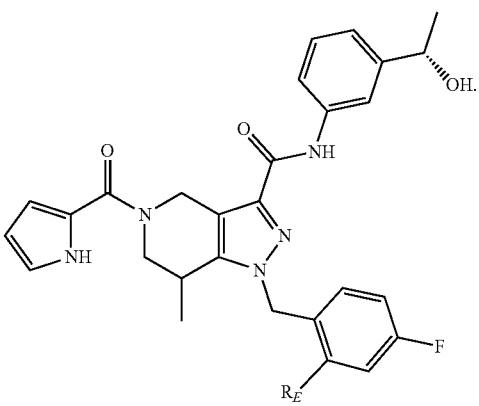

In certain embodiments, the compound has the structural formula of:

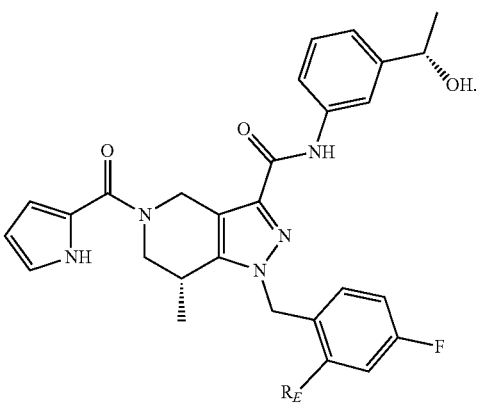

In certain embodiments, the compound has the structural formula of:

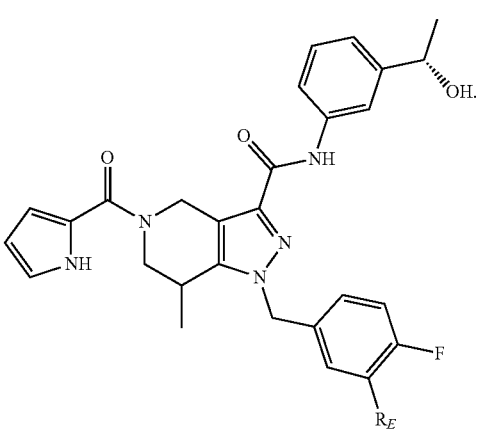

In certain embodiments, the compound has the structural formula of:

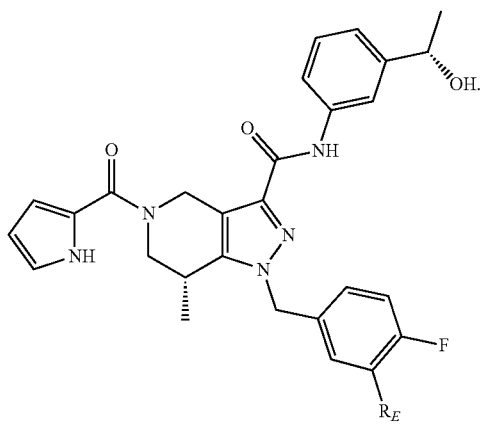

In certain embodiments, the compound has the structural formula of:

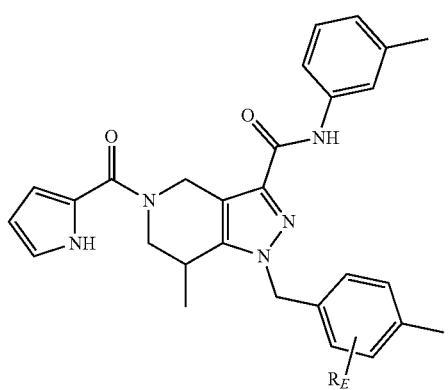

In certain embodiments, the compound has the structural formula of:

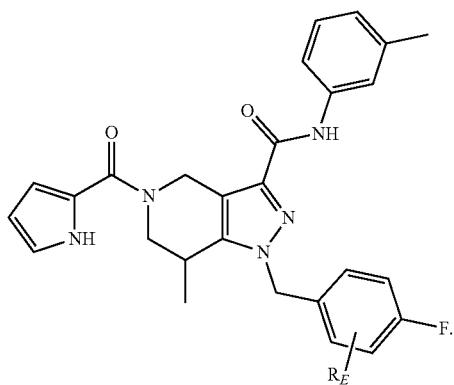

In certain embodiments, the compound has the structural formula of:

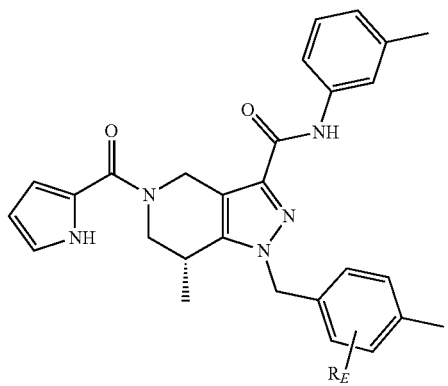

In certain embodiments, the compound has the structural formula of:

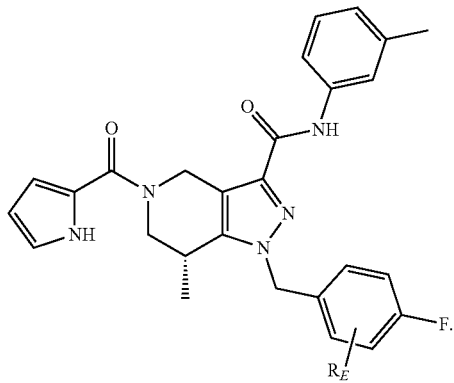

In certain embodiments, the compound has the structural formula of:

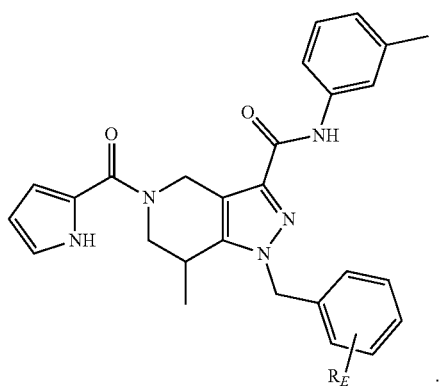

In certain embodiments, the compound has the structural formula of:

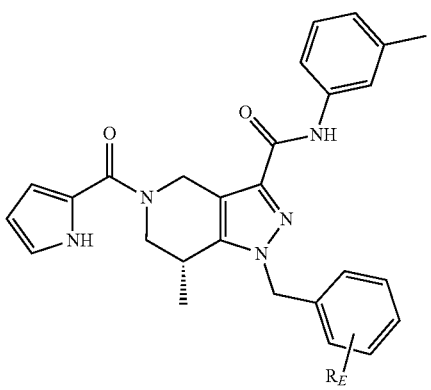

In certain embodiments, the compound has the structural formula of:

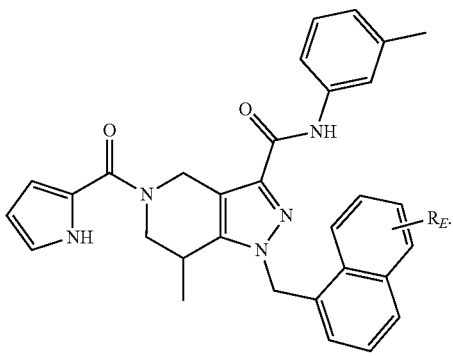

In certain embodiments, the compound has the structural formula of:

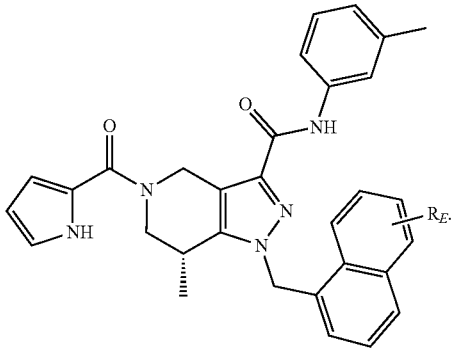

$R_E$ may be any suitable electrophilic group. Exemplary $R_E$ groups include the $R_E$ groups found in the exemplary compounds of the invention, as disclosed herein.

In certain embodiments, $R_E$ comprises an acrylamide group. In certain embodiments, $R_E$ is an acrylamide group.

In certain embodiments, $R_E$ comprises

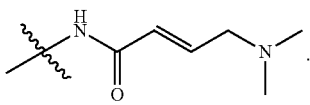 [SMILES: *NC(=O)/C=C/CN(C)C]

In certain embodiments, $R_E$ is

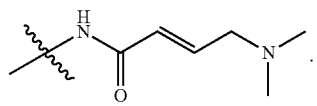 [SMILES: *NC(=O)/C=C/CN(C)C]

In certain embodiments, $R_E$ comprises

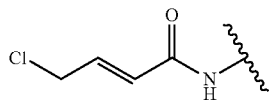 [SMILES: *NC(=O)/C=C/CCl]

In certain embodiments, $R_E$ comprises

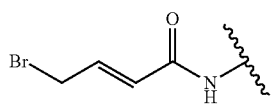

In certain embodiments, $R_E$ comprises

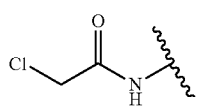 [SMILES: *NC(=O)CCl]

Exemplary compounds of the invention include:

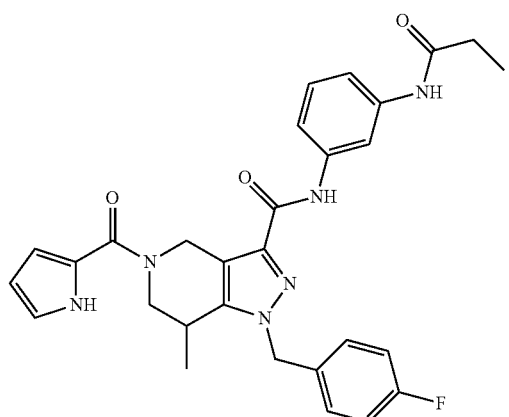

ISO-2-4

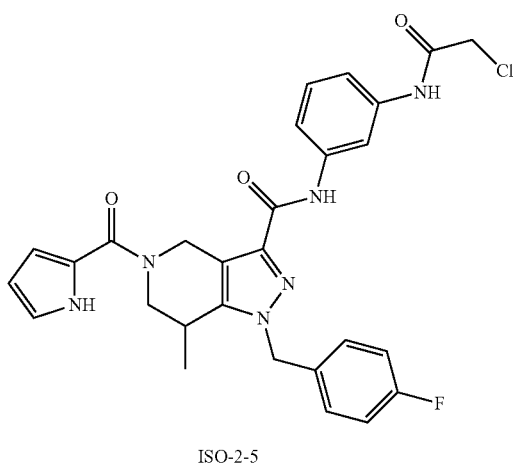
ISO-2-5
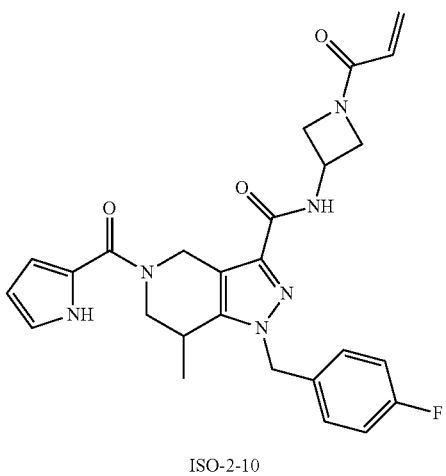
ISO-2-10
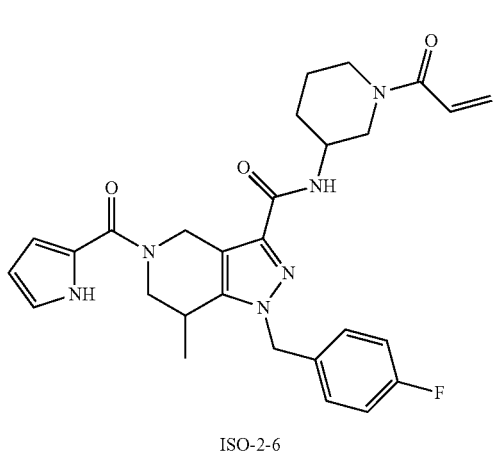
ISO-2-6
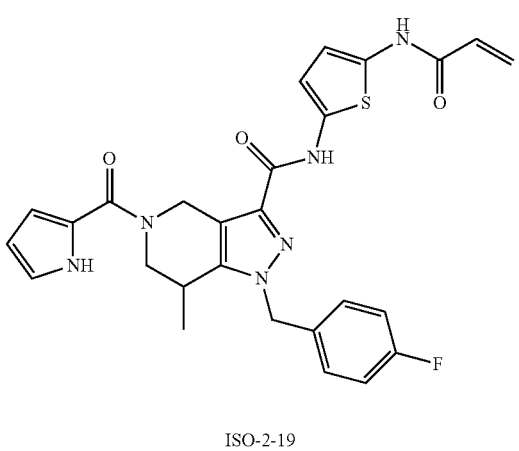
ISO-2-19
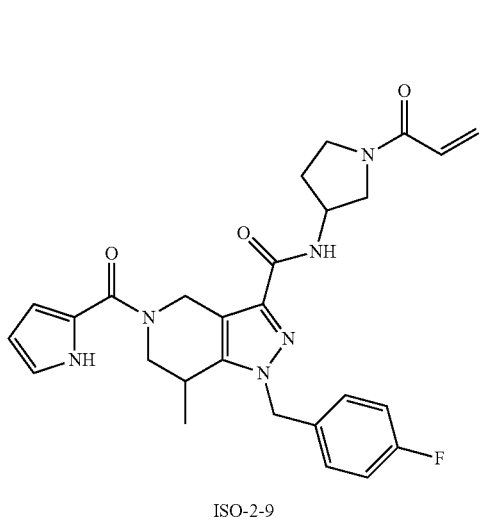
ISO-2-9
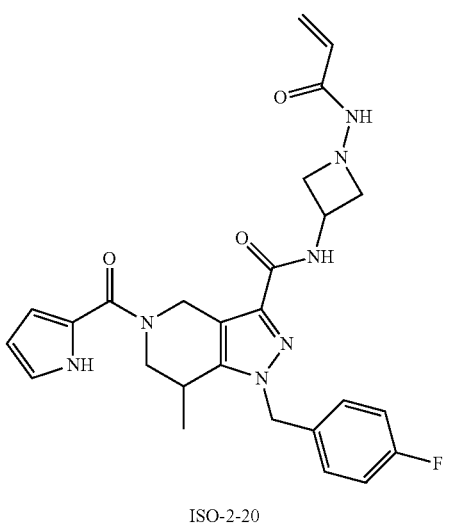
ISO-2-20

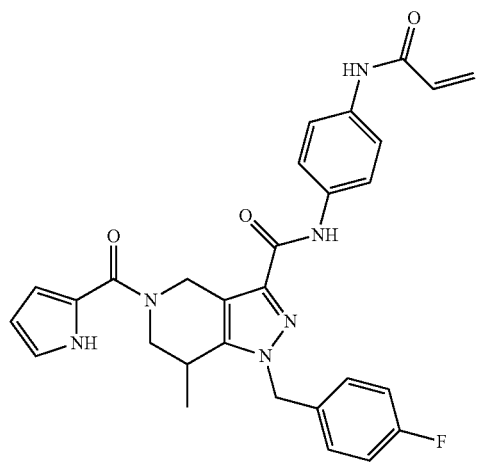
ISO-2-25
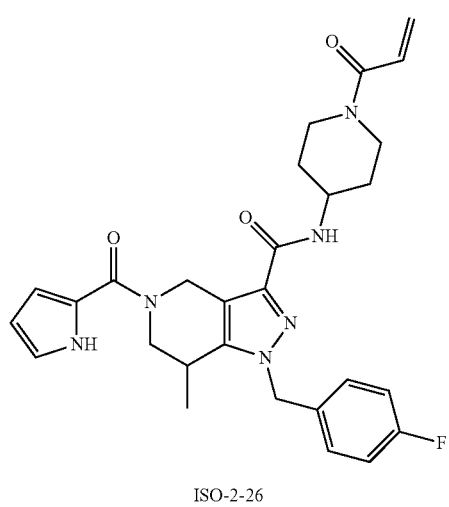
ISO-2-26
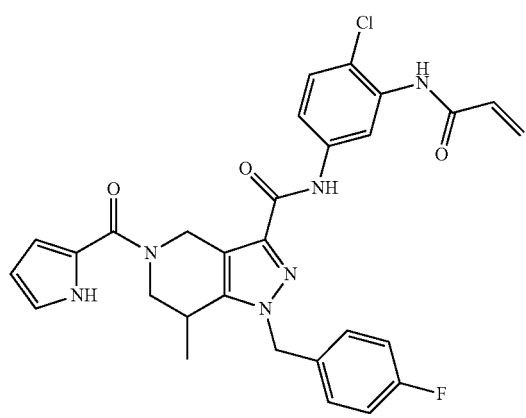
ISO-2-29
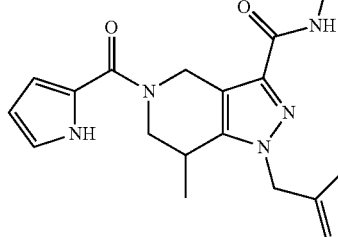
ISO-2-30
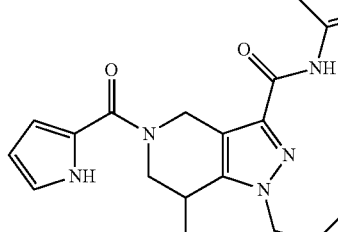
ISO-2-31
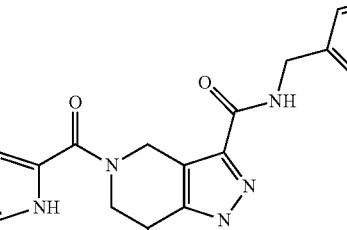
ISO-2-32
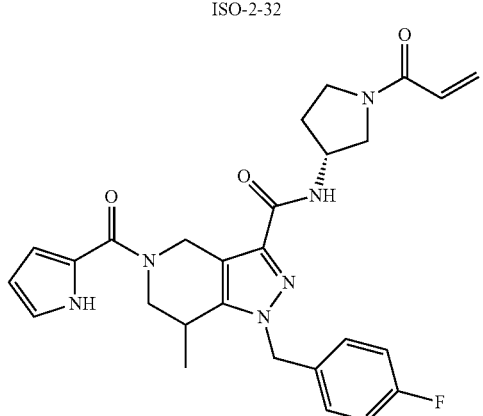
ISO-2-14

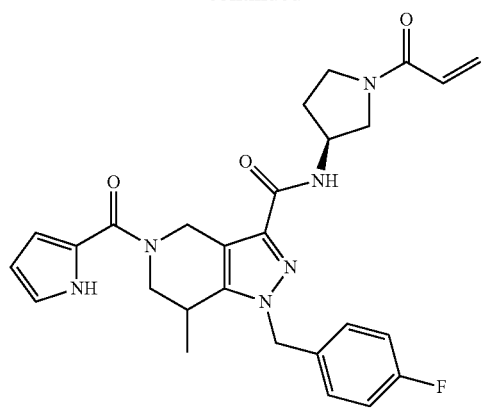
ISO-2-15
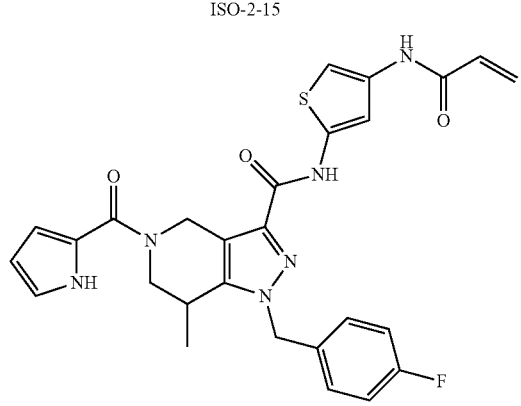
ISO-2-16
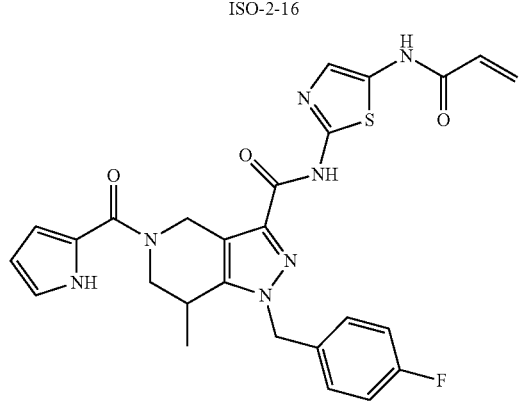
ISO-2-17
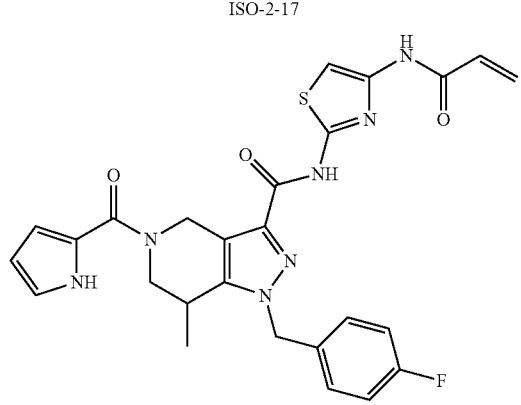
ISO-2-18
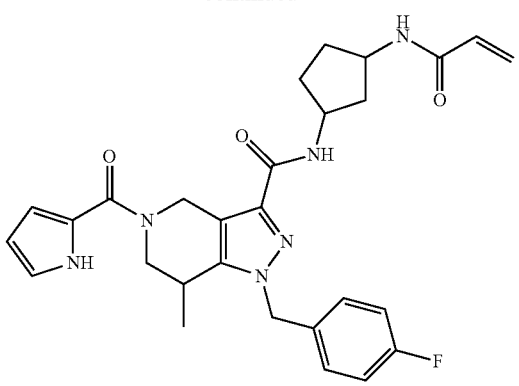
ISO-2-21
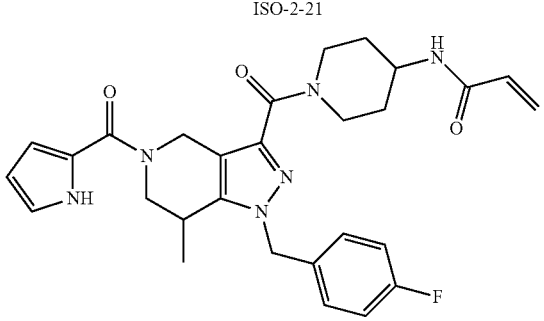
ISO-2-22
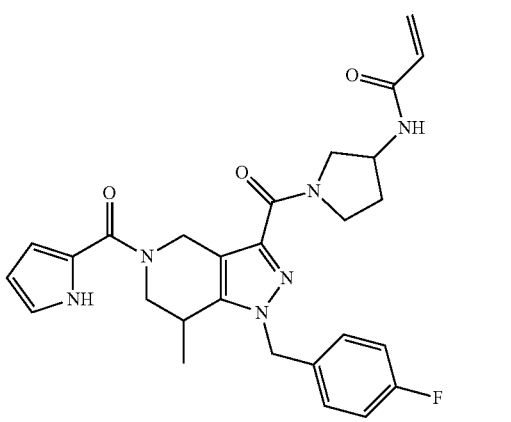
ISO-2-23
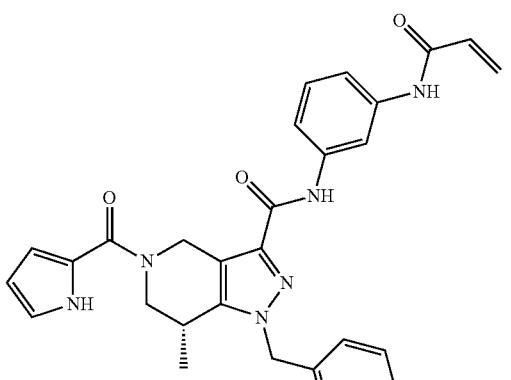
ISO-2-4-R

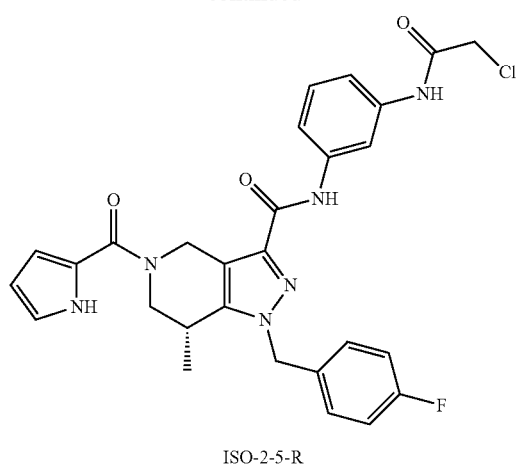
ISO-2-5-R
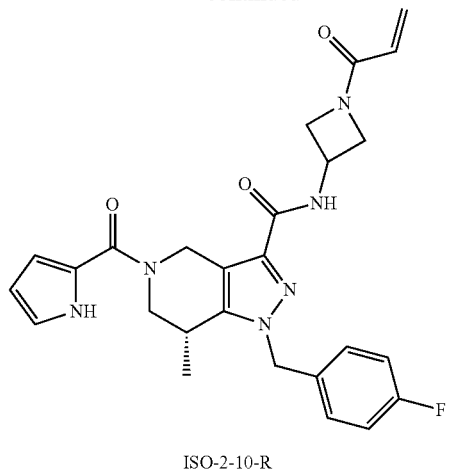
ISO-2-10-R
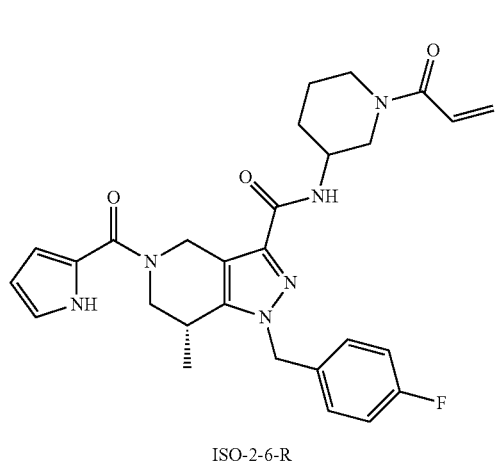
ISO-2-6-R
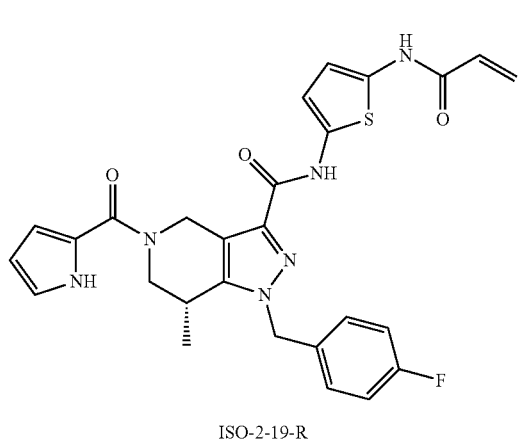
ISO-2-19-R
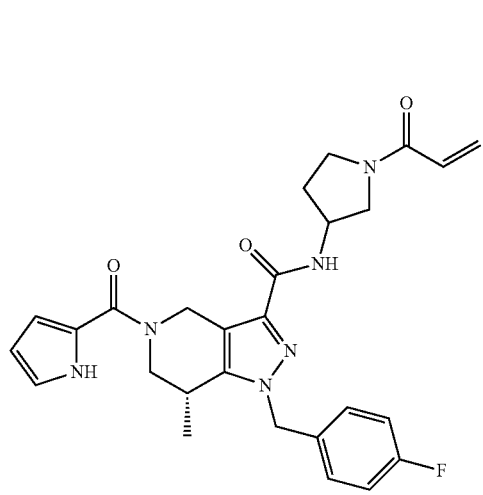
ISO-2-9-R
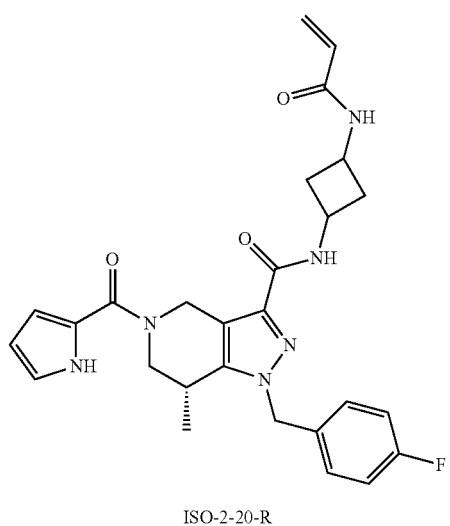
ISO-2-20-R -continued
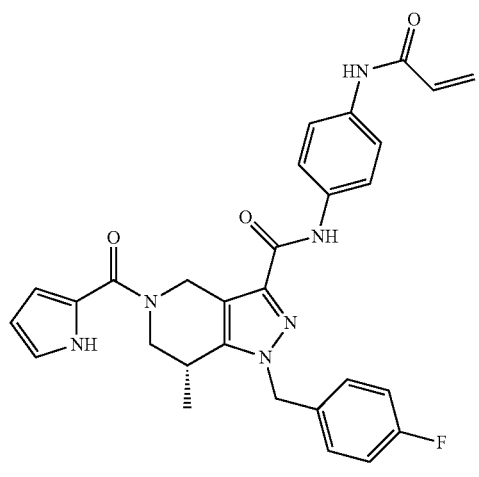
ISO-2-25-R
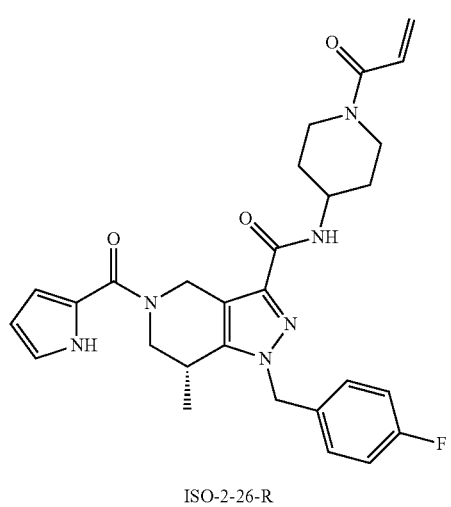
ISO-2-26-R
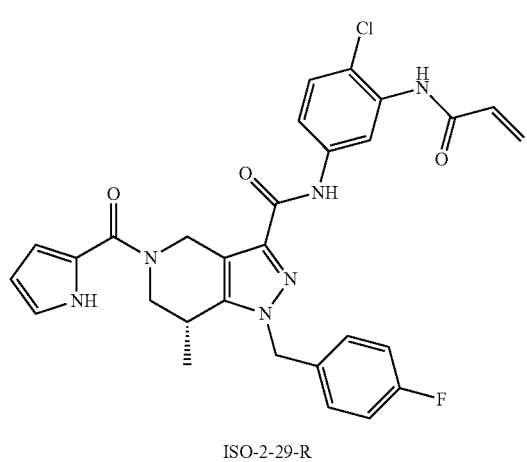
ISO-2-29-R
-continued
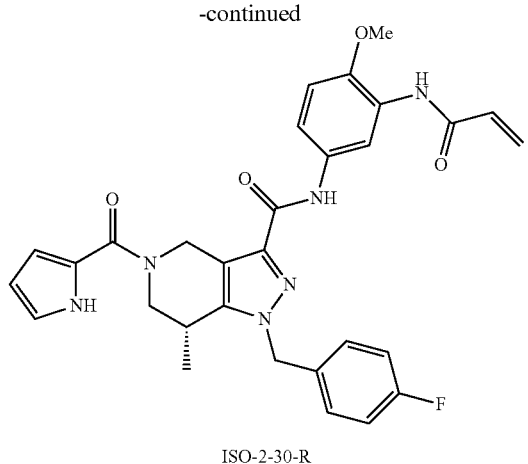
ISO-2-30-R
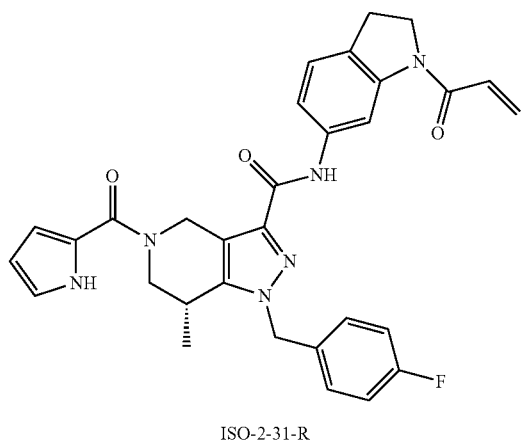
ISO-2-31-R
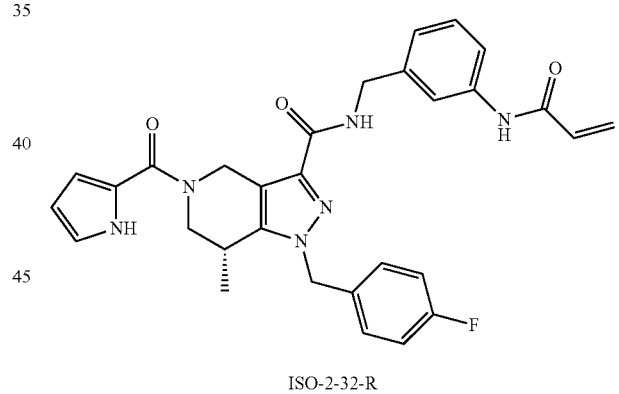
ISO-2-32-R
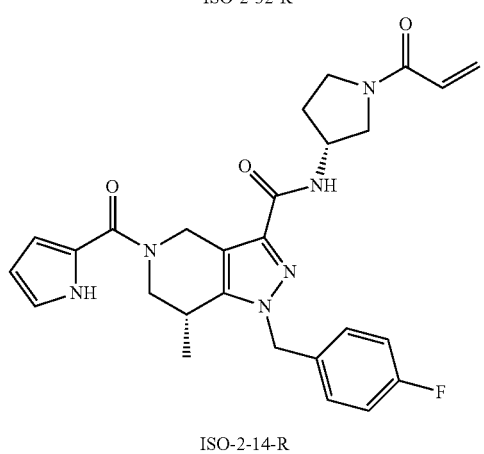
ISO-2-14-R 37
-continued
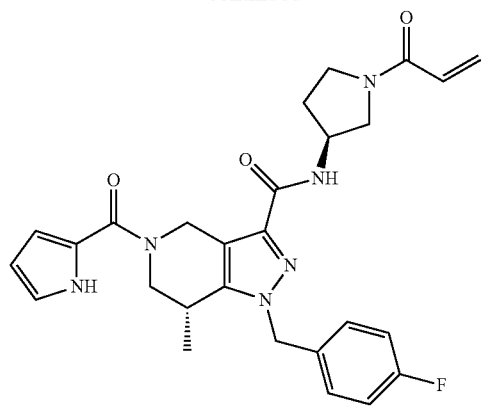
ISO-2-15-R
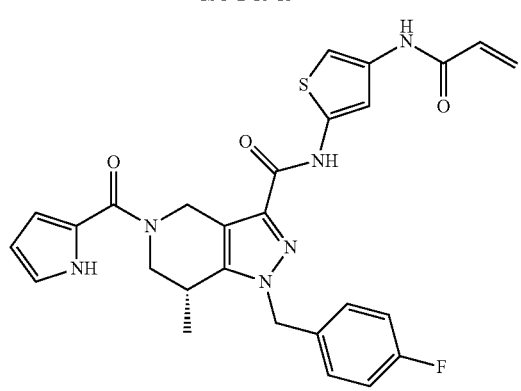
ISO-2-16-R
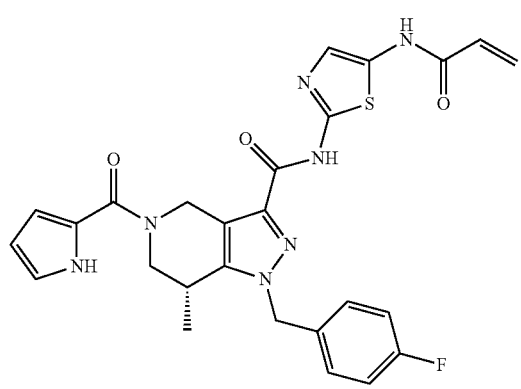
ISO-2-17-R
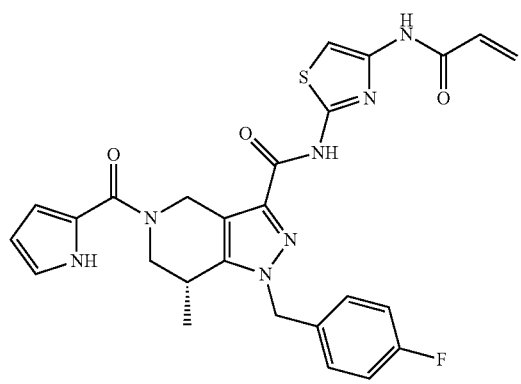
ISO-2-18-R
38
-continued
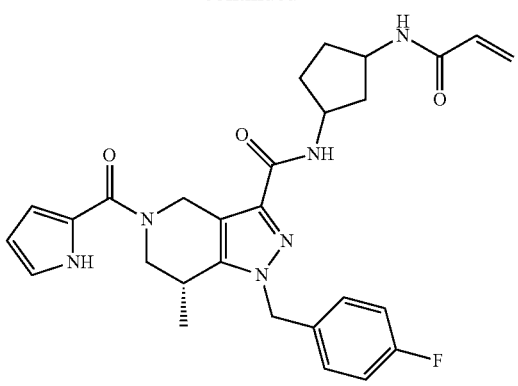
ISO-2-21-R
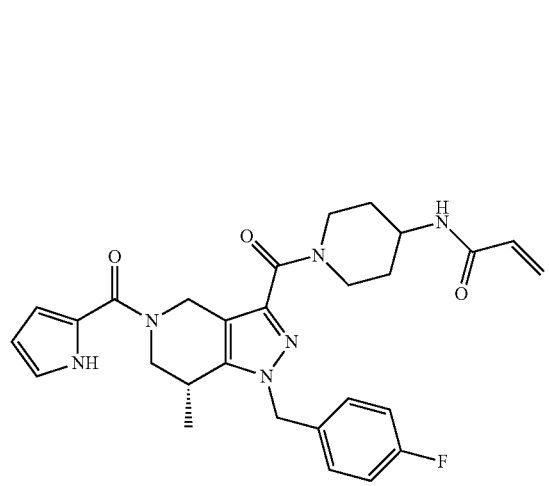
ISO-2-22-R
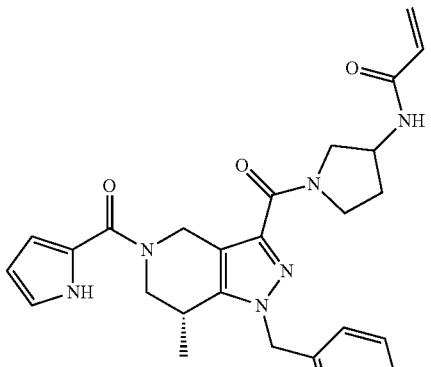
ISO-2-23-R Exemplary compounds of the invention also include:
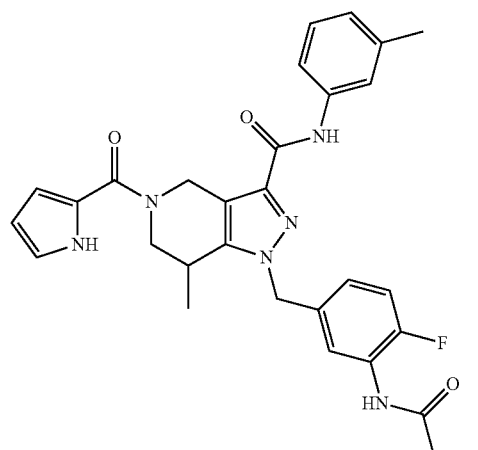
ISO-2-1
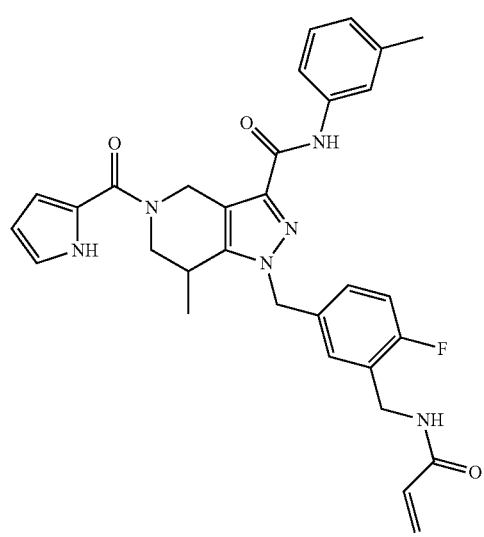
ISO-2-2
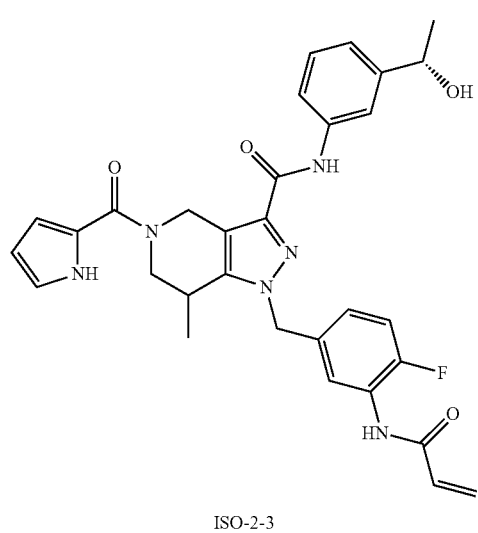
ISO-2-3
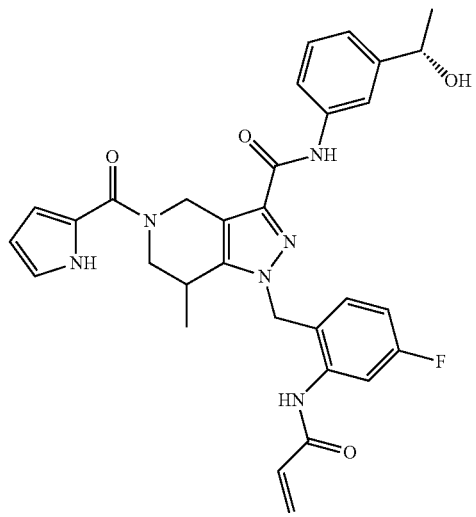
ISO-2-7
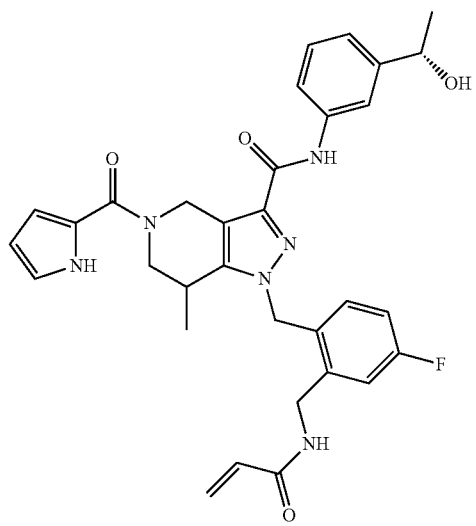
ISO-2-8
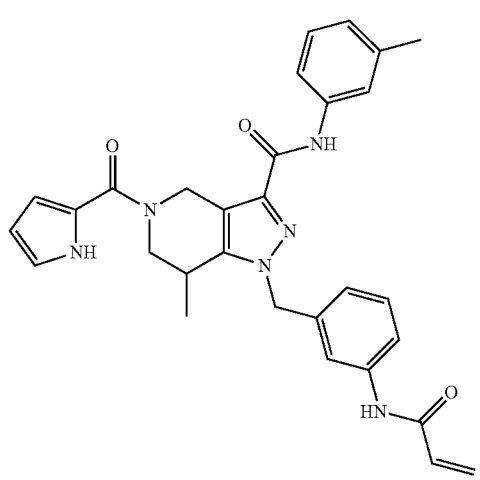
ISO-2-27

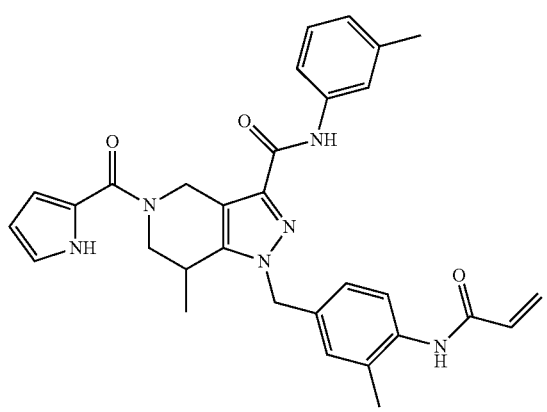
ISO-2-28
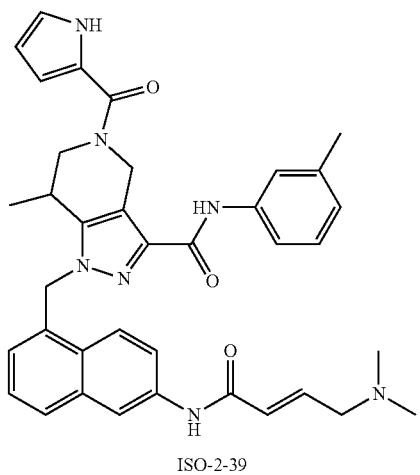
ISO-2-39
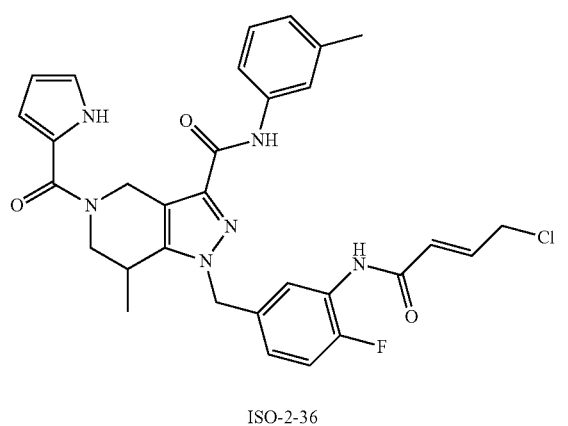
ISO-2-36
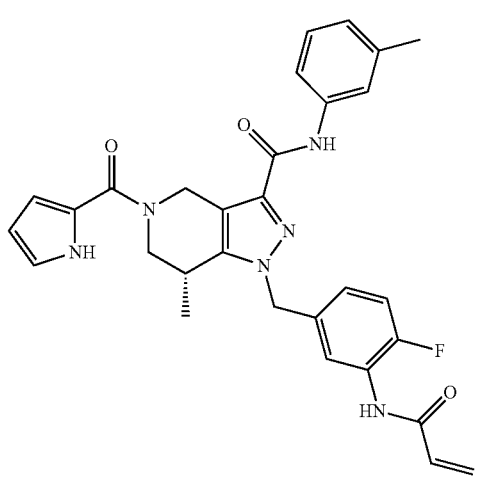
ISO-2-1-R
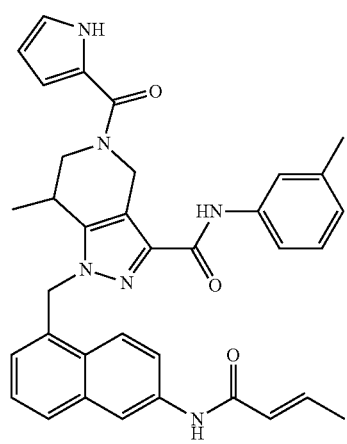
ISO-2-38
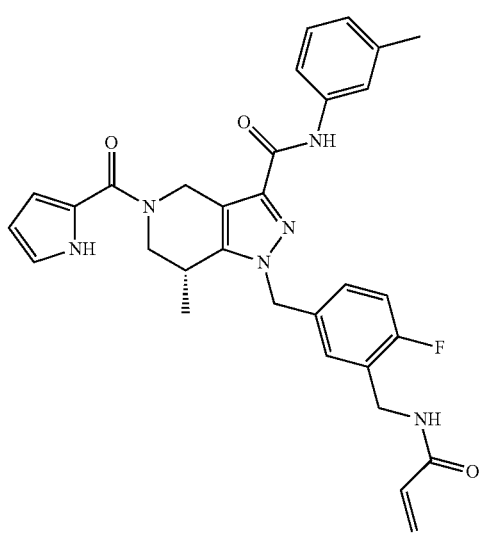
ISO-2-2-R

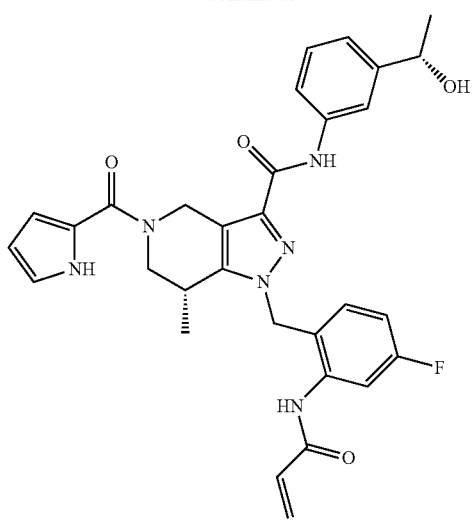
ISO-2-7-R
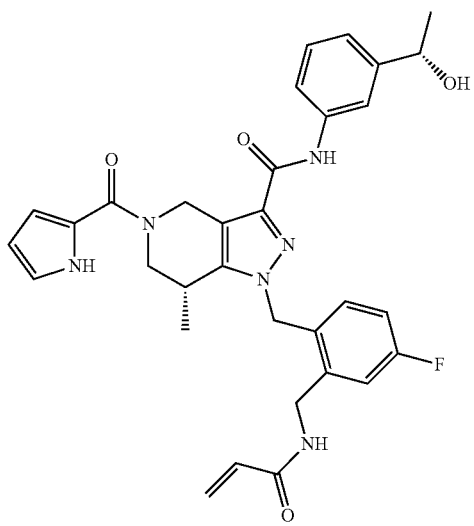
ISO-2-8-R
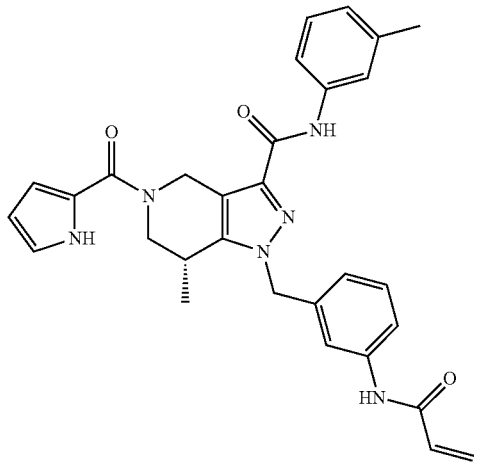
ISO-2-27-R
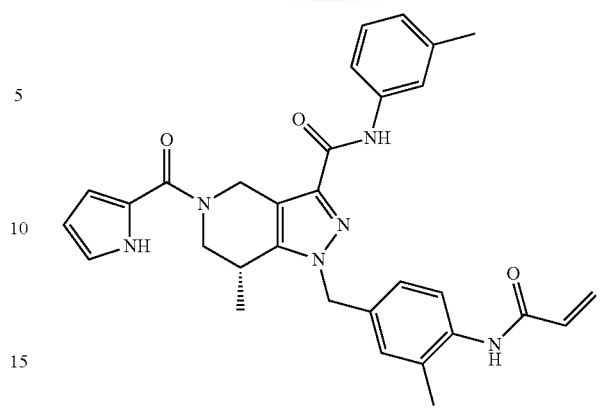
ISO-2-28-R
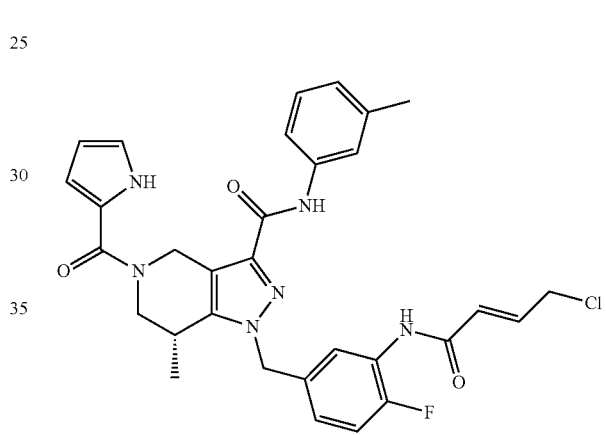
ISO-2-36-R
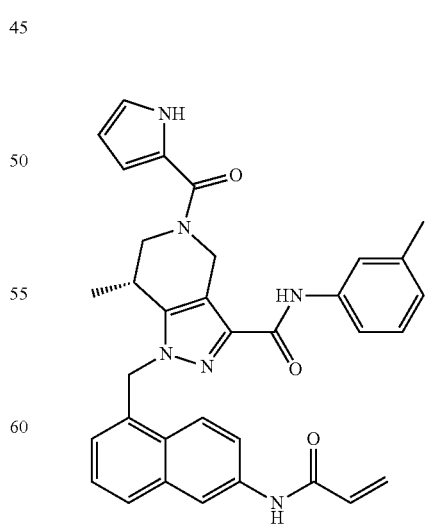
ISO-2-38-R

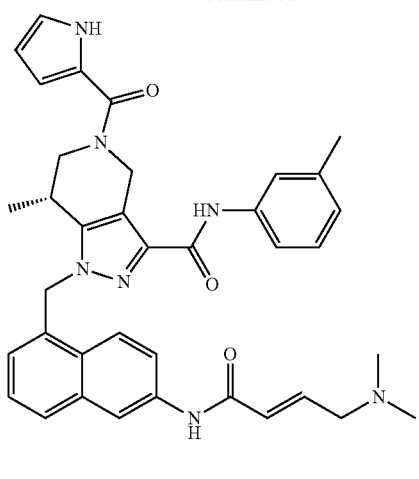

ISO-2-39-R

Exemplary compounds of the invention further include:

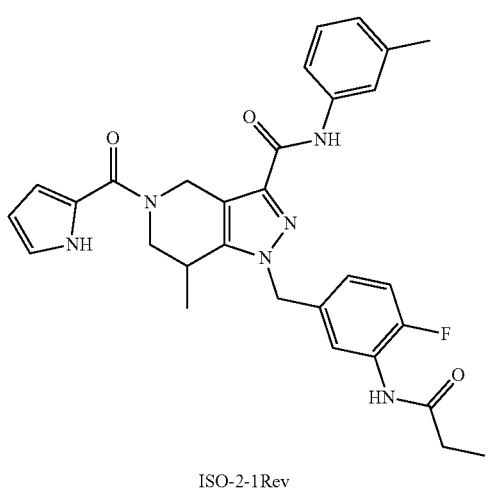

ISO-2-1Rev

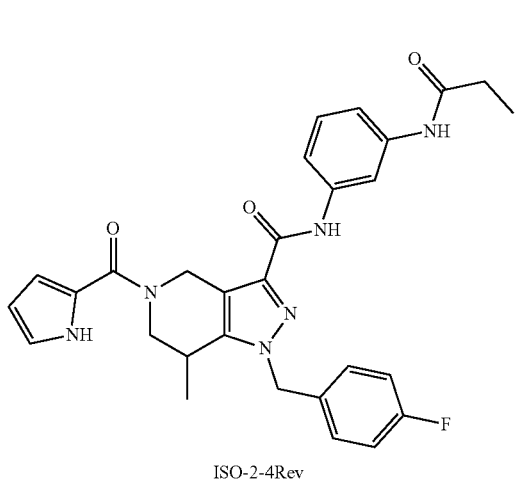

ISO-2-4Rev

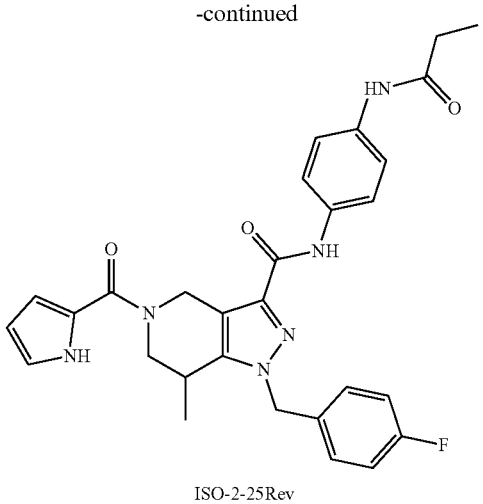

ISO-2-25Rev

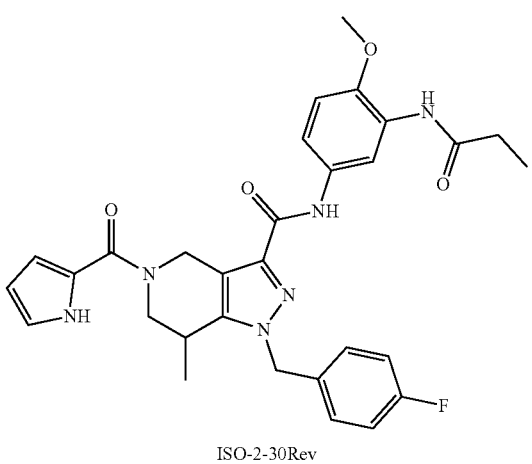

ISO-2-30Rev

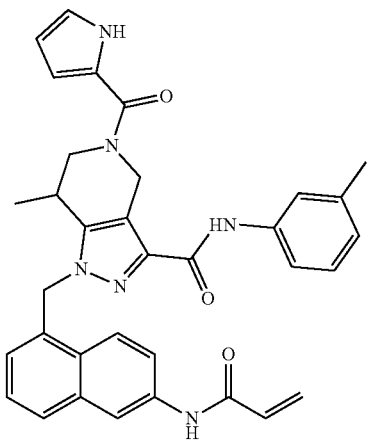

ISO-2-38Rev

A unique aspect of the present invention is the IDH inhibitors disclosed herein form one or more covalent bond with the target IDH. The type of actual covalent bond formed between the inhibitor and the IDH is dependent on the inhibitor's warhead group (e.g., —$R_E$) and the corresponding reactive group on the IDH. Below are illustrative examples involving a cysteine reacting with two electrophilic groups via cysteine's —SH moiety.

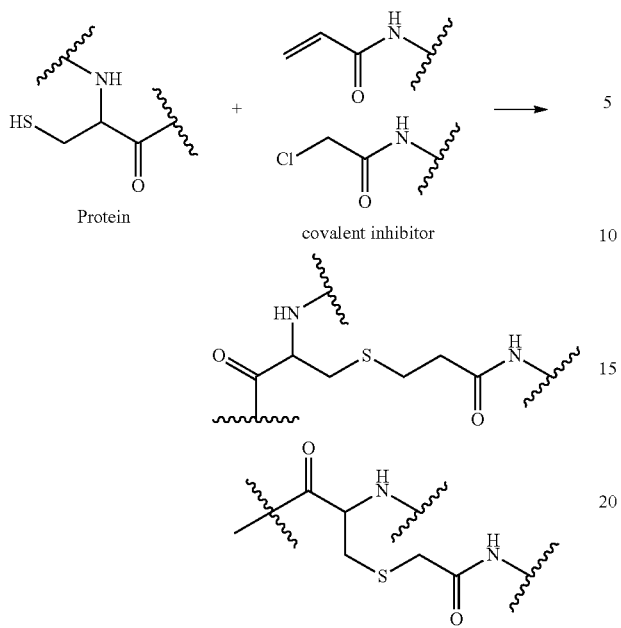

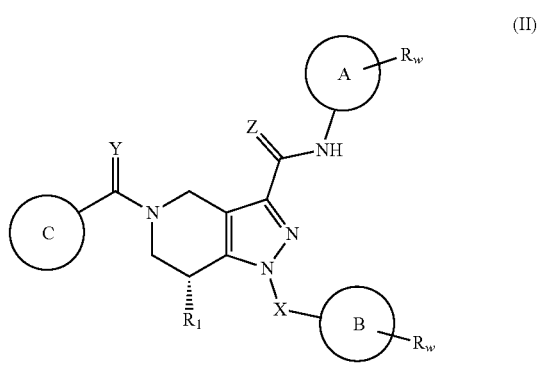

In yet another aspect, the invention generally relates to a pharmaceutical composition comprising a compound disclosed herein.

In yet another aspect, the invention generally relates to a unit dosage form comprising a pharmaceutical composition disclosed herein.

In yet another aspect, the invention generally relates to a method for treating, reducing, or preventing a disease or disorder, comprising administering to a subject in need thereof a pharmaceutical composition comprising a compound having the structural formula of (I):

In another aspect, the invention generally relates to a pharmaceutical composition comprising a compound having the structural formula of (I):

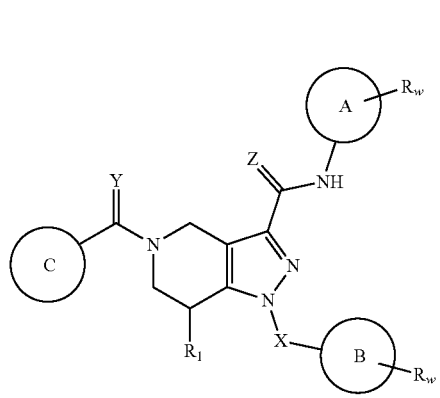

wherein,
each of Ring A, Ring B and Ring C is independently a 5- or 6-membered cyclic or bicyclic alkyl, heteroalkyl, aryl, or heteroaryl ring;
each $R_W$ is independently —$R_E$ or a hydrogen, a halide, OH, $NH_2$, alkyl, alkyl amine, alkyl amide, alkoxy; $R_E$ herein is an electrophilic group.
$R_1$ is H, halide, alkyl amine, methoxy, hydroxy or a $C_1$-$C_3$ alkyl group;
X is $CH_2$, NH, O, S or a single bond;
Y is $CH_2$, NH, O or S; and
Z is $CH_2$, NH, O or S,
or a pharmaceutically acceptable form thereof, effective to treat, prevent, or reduce one or more cancers, or a related disease or disorder thereof, in a mammal, including a human, and a pharmaceutically acceptable excipient, carrier, or diluent.

In certain embodiments, each of Ring A, Ring B and Ring C is independently a 5,6-bicyclic aryl or heteroaryl, or a 6,6-bicyclic aryl or heteroaryl.

In certain embodiments, the compound has the structural formula (II).

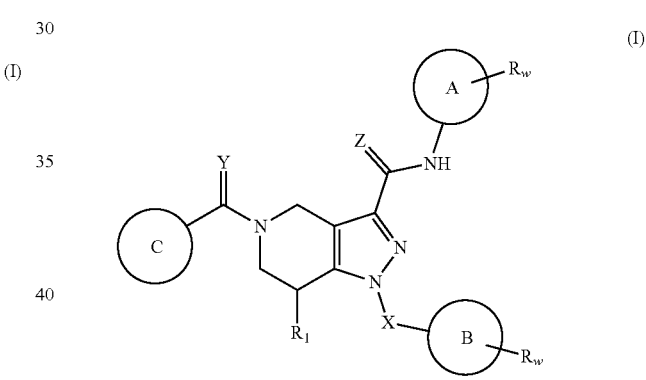

wherein,
each of Ring A, Ring B and Ring C is independently a 5- or 6-membered cyclic or bicyclic alkyl, heteroalkyl, aryl, or heteroaryl ring;
each $R_W$ is independently —$R_E$ or a hydrogen, a halide, OH, $NH_2$, alkyl, alkyl amine, alkyl amide, alkoxy; $R_E$ herein is an electrophilic group.
$R_1$ is H, halide, alkyl amine, methoxy, hydroxy or a $C_1$-$C_3$ alkyl group;
X is $CH_2$, NH, O, S or a single bond;
Y is $CH_2$, NH, O or S; and
Z is $CH_2$, NH, O or S,
or a pharmaceutically acceptable form thereof, effective to treat, prevent, or reduce one or more cancers, or a related disease or disorder thereof, in a mammal, including a human, and a pharmaceutically acceptable excipient, carrier, or diluent.

In certain embodiments, each of Ring A, Ring B and Ring C is independently a 5,6-bicyclic aryl or heteroaryl, or a 6,6-bicyclic aryl or heteroaryl.

In certain embodiments of the method, the compound has the structural formula.

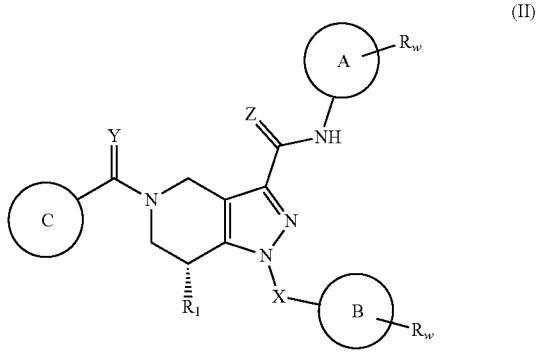

(II)

In certain embodiments, the one or more cancers comprise a blood cancer or a hematologic malignance. In certain embodiments, the one or more cancers are selected from B-acute lymphoblastic leukemias, B-acute lymphoblastic leukemias, chronic myelomonocytic leukemia, Acute myelogenous leukemia, lymphoma, myelodysplasia syndrome, myeloproliferative neoplasms and myeloproliferative neoplasms.

Any appropriate route of administration can be employed, for example, parenteral, intravenous, subcutaneous, intramuscular, intraventricular, intracorporeal, intraperitoneal, rectal, or oral administration. Most suitable means of administration for a particular patient will depend on the nature and severity of the disease or condition being treated or the nature of the therapy being used and on the nature of the active compound.

Solid dosage forms for oral administration include capsules, tablets, pills, powders, and granules. In such solid dosage forms, the compounds described herein or derivatives thereof are admixed with at least one inert customary excipient (or carrier) such as sodium citrate or dicalcium phosphate or (i) fillers or extenders, as for example, starches, lactose, sucrose, glucose, mannitol, and silicic acid, (ii) binders, as for example, carboxymethylcellulose, alignates, gelatin, polyvinylpyrrolidone, sucrose, and acacia, (iii) humectants, as for example, glycerol, (iv) disintegrating agents, as for example, agar-agar, calcium carbonate, potato or tapioca starch, alginic acid, certain complex silicates, and sodium carbonate, (v) solution retarders, as for example, paraffin, (vi) absorption accelerators, as for example, quaternary ammonium compounds, (vii) wetting agents, as for example, cetyl alcohol, and glycerol monostearate, (viii) adsorbents, as for example, kaolin and bentonite, and (ix) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others known in the art.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like. Besides such inert diluents, the composition can also include additional agents, such as wetting, emulsifying, suspending, sweetening, flavoring, or perfuming agents.

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

EXAMPLES
The synthesis of 1-(3-amino-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-1)
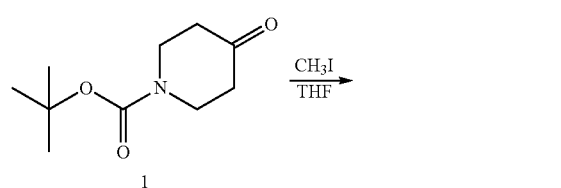
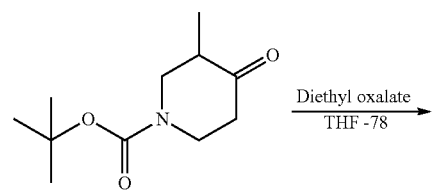
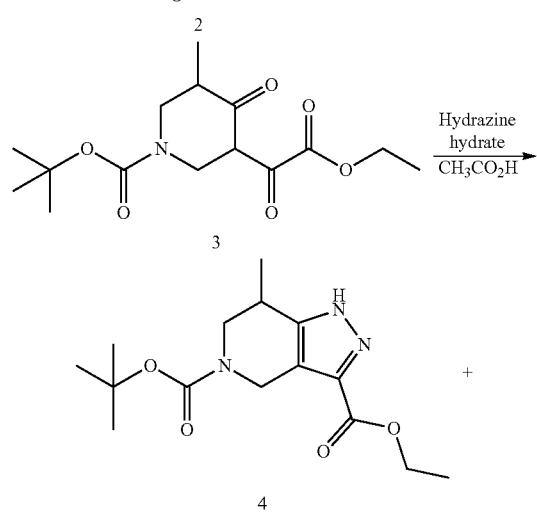
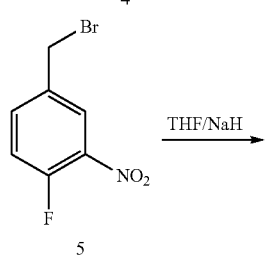
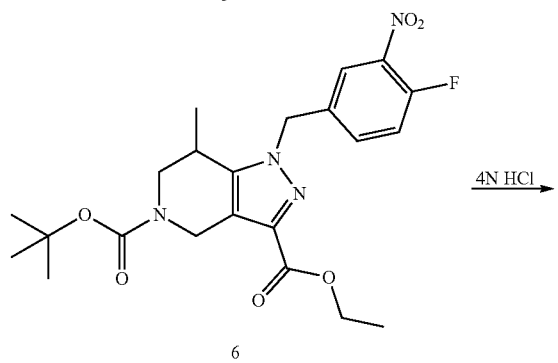
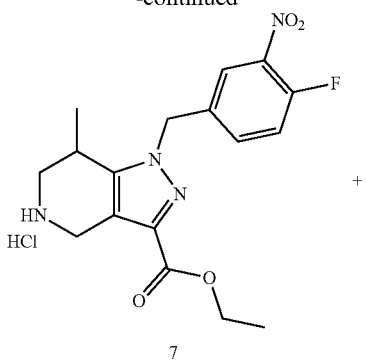
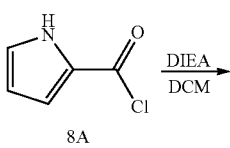
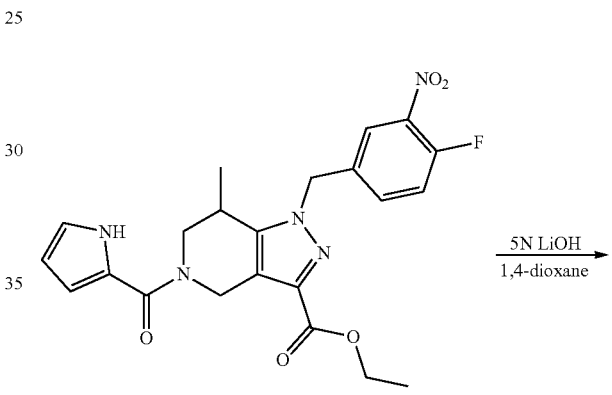
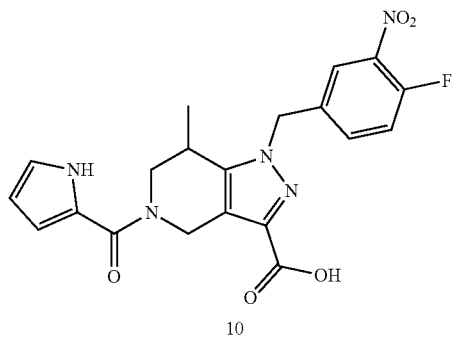
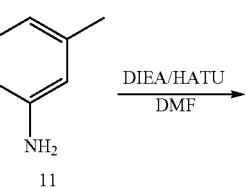

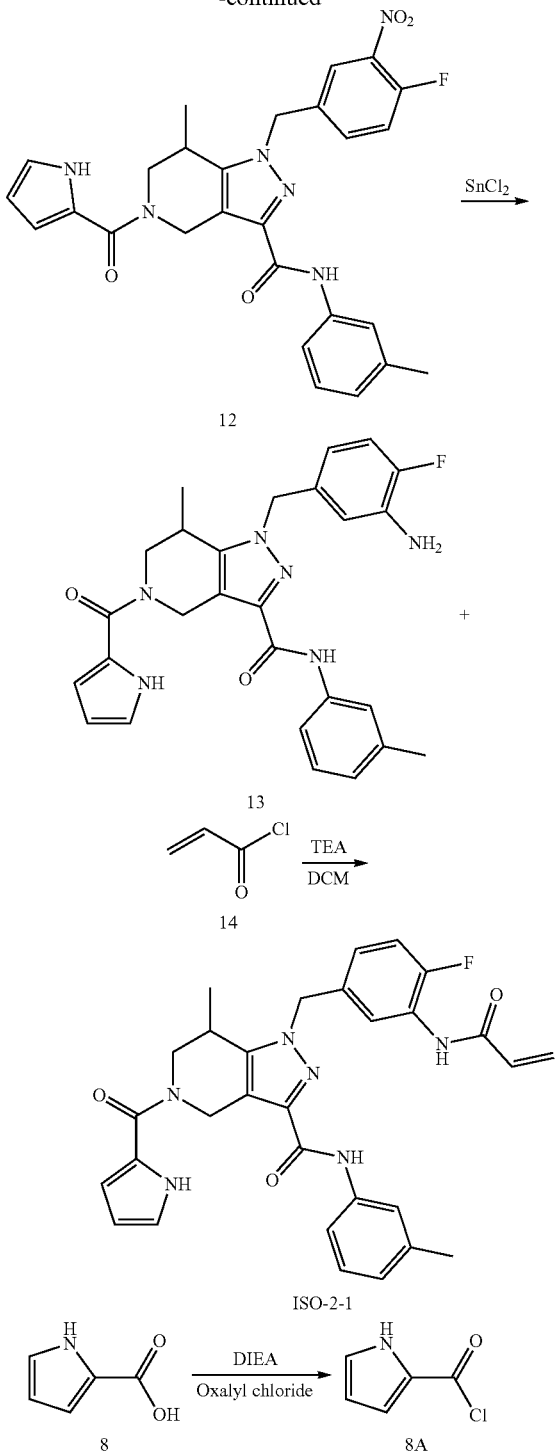

residue was purified by silica gel column chromatography (petroleum ether:ethyl acetate=20:1) to afford the compound as light yellow oil (30.4 g, 28%). MS m/z 214.23[M+H]$^+$.

Tert-butyl 3-(2-ethoxy-2-oxoacetyl)-5-methyl-4-oxopiperidine-1-carboxylate (3) To a solution of tert-butyl 3-methyl-4-oxopiperidine-1-carboxylate (2) (30.4 g, 0.14 mol) in anhydrous THF (350 mL) was added LDA (2M, 84 mL) dropwise at −78° C. under nitrogen atmosphere. The mixture was stirred at −78° C. for 1 h and diethyl oxalate (20.46 g, 0.14 mol) was added into the reaction solution. The resulting mixture was allowed to warm up to room temperature and stirred for 2 h. The mixture was neutralized with 1 N HCl and extracted with ethyl acetate. The organic layer was washed with brine, dried over Na$_2$SO$_4$, concentrated under reduced pressure and the residue was purified by silica gel chromatography (petroleum ether:ethyl acetate=10:1) to afford the compound as a yellow oil (20 g, 45.6%). MS m/z 314.15[M+H]$^+$.

5-(tert-butyl) 3-ethyl 7-methyl-1,4,6,7-tetrahydro-5H-pyrazolo[4,3-c]pyridine-3,5-dicarboxylate (4) To a solution of tert-butyl 3-(2-ethoxy-2-oxoacetyl)-5-methyl-4-oxopiperidine-1-carboxylate (3) (20 g, 63.8 mmol) in acetic acid (80 mL) was added hydrazine hydrate (9.6 g). After 2 h, the reaction mixture was concentrated under reduced pressure and the residue was diluted with water and saturated aqueous NaHCO$_3$ and then extracted with ethyl acetate. The combined organic layers were dried over Na$_2$SO$_4$, filtered, concentrated under reduced pressure and dried to provide compound (4) (16 g, 81%) as a pale yellow solid. MS m/z 310.17[M+H]$^+$. $^1$H NMR (400 MHz, DMSO) δ 13.35 (s, 1H), 4.42 (d, J=16.3 Hz, 2H), 4.30-4.23 (m, 2H), 4.03 (q, J=7.1 Hz, 1H), 3.75 (s, 1H), 2.94 (s, 2H), 1.42 (s, 9H), 1.28 (m, J=7.0 Hz, 3H), 1.18 (m, 3H).

5-(tert-butyl) 3-ethyl 1-(4-fluoro-3-nitrobenzyl)-7-methyl-1,4,6,7-tetrahydro-5H-pyrazolo[4,3-c]pyridine-3,5-dicarboxylate (6) To a solution of 5-(tert-butyl) 3-ethyl 7-methyl-1,4,6,7-tetrahydro-5H-pyrazolo[4,3-c]pyridine-3,5-dicarboxylate (4) (1.5 g, 4.85 mmol) in dry THF (20 mL) was added NaH (60% wt dispersion in mineral oil, 0.23 g, 5.82 mmol) with stirring under nitrogen. After 1 h, 4-(bromomethyl)-1-fluoro-2-nitrobenzene (1.13 g, 4.85 mmol) was added and the reaction mixture was stirred 4 h under nitrogen. The reaction mixture was quenched with water and the pH was adjusted to 6 with 1 N HCl. The mixture was diluted with brine and extracted with ethyl acetate. The combined extracts were dried over Na$_2$SO$_4$, filtered and concentrated under reduced pressure. The residue was purified by silica gel chromatography (petroleum ether:ethyl acetate=5:1) to provide 5-(tert-butyl) 3-ethyl 1-(4-fluoro-3-nitrobenzyl)-7-methyl-1,4,6,7-tetrahydro-5H-pyrazolo[4,3-c]pyridine-3,5-dicarboxylate (0.91 g, 40.6%) as light yellow solid. MS m/z 463.39[M+H]$^+$.

Ethyl 1-(4-fluoro-3-nitrobenzyl)-7-methyl-4,5,6,7-tetrahydro-1H-pyrazolo[4,3-c]pyridine-3-carboxylate hydrochloride (7) To a round-bottom flask containing 5-(tert-butyl) 3-ethyl 1-(4-fluoro-3-nitrobenzyl)-7-methyl-1,4,6,7-tetrahydro-5H-pyrazolo[4,3-c]pyridine-3,5-dicarboxylate (6) (0.91 g, 2 mmol) was added HCl (4 N in ethyl acetate, 5 mL). The resulting clear solution was stirred at room temperature for 3 h. The reaction mixture was concentrated under reduced pressure and the resulting residue was dried to provide ethyl 1-(4-fluoro-3-nitrobenzyl)-7-methyl-4,5,6,7-tetrahydro-1H-pyrazolo[4,3-c]pyridine-3-carboxylate hydrochloride (0.78 g, 100%) as a yellow solid.

1H-pyrrole-2-carbonyl chloride (8A) To a solution of 1H-pyrrole-2-carboxylic acid (8)(0.3 g) in DCM (15 mL) was added oxalyl chloride (0.28 mL) and a drop of DMF at Tert-butyl 3-methyl-4-oxopiperidine-1-carboxylate (2) To a solution of tert-butyl 4-oxopiperidine-1-carboxylate (1) (100 g, 0.5 mol) in anhydrous THF (1000, mL) was added LDA (300 mL) dropwise at −78° C. under nitrogen atmosphere. After 1 h, MeI (70.9 g, 0.5 mol) was added to the same temperature and then the mixture was stirred at room temperature for another 3 h. The mixture was quenched with saturated NH$_4$Cl solution and was portioned between ethyl acetate and water. The organic layer was washed with brine, dried over Na$_2$SO$_4$, and concentrated to give orange oil. The 0° C. The resulting clear solution was stirred at room temperature for 3 h. The reaction mixture was concentrated under reduced pressure. The solvent was distilled off under reduced pressure from the reaction mixture, and the residue was subjected to an azeotropic distillation treatment with toluene. The crude product of 1H-2-pyrrolecarbonyl chloride (0.35 g) was obtained as a brown crystalline product which was used directly in the next step.

Ethyl 1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylate (9) To a solution of ethyl 1-(4-fluoro-3-nitrobenzyl)-7-methyl-4,5,6,7-tetrahydro-1H-pyrazolo[4,3-c]pyridine-3-carboxylate hydrochloride (7) (0.8 g, 2.5 mmol) in DCM (10 mL) was added DIEA (0.65 g, 6.25 mmol) and 1H-pyrrole-2-carbonyl chloride (0.31 g, 3 mmol) at 0° C. for 10 min. The reaction mixture was diluted with water and saturated aqueous NaHCO$_3$ and extracted with two portions of DCM. The organic layer was washed with brine, dried over Na$_2$SO$_4$, concentrated under reduced pressure and the residue was purified by silica gel chromatography (petroleum ether:ethyl acetate=3:1) to afford the compound as a yellow solid (0.8 g, 73%). MS m/z 456.30[M+H]$^+$.

1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylic acid (10) To a solution of ethyl 1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylate (9) (0.8 g, 1.76 mmol) in 1,4-dioxane (5 mL) was added 5 N LiOH (5 mL). The clear solution was stirred at room temperature for 1 h. The reaction mixture was added water and pH was adjusted to 6 with 1 N HCl. The resulting precipitate was collected by filtration and dried on a lyophilizer overnight to provide 1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylic acid (0.7 g, 92%) as a white solid. MS m/z 428.19[M+H]$^+$.

5-((1H-pyrrol-2-yl)methyl)-1-(4-fluoro-3-nitrobenzyl)-7-methyl-N-(m-tolyl)-4,5,6,7-tetrahydro-1H-pyrazolo[4,3-c]pyridine-3-carboxamide (12) To a solution of 1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylic acid (10) (0.32 g, 0.75 mmol) in DMF (5 mL) were added m-toluidine (0.1 g, 0.9 mmol), HATU (0.43 g, 1.125 mmol) and DIEA (0.2 g, 1.5 mmol). The mixture was stirred at room temperature under nitrogen. After 1 h, the reaction mixture was added water and the resulting precipitate was collected by filtration and dried on a lyophilizer overnight to provide compound (12)(0.36 g, 95%) as a white solid. MS m/z 517.20[M+H]$^+$.

1-(3-amino-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) To a solution of 5-((1H-pyrrol-2-yl)methyl)-1-(4-fluoro-3-nitrobenzyl)-7-methyl-N-(m-tolyl)-4,5,6,7-tetrahydro-1H-pyrazolo[4,3-c]pyridine-3-carboxamide (12) (0.36 g, 0.7 mmol) in ethyl acetate/methanol (4/1)(10 mL) was added stannous chloride (1.12 g, 5.6 mmol). The resulting mixture was heated at 80° C. overnight. The reaction mixture was added DCM and the pH was adjusted to 8 with saturated aqueous NaHCO$_3$ and extracted with DCM. The organic layer was washed with brine, dried over Na$_2$SO$_4$, concentrated under reduced pressure and the residue was purified by silica gel chromatography (DCM:MeOH=50:1) to afford the compound as a white solid (0.3 g, 88%). MS m/z 487.28[M+H]$^+$.

1-(3-amino-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-1) To a solution of 1-(3-acrylamido-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) (0.3 g, 0.62 mmol) in DCM (10 mL) was added TEA (0.19 g, 1.86 mmol) and acryloyl chloride (0.17 g, 1.86 mmol) at 0° C. for 10 min. The reaction mixture was diluted with water and saturated aqueous NaHCO$_3$ and extracted with DCM. The organic layer was washed with brine, dried over Na$_2$SO$_4$, concentrated under reduced pressure and the residue was purified by silica gel chromatography (DCM:MeOH=20:1) to afford the compound as a white solid (86 mg, 26%). MS m/z 541.3[M+H]$^+$. $^1$H NMR (400 MHz, DMSO) δ 11.53 (s, 1H), 9.98 (s, 1H), 9.84 (s, 1H), 7.98 (d, J=5.9 Hz, 1H), 7.68 (s, 1H), 7.57 (d, J=8.3 Hz, 1H), 7.26 (m, 1H), 7.19 (t, J=8.0 Hz, 1H), 6.95 (m, 1H), 6.91 (m, 2H), 6.60 (m, 2H), 6.26 (dd, J=17.0, 1.9 Hz, 1H), 6.16 (m, 1H), 5.77 (dd, J=10.4, 2.2 Hz, 1H), 5.45 (q, J=16.4 Hz, 2H), 5.30 (d, J=16.4 Hz, 1H), 4.65 (br, 1H), 4.36 (d, J=11.1 Hz, 1H), 3.41 (m, 1H), 3.20 (m, 1H), 2.29 (s, 3H), 1.13 (t, J=8.9 Hz, 3H).

The synthesis of 1-(3-(acrylamidomethyl)-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-2)

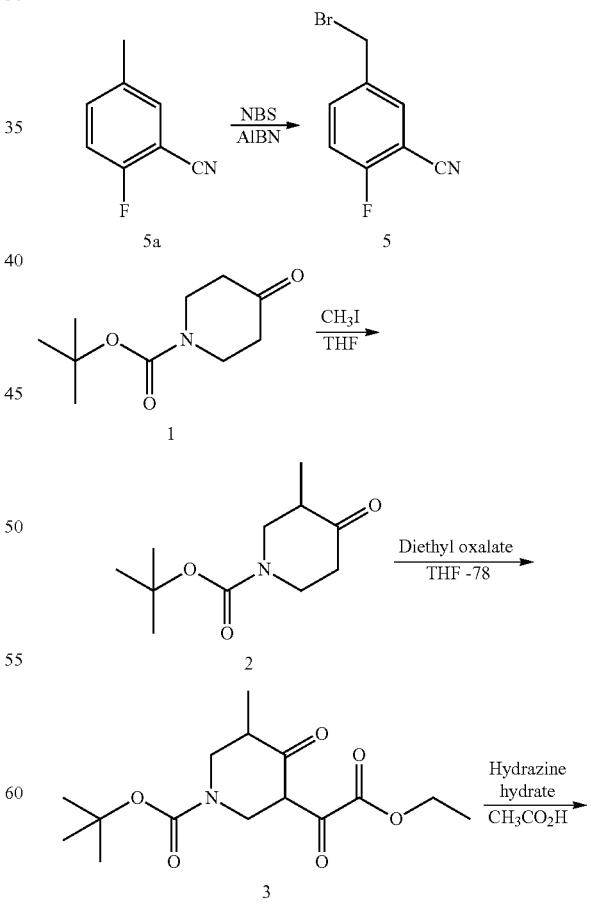

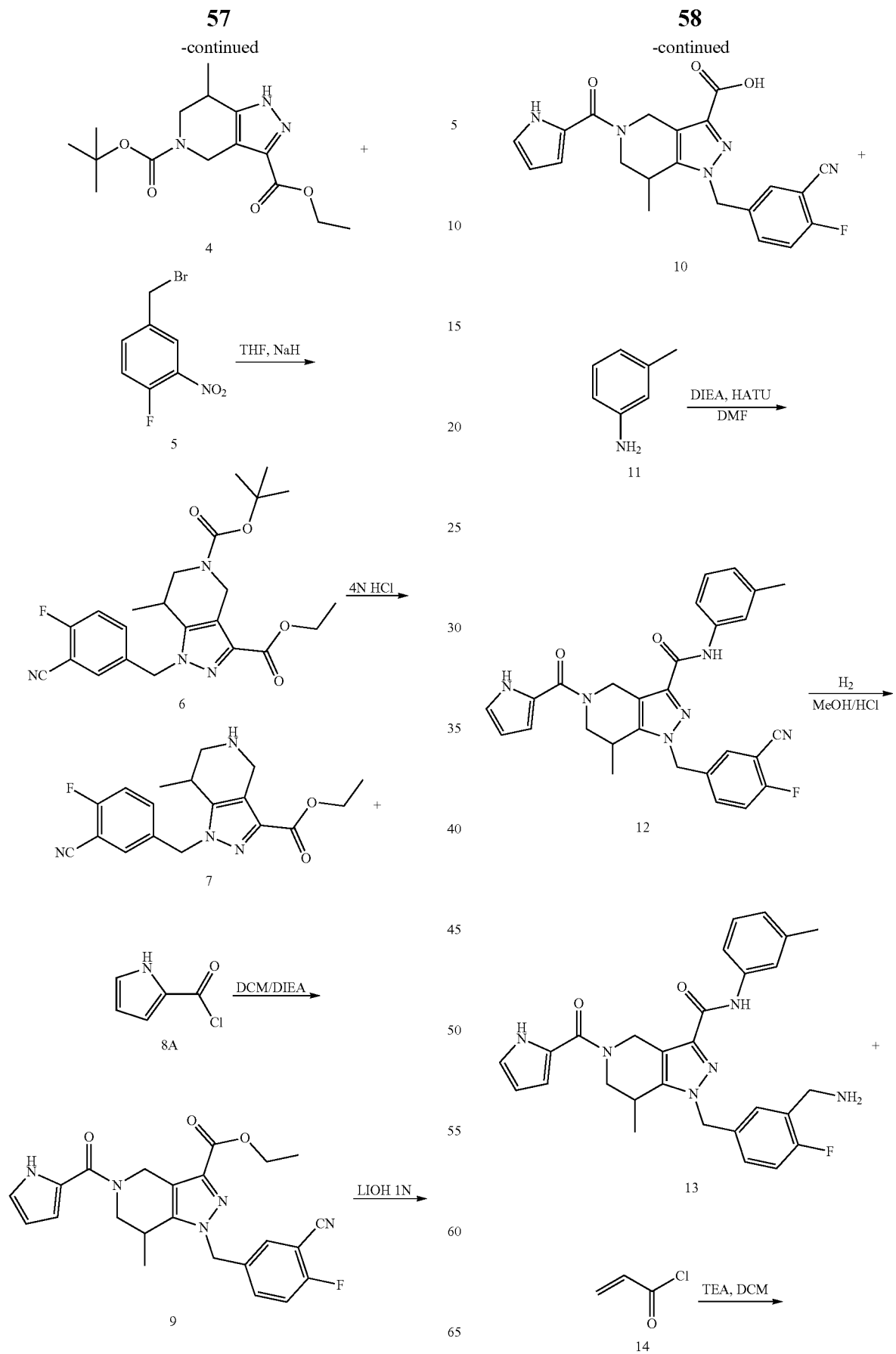

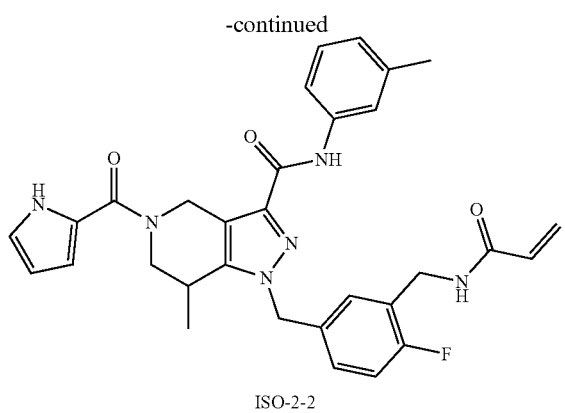

ISO-2-2

5-(tert-butyl)3-ethyl1-(3-cyano-4-fluorobenzyl)-7-methyl-1,4,6,7-tetrahydro-5H-pyrazolo[4,3-c]pyridine-3,5-dicarboxylate (6) To a solution of 5-(tert-butyl) 3-ethyl 7-methyl-1,4,6,7-tetrahydro-5H-pyrazolo[4,3-c]pyridine-3,5-dicarboxylate (4) (0.8 g, 2.6 mmol) in dry THF (20 mL) was added NaH (60% wt dispersion in mineral oil, 0.2 g, 5 mmol) with stirring under nitrogen. After 1 h, 5-(bromomethyl)-2-fluorobenzonitrile (0.7 g, 3.3 mmol) was added and the reaction mixture was stirred 4 h under nitrogen. The reaction mixture was quenched with water and the pH was adjusted to 6 with 1 N HCl. The mixture was diluted with brine and extracted with ethyl acetate. The combined extracts were dried over $Na_2SO_4$, filtered and concentrated under reduced pressure. The residue was purified by silica gel chromatography (petroleum ether:ethyl acetate=5:1) to provide 5-(tert-butyl) 3-ethyl 1-(3-cyano-4-fluorobenzyl)-7-methyl-1,4,6,7-tetrahydro-5H-pyrazolo[4,3-c]pyridine-3,5-dicarboxylate (1.4 g, 95%) as a light yellow solid. MS m/z 442.2[M+H]$^+$.

ethyl1-(3-cyano-4-fluorobenzyl)-7-methyl-4,5,6,7-tetrahydro-1H-pyrazolo[4,3-c]pyridine-3-carboxylate (7) To a round-bottom flask containing 5-(tert-butyl) 3-ethyl 1-(3-cyano-4-fluorobenzyl)-7-methyl-1,4,6,7-tetrahydro-5H-pyrazolo[4,3-c]pyridine-3,5-dicarboxylate (6) (1.4 g, 2 mmol) was added HCl (4 N in ethyl acetate, 5 mL). The resulting clear solution was stirred at room temperature for 3 h. The reaction mixture was quenched with water and the pH was adjusted to 7 with $NaHCO_3$. The mixture was diluted with brine and extracted with DCM. The combined extracts were dried over $Na_2SO_4$, filtered and concentrated under reduced pressure and the resulting residue was dried to provide ethyl 1-(3-cyano-4-fluorobenzyl)-7-methyl-4,5,6,7-tetrahydro-1H-pyrazolo[4,3-c]pyridine-3-carboxylate (0.8 g, 60%) as a yellow solid. MS m/z 343.15[M+H]$^+$.

ethyl1-(3-cyano-4-fluorobenzyl)-7-methyl-5-(1H-pyrrole-2-carbonyl)-4,5,6,7-tetrahydro-1H-pyrazolo[4,3-c]pyridine-3-carboxylate (9) To a solution of ethyl 1-(3-cyano-4-fluorobenzyl)-7-methyl-4,5,6,7-tetrahydro-1H-pyrazolo[4,3-c]pyridine-3-carboxylate (7) (0.8 g, 2.5 mmol) in DCM (10 mL) was added DIEA (0.65 g, 6.25 mmol) and 1H-pyrrole-2-carbonyl chloride (0.31 g, 3 mmol) at 0° C. for 10 min. The reaction mixture was diluted with water and saturated aqueous $NaHCO_3$ and extracted with two portions of DCM. The organic layer was washed with brine, dried over $Na_2SO_4$, concentrated under reduced pressure and the residue was purified by silica gel chromatography (petroleum ether:ethyl acetate=2:1) to afford the compound as a yellow solid (0.8 g, 70%). MS m/z 436.17[M+H]$^+$.

1-(3-cyano-4-fluorobenzyl)-7-methyl-5-(1H-pyrrole-2-carbonyl)-4,5,6,7-tetrahydro-1H-pyrazolo[4,3-c]pyridine-3-carboxylic acid (10) To a solution of ethyl1-(3-cyano-4-fluorobenzyl)-7-methyl-5-(1H-pyrrole-2-carbonyl)-4,5,6,7-tetrahydro-1H-pyrazolo[4,3-c]pyridine-3-carboxylate (9) (0.8 g, 1.84 mmol) in 1,4-dioxane (5 mL) was added 5 N LiOH (5 mL). The clear solution was stirred at room temperature for 1 h. The reaction mixture was added water and pH was adjusted to 6 with 1 N HCl. The resulting precipitate was collected by filtration and dried on a lyophilizer overnight to provide 1-(3-cyano-4-fluorobenzyl)-7-methyl-5-(1H-pyrrole-2-carbonyl)-4,5,6,7-tetrahydro-1H-pyrazolo[4,3-c]pyridine-3-carboxylic acid (0.7 g, 89%) as a white solid. MS m/z 408.14[M+H]$^+$.

1-(3-cyano-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (12) To a solution of 1-(3-cyano-4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.72 g, 1.75 mmol) in DMF (5 mL) were added m-toluidine (0.4 g, 3.7 mmol), HATU (0.8 g, 2.1 mmol) and DIEA (0.4 g, 3 mmol). The mixture was stirred at room temperature under nitrogen. After 1 h, the reaction mixture was added water and the resulting precipitate was collected by filtration and dried on a lyophilizer overnight to provide compound (12)(0.85 g, 99%) as a white solid. MS m/z 497.20[M+H]$^+$.

1-(3-(aminomethyl)-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) To a solution of 1-(3-cyano-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (12) (0.36 g, 0.7 mmol) in methanol (10 mL) was added Hydrochloric acid (2 mL) and Pd/C (0.2 g). The resulting mixture was stirred at room temperature overnight under H2. The organic layer was concentrated under reduced pressure and the residue was purified by silica gel chromatography (DCM:MeOH=50:1) to afford the compound as a white solid (0.3 g, 88%). MS m/z 501.23[M+H]$^+$.

1-(3-(acrylamidomethyl)-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-2) To a solution of 1-(3-(aminomethyl)-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) (0.2 g, 0.4 mmol) in DCM (10 ml) was added TEA (0.13 g, 1.2 mmol) and acryloyl chloride (0.04 g, 0.44 mmol) at 0° C. for 10 min. The reaction mixture was diluted with water and saturated aqueous $NaHCO_3$ and extracted with DCM. The organic layer was washed with brine, dried over $Na_2SO_4$, concentrated under reduced pressure and the residue was purified by silica gel chromatography (DCM:MeOH=20:1) to afford the compound as a white solid (112 mg, 43%). MS m/z 555.24[M+H]$^+$. $^1$H NMR (400 MHz, DMSO) δ 11.53 (s, 1H), 9.81 (s, 1H), 8.60 (m, 1H), 7.68 (s, 1H), 7.56 (d, J=7.9 Hz, 1H), 7.24-7.08 (m, 4H), 6.91 (m, 2H), 6.59 (m, 1H), 6.27-6.13 (m, 2H), 6.04 (dd, J=17.1, 2.1 Hz, 1H), 5.51 (dd, J=10.1, 2.1 Hz, 1H), 5.41 (q, J=16.2 Hz, 2H), 5.26 (d, J=16.5 Hz, 1H), 4.63 (br, 1H), 4.35 (m, 3H), 3.30 (s, 1H), 3.16-3.07 (m, 1H), 2.29 (s, 3H), 1.07 (d, J=6.8 Hz, 3H).

The synthesis of 1-(3-acrylamido-4-fluorobenzyl)-N-(3((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (ISO-2-3)
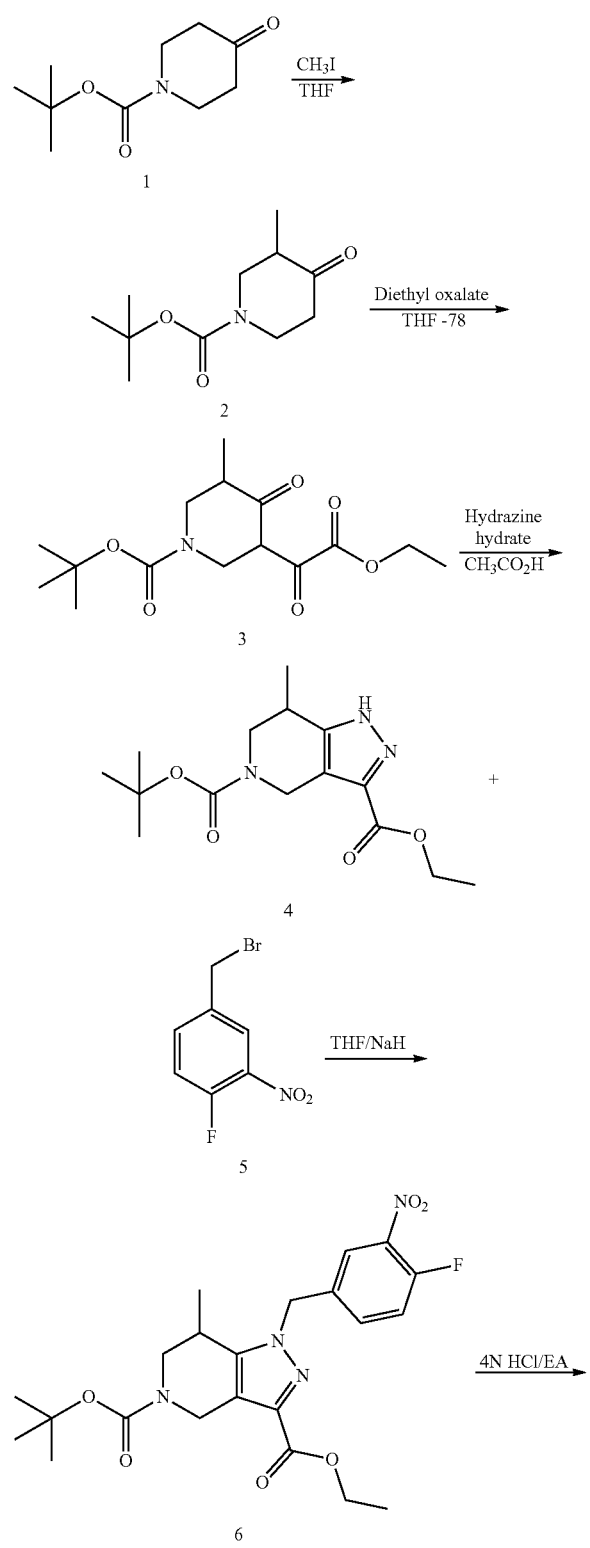
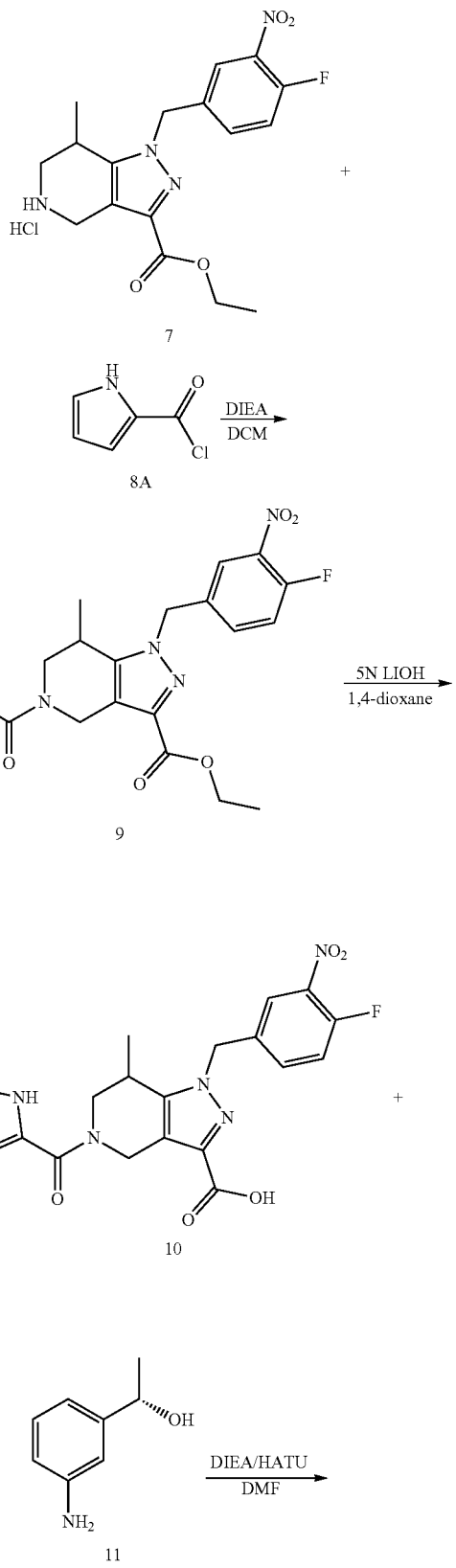

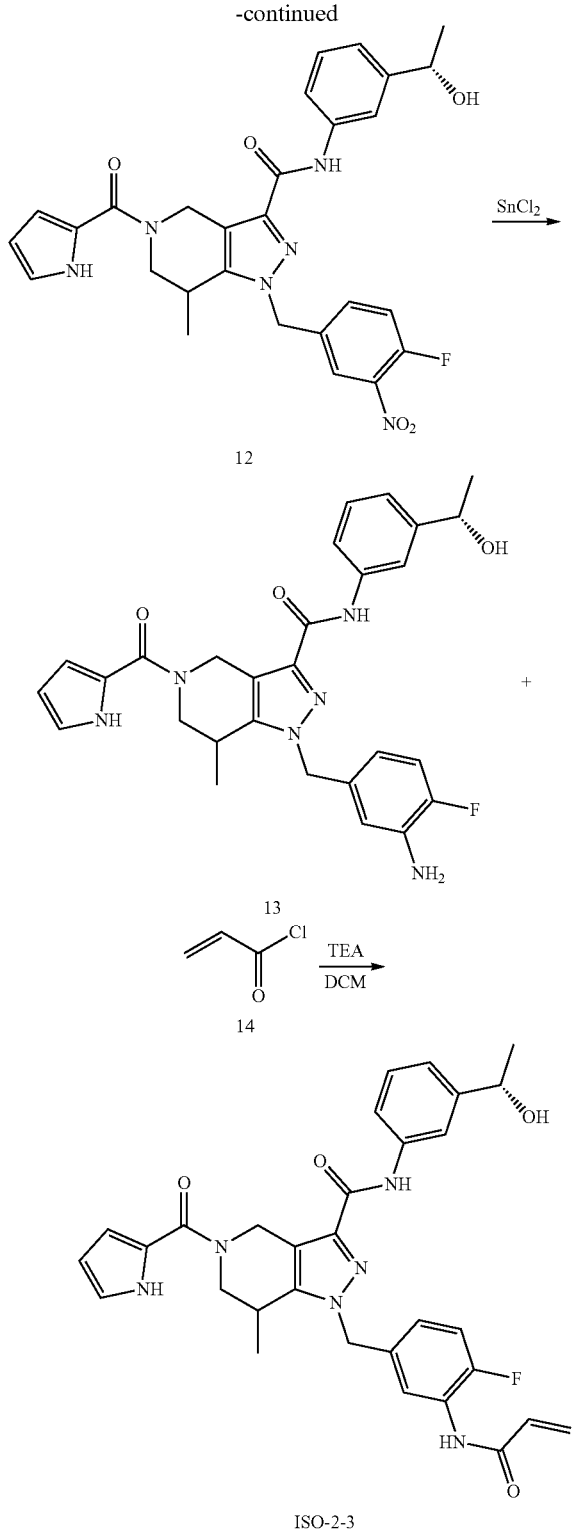

(0.12 g, 0.9 mmol), HATU (0.43 g, 1.125 mmol) and DIEA (0.2 g, 1.5 mmol). The mixture was stirred at room temperature under nitrogen. After 1 h, the reaction mixture was added with water and the resulting precipitate was collected by filtration and dried on a lyophilizer overnight to provide compound (12) (0.38 g, 93%) as a white solid. MS m/z 547.22[M+H]$^+$.

1-(3-amino-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (13) To a solution of 5-((1H-pyrrol-2-yl)methyl)-1-(4-fluoro-3-nitrobenzyl)-N-(3-((5)-1-hydroxyethyl)phenyl)-7-methyl-4,5,6,7-tetrahydro-1H-pyrazolo[4,3-c]pyridine-3-carboxamide (12) (0.38 g, 0.7 mmol) in EA/methanol (4/1)(10 mL) was added stannous chloride (1.1 g, 5.6 mmol). The resulting mixture was heated at 80° C. overnight. The reaction mixture was added DCM and the pH was adjusted to 8 with saturated aqueous NaHCO$_3$ and extracted with DCM. The organic layer was washed with brine, dried over Na$_2$SO$_4$, concentrated under reduced pressure and the residue was purified by silica gel chromatography (DCM:MeOH=50:1) to afford the compound (13) as a white solid (0.325 g, 90%). MS m/z 517.28[M+H]$^+$.

1-(3-acrylamido-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (ISO-2-3) To a solution of 1-(3-amino-4-fluorobenzyl)-N-(3-((5)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (13)(0.16 g, 0.31 mmol) in DCM (5 mL) was added TEA (63 mg, 0.62 mmol) and acryloyl chloride (42.2 g, 46.5 mmol) at 0° C. for 10 min. The reaction mixture was diluted with water and saturated aqueous NaHCO$_3$ and extracted with two portions of DCM. The organic layer was washed with brine, dried over Na$_2$SO$_4$, concentrated under reduced pressure and the residue was purified by silica gel chromatography (DCM:MeOH=20:1) to afford the compound as a white solid (35 mg, 20%). MS m/z 571.17[M+H]$^+$. $^1$H NMR (400 MHz, DMSO) δ 11.53 (s, 1H), 9.98 (s, 1H), 9.88 (s, 1H), 7.97 (d, J=6.0 Hz, 1H), 7.83 (s, 1H), 7.63 (m, 1H), 7.30-7.18 (m, 2H), 7.05 (d, J=7.6 Hz, 1H), 6.97 (m, 1H), 6.91 (m, 1H), 6.66-6.53 (m, 2H), 6.26 (dd, J=16.8, 2.0 Hz, 1H), 6.17 (m, 1H), 5.75 (m, 1H), 5.43 (q, J=16.0 Hz, 2H), 5.30 (d, J=16.4 Hz, 1H), 5.13 (d, J=4.1 Hz, 1H), 4.74-4.59 (m, 2H), 4.36 (d, J=11.3 Hz, 1H), 3.50-3.41 (m, 1H), 3.25-3.11 (m, 1H), 1.31 (d, J=6.4 Hz, 3H), 1.12 (d, J=6.8 Hz, 3H).

The synthesis of N-(3-acrylamidophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-4)

5-((1H-pyrrol-2-yl)methyl)-1-(4-fluoro-3-nitrobenzyl)-N-(3-((S)-1-hydroxyethyl)phenyl)-7-methyl-4,5,6,7-tetrahydro-1H-pyrazolo[4,3-c]pyridine-3-carboxamide (12) To a solution of 1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylic acid (10) (0.32 g, 0.75 mmol) in DMF (5 mL) were added (S)-1-(3-aminophenyl)ethan-1-ol (11)

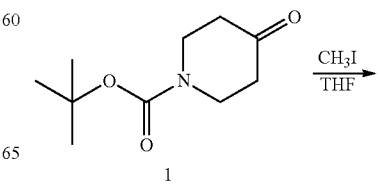

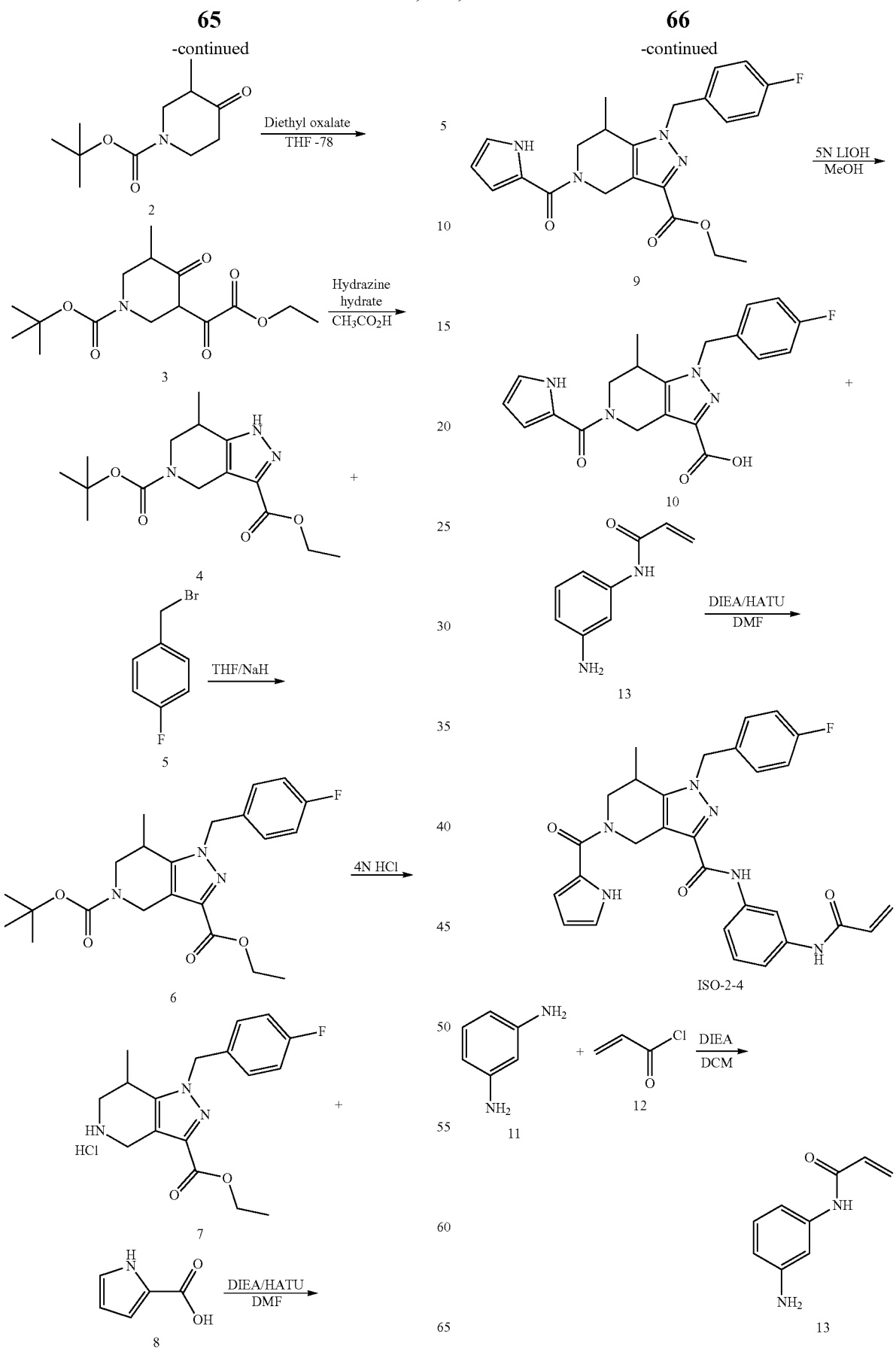

5-(tert-butyl) 3-ethyl 1-(4-fluorobenzyl)-7-methyl-1,4,6,7-tetrahydro-5H-pyrazolo[4,3-c]pyridine-3,5-dicarboxylate (6) To a solution of 5-(tert-butyl) 3-ethyl 7-methyl-1,4,6,7-tetrahydro-5H-pyrazolo[4,3-c]pyridine-3,5-dicarboxylate (4) (2 g, 6.46 mmol) in dry THF (30 mL) was added NaH (60% wt dispersion in mineral oil, 0.31 g, 7.75 mmol) with stirring under nitrogen. After 1 h, 1-(bromomethyl)-4-fluorobenzene (1.5 g, 6.46 mmol) was added and the reaction mixture was stirred under nitrogen for 4 h. The reaction mixture was quenched with water and the pH was adjusted to 6 with 1 N HCl. The mixture was diluted with brine and extracted with ethyl acetate. The combined extracts were dried over $Na_2SO_4$, filtered and concentrated under reduced pressure. The residue was purified by silica gel chromatography (petroleum ether:ethyl acetate=5:1) to afford 5-(tert-butyl) 3-ethyl 1-(4-fluorobenzyl)-7-methyl-1,4,6,7-tetrahydro-5H-pyrazolo[4,3-c]pyridine-3,5-dicarboxylate (1.05 g, 34%) as a light yellow solid. MS m/z 418.2[M+H]$^+$.

Ethyl 1-(4-fluoro-3-nitrobenzyl)-7-methyl-4,5,6,7-tetrahydro-1H-pyrazolo[4,3-c]pyridine-3-carboxylate hydrochloride (7) To a round-bottom flask containing 5-(tert-butyl) 3-ethyl 1-(4-fluorobenzyl)-7-methyl-1,4,6,7-tetrahydro-5H-pyrazolo[4,3-c]pyridine-3,5-dicarboxylate (6) (2.52 g, 6.04 mmol) was added HCl (4 N in ethyl acetate, 20 mL). The resulting clear solution was stirred at room temperature for 3 h. The reaction mixture was concentrated under reduced pressure and the resulting residue was dried under high vacuum to afford ethyl 1-(4-fluoro-3-nitrobenzyl)-7-methyl-4,5,6,7-tetrahydro-1H-pyrazolo[4,3-c]pyridine-3-carboxylate hydrochloride (2.13 g, 100%) as a yellow solid.

Ethyl 1-(4-fluorobenzyl)-7-methyl-5-(1H-pyrrole-2-carbonyl)-4,5,6,7-tetrahydro-1H-pyrazolo[4,3-c]pyridine-3-carboxylate (9) To a solution of ethyl 1-(4-fluoro-3-nitrobenzyl)-7-methyl-4,5,6,7-tetrahydro-1H-pyrazolo[4,3-c]pyridine-3-carboxylate hydrochloride (7)(0.35 g, 1 mmol) in DMF (10 mL) were added 1H-pyrrole-2-carboxylic acid (0.12 g, 1.1 mmol), HATU (0.57 g, 1.5 mmol) and DIEA (0.39 g, 3 mmol). The mixture was stirred at room temperature under nitrogen. After 1 h, the reaction mixture was added with water and the resulting precipitate was collected by filtration and dried on a lyophilizer overnight to afford compound (9) (0.29 g, 70%) as a white solid. MS m/z 411.32[M+H]$^+$.

1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) To a solution of ethyl 1-(4-fluorobenzyl)-7-methyl-5-(1H-pyrrole-2-carbonyl)-4,5,6,7-tetrahydro-1H-pyrazolo[4,3-c]pyridine-3-carboxylate (9) (0.2 g, 0.49 mmol) in MeOH (3 mL) was added 5N LiOH (1 mL). The clear solution was stirred at room temperature for 1 h. The reaction mixture was added water and pH was adjusted to 6 with 1 N HCl. The resulting precipitate was collected by filtration and dried on a lyophilizer overnight to afford 1-(4-fluorobenzyl)-7-methyl-5-(1H-pyrrole-2-carbonyl)-4,5,6,7-tetrahydro-1H-pyrazolo[4,3-c]pyridine-3-carboxylic acid (0.1 g, 53.5%) as a white solid. MS m/z 383.13[M+H]$^+$.

N-(3-aminophenyl)acrylamide (13) To a solution of benzene-1,3-diamine (11) (5.4 g, 50 mmol) in DCM (100) was added DIEA (13 g, 100 mmol) and acryloyl chloride (4.5 g, 50 mmol) at 0° C. for 10 min. The reaction mixture was diluted with water and saturated aqueous $NaHCO_3$ and extracted with two portions of DCM. The organic layer was washed with brine, dried over $Na_2SO_4$, concentrated under reduced pressure and the residue was purified by silica gel chromatography (DCM:MeOH=20:1) to afford the compound as a brown solid (2.4 g, 30%). MS m/z 163.08[M+H]$^+$. N-(3-acrylamidophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-4) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (38 mg, 0.1 mmol) in DMF (2 mL) were added N-(3-aminophenyl)acrylamide (18 mg, 0.11 mmol), HATU (57 mg, 0.15 mmol) and DIEA (26 mg, 0.2 mmol). The mixture was stirred at room temperature under nitrogen. After 1 h, the reaction mixture was diluted with water and extracted with DCM. The organic layer was washed with brine, dried over $Na_2SO_4$, concentrated under reduced pressure and the residue was purified by silica gel chromatography (DCM:MeOH=20:1) to afford the compound as a white solid (32 mg, 60.1%). MS m/z 527.85[M+H]$^+$. $^1$H NMR (400 MHz, DMSO) δ 11.53 (s, 1H), 10.16 (s, 1H), 9.99 (s, 1H), 8.23 (m, 1H), 7.54 (m, 1H), 7.37 (m, 1H), 7.31-7.12 (m, 5H), 6.91 (m, 1H), 6.58 (m, 1H), 6.47 (m, 1H), 6.26 (dd, J=16.8, 2.0 Hz, 1H), 6.18 (m, 1H), 5.73 (dd, J=16.0, 2.0 Hz, 1H), 5.45 (q, J=16.4 Hz, 2H), 5.32 (d, J=15.6 Hz, 1H), 4.78-4.58 (m, 1H), 4.35 (d, J=13.2 Hz, 1H), 3.38 (m, 1H), 3.22-3.10 (m, 1H), 1.09 (d, J=6.8 Hz, 3H).

The synthesis of N-(3-(2-chloroacetamido)phenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-5)

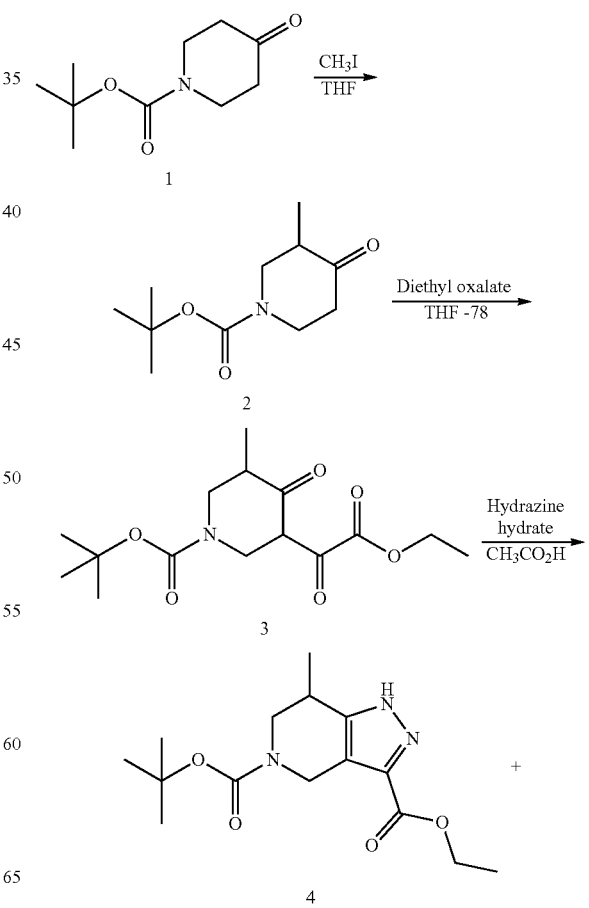

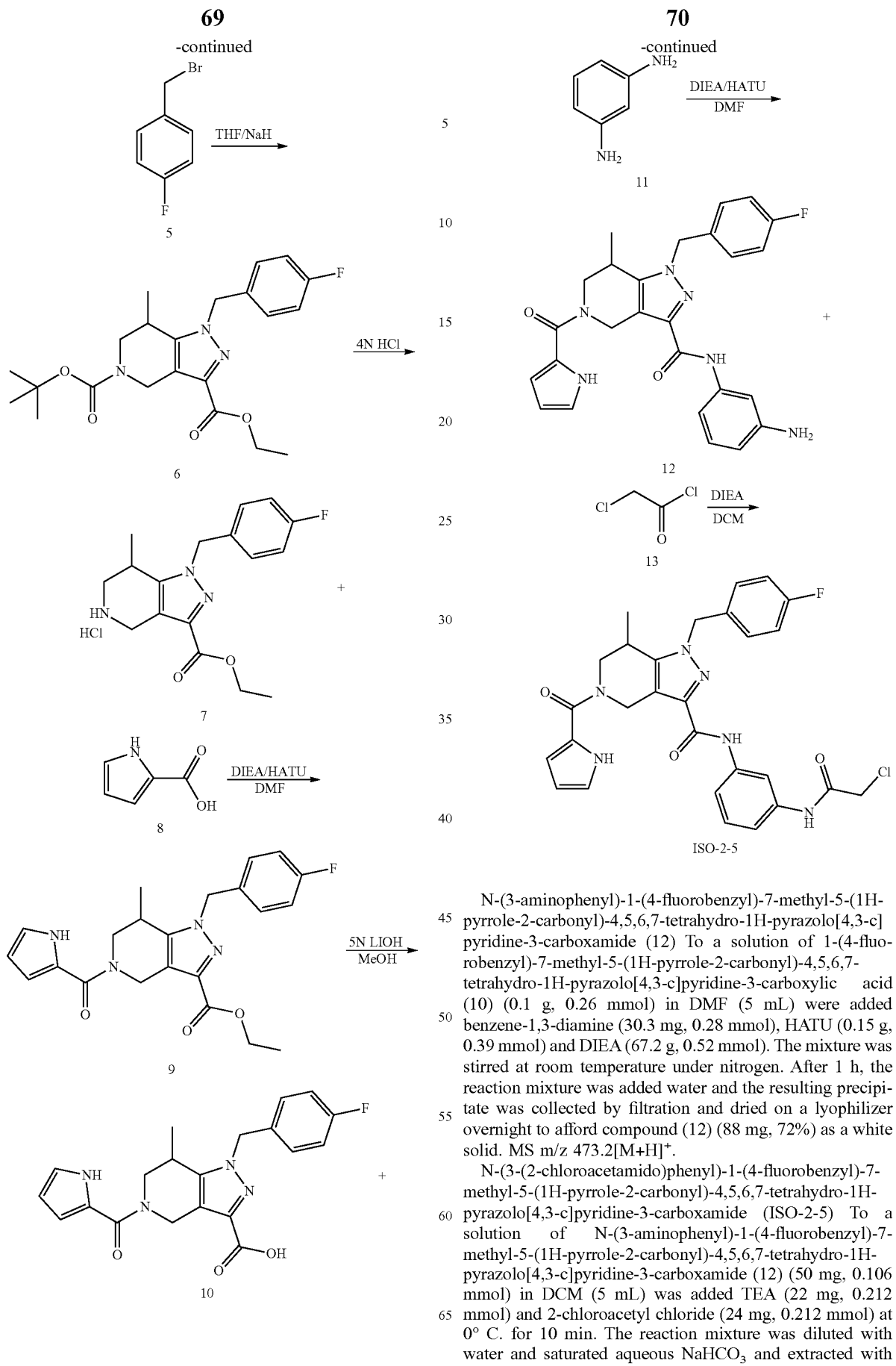

N-(3-aminophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.1 g, 0.26 mmol) in DMF (5 mL) were added benzene-1,3-diamine (30.3 mg, 0.28 mmol), HATU (0.15 g, 0.39 mmol) and DIEA (67.2 g, 0.52 mmol). The mixture was stirred at room temperature under nitrogen. After 1 h, the reaction mixture was added water and the resulting precipitate was collected by filtration and dried on a lyophilizer overnight to afford compound (12) (88 mg, 72%) as a white solid. MS m/z 473.2[M+H]$^+$.

N-(3-(2-chloroacetamido)phenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-5) To a solution of N-(3-aminophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) (50 mg, 0.106 mmol) in DCM (5 mL) was added TEA (22 mg, 0.212 mmol) and 2-chloroacetyl chloride (24 mg, 0.212 mmol) at 0° C. for 10 min. The reaction mixture was diluted with water and saturated aqueous NaHCO$_3$ and extracted with two portions of DCM. The organic layer was washed with brine, dried over Na₂SO₄, concentrated under reduced pressure and the residue was purified by silica gel chromatography (DCM:MeOH=20:1) to afford the compound as a white solid (20 mg, 35%). MS m/z 549.17 [M+H]⁺. ¹H NMR (400 MHz, DMSO) δ 11.52 (s, 1H), 10.36 (s, 1H), 10.02 (s, 1H), 8.18 (s, 1H), 7.42 (m, 2H), 7.31-7.14 (m, 5H), 6.91 (m, 1H), 6.58 (m, 1H), 6.18 (m, 1H), 5.45 (q, J=16.2 Hz, 2H), 5.31 (d, J=16.7 Hz, 1H), 4.69 (br, 1H), 4.35 (d, J=13.6 Hz, 1H), 4.26 (s, 2H), 3.47-3.34 (m, 1H), 3.17 (d, J=5.2 Hz, 1H), 1.09 (d, J=6.9 Hz, 3H).

The synthesis of N-(1-acryloylpiperidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-6)

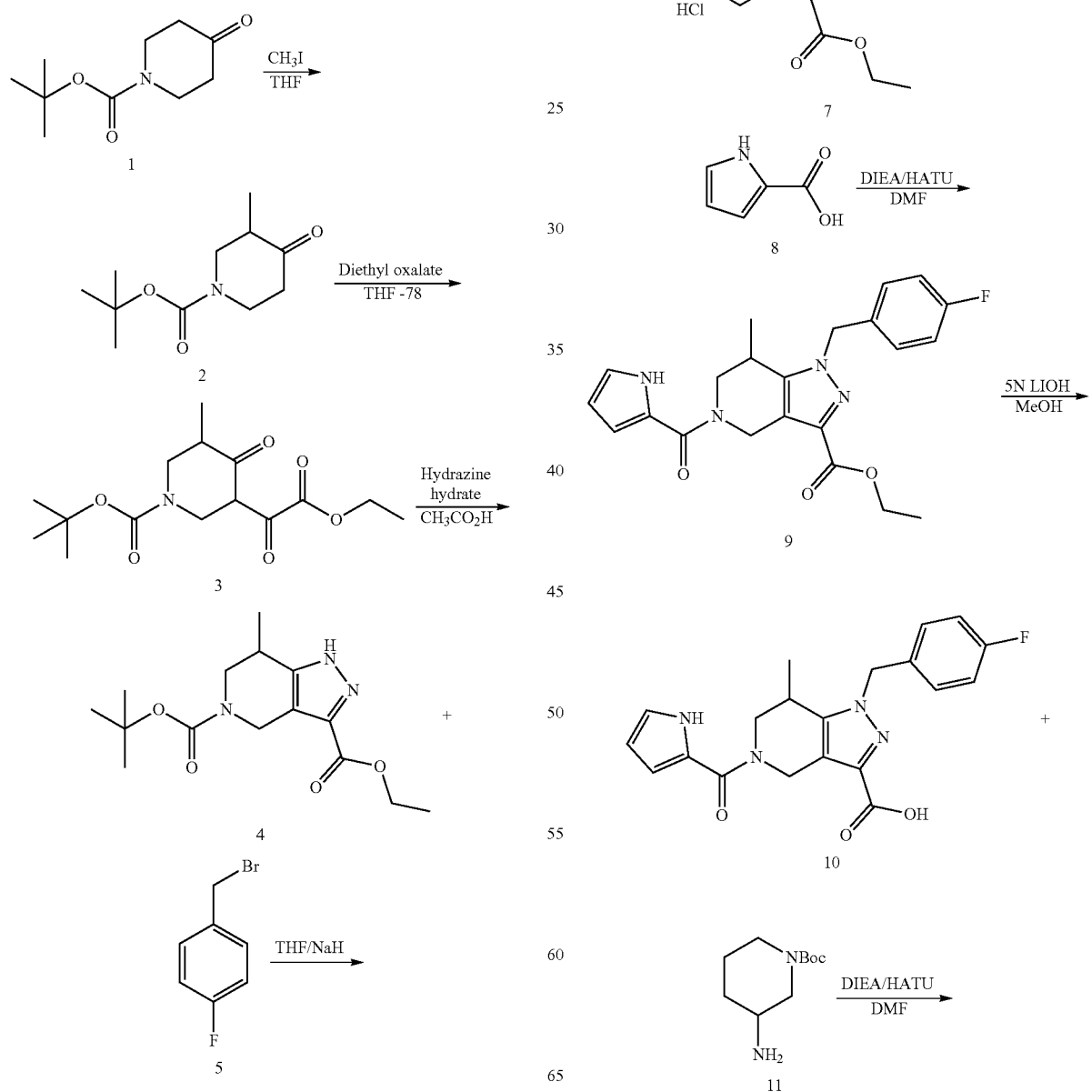

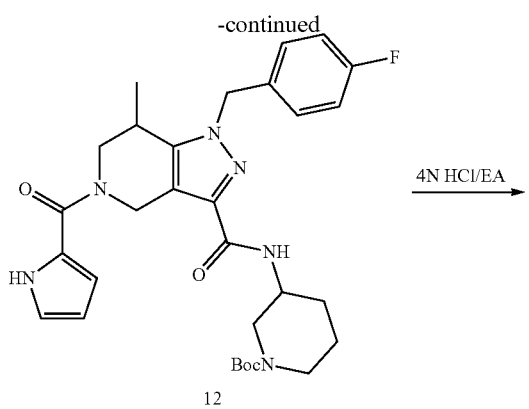

12

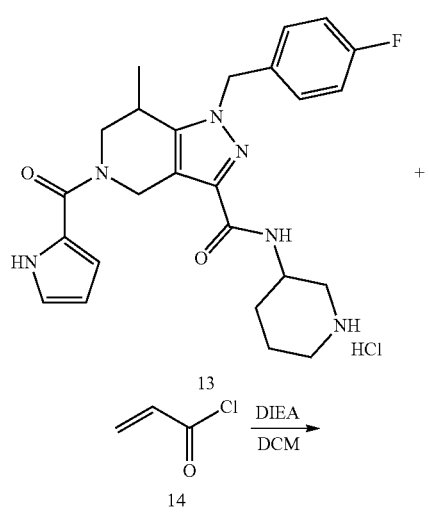

13

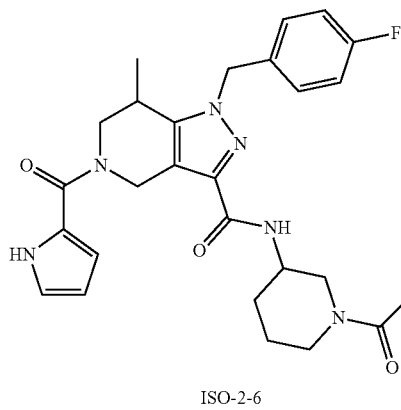

ISO-2-6

Tert-butyl 3-(1-(4-fluorobenzyl)-7-methyl-5-(1H-pyrrole-2-carbonyl)-4,5,6,7-tetrahydro-1H-pyrazolo[4,3-c]pyridine-3-carboxamido)piperidine-1-carboxylate (12) To a solution of 1-(4-fluoro-3-nitrobenzyl)-7-methyl-5-(1H-pyrrole-2-carbonyl)-4,5,6,7-tetrahydro-1H-pyrazolo [4,3-c]pyridine-3-carboxylic acid (10) (0.1 g, 0.26 mmol) in DMF (5 mL) were added tert-butyl 3-aminopiperidine-1-carboxylate (56 mg, 0.28 mmol), HATU (0.15 g, 0.39 mmol) and DIEA (67 mg, 0.52 mmol). The mixture was stirred at room temperature under nitrogen. After 1 h, the reaction mixture was added with water and the resulting precipitate was collected by filtration and dried on a lyophilizer overnight to afford compound (12) (0.1 g, 68%) as a white solid. MS m/z 565.2[M+H]$^+$.

1-(4-fluorobenzyl)-7-methyl-N-(piperidin-3-yl)-5-(1H-pyrrole-2-carbonyl)-4,5,6,7-tetrahydro-1H-pyrazolo[4,3-c]pyridine-3-carboxamide hydrochloride (13) To a round-bottom flask containing tert-butyl 3-(1-(4-fluorobenzyl)-7-methyl-5-(1H-pyrrole-2-carbonyl)-4,5,6,7-tetrahydro-1H-pyrazolo[4,3-c]pyridine-3-carboxamido)piperidine-1-carboxylate (12) (0.1 g, 0.18 mmol) was added HCl (4 N in ethyl acetate, 5 mL). The resulting solution was stirred at room temperature for 3 h. The reaction mixture was concentrated under reduced pressure and the resulting residue was dried to constant weight under high vacuum to afford 1-(4-fluorobenzyl)-7-methyl-N-(piperidin-3-yl)-5-(1H-pyrrole-2-carbonyl)-4,5,6,7-tetrahydro-1H-pyrazolo[4,3-c]pyridine-3-carboxamide hydrochloride (90 mg, 100%) as a yellow solid.

N-(1-acryloylpiperidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-6) To a solution of 1-(4-fluorobenzyl)-7-methyl-N-(piperidin-3-yl)-5-(1H-pyrrole-2-carbonyl)-4,5,6,7-tetrahydro-1H-pyrazolo [4,3-c]pyridine-3-carboxamide hydrochloride (13) (90 mg, 0.18 mmol) in DCM(5 ml) was added DIEA (70 mg, 0.54 mmol) and acryloyl chloride (32 mg, 0.36 mmol) at 0° C. for 10 min. The reaction mixture was diluted with water and saturated aqueous NaHCO$_3$ and extracted with DCM. The organic layer was washed with brine, dried over Na$_2$SO$_4$, concentrated under reduced pressure and the residue was purified by silica gel chromatography (DCM:MeOH=20:1) to afford the compound as a white solid (33.6 mg, 36%). MS m/z 519.6 [M+H]$^+$. $^1$H NMR (400 MHz, DMSO) δ 11.51 (s, 1H), 7.94 (br, 1H), 7.19 (m, 4H), 6.90 (m, 1H), 6.76 (br, 1H), 6.56 (s, 1H), 6.17 (m, 1H), 6.08 (d, J=16.0 Hz, 1H), 5.66 (dd, J=10.5, 2.3 Hz, 1H), 5.38 (q, J=16.4 Hz, 2H), 5.24 (d, J=16.3 Hz, 1H), 4.61 (m, 1H), 4.31 (m, 1H), 4.12 (m, 1H), 3.89 (m, 1H), 3.78 (s, 1H), 3.44-3.33 (m, 1H), 3.30-2.88 (m, 3H), 2.78 (m, 1H), 1.83 (m, 1H), 1.69 (m, 2H), 1.06 (d, J=6.3 Hz, 3H).

The synthesis of 1-(2-acrylamido-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo [4,3-c]pyridine-3-carboxamide (ISO-2-7)

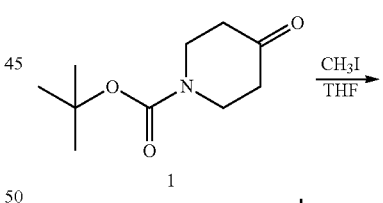

1

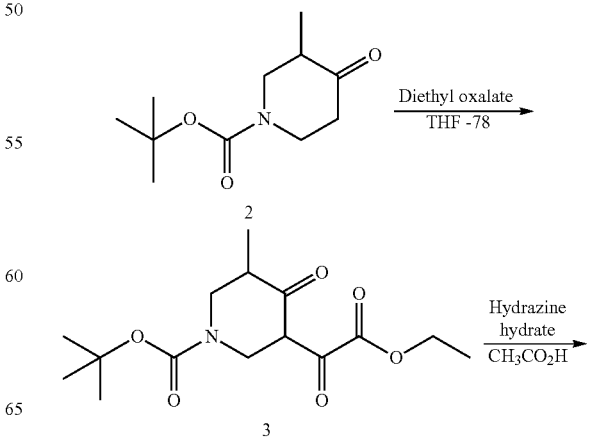

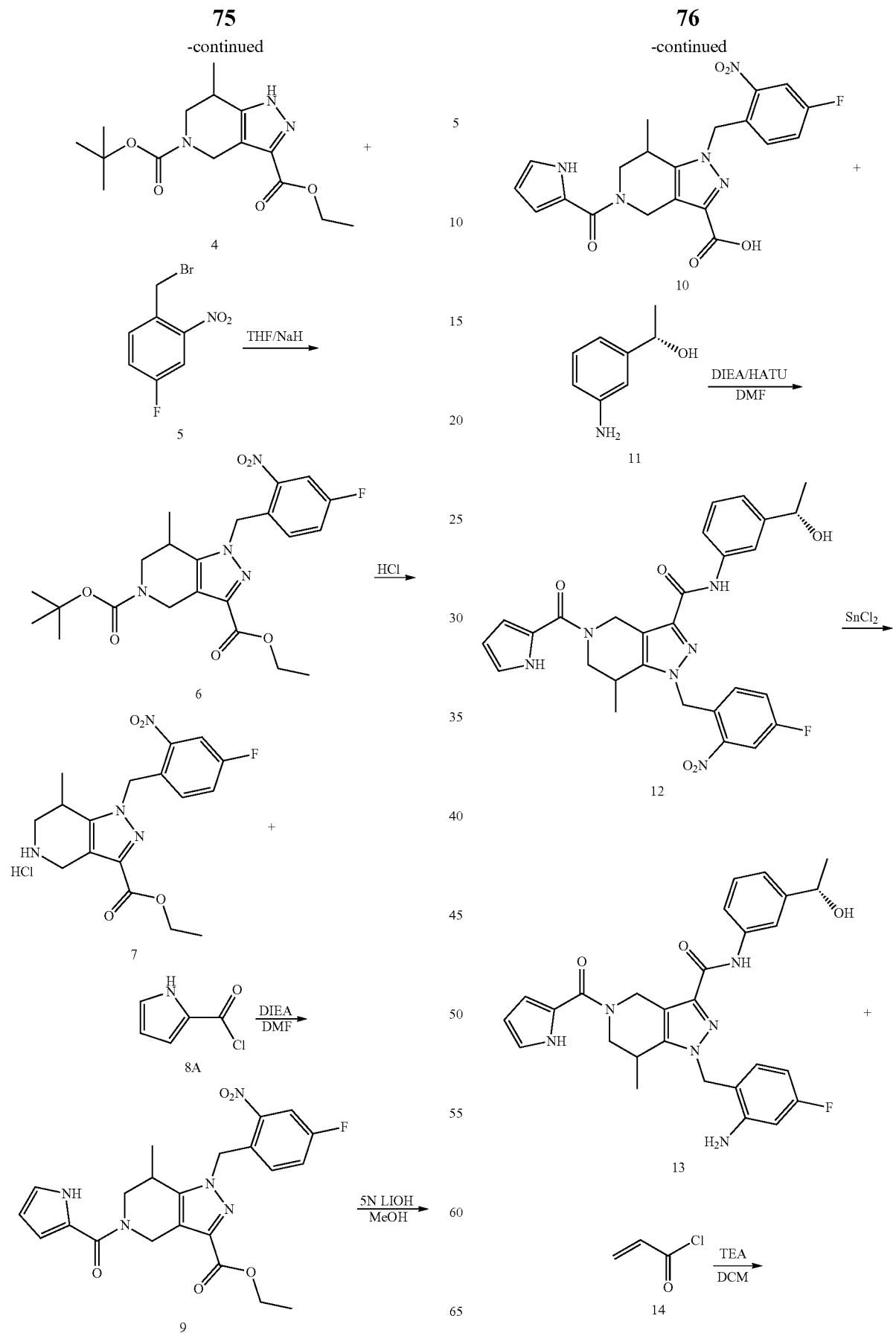

-continued

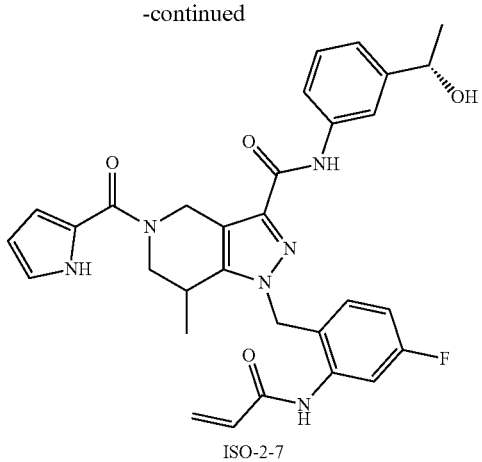

ISO-2-7

5-(tert-butyl) 3-ethyl 1-(4-fluoro-2-nitrobenzyl)-7-methyl-1,4,6,7-tetrahydro-5H-pyrazolo[4,3-c]pyridine-3,5-dicarboxylate (6) To a solution of 5-(tert-butyl) 3-ethyl 7-methyl-1,4,6,7-tetrahydro-5H-pyrazolo[4,3-c]pyridine-3,5-dicarboxylate (4) (1.24 g, 4 mmol) in dry THF (20 mL) was added NaH (60% wt dispersion in mineral oil, 0.2 g, 4.8 mmol) with stirring under nitrogen. After 1 h, 1-(bromomethyl)-4-fluoro-2-nitrobenzene (0.94 g, 4 mmol) was added and the reaction mixture was stirred 4 h under nitrogen. The reaction mixture was quenched with water and pH adjusted to 6 with 1N HCl. The mixture was diluted with brine and extracted with ethyl acetate. The combined extracts were dried over $Na_2SO_4$, filtered and concentrated under reduced pressure. The residue was purified by silica gel chromatography (petroleum ether:ethyl acetate=5:1) to afford 5-(tert-butyl) 3-ethyl 1-(4-fluoro-2-nitrobenzyl)-7-methyl-1,4,6,7-tetrahydro-5H-pyrazolo[4,3-c]pyridine-3,5-dicarboxylate (1 g, 54%) as a light yellow solid. MS m/z 463.17[M+H]$^+$.

Ethyl 1-(4-fluoro-2-nitrobenzyl)-7-methyl-4,5,6,7-tetrahydro-1H-pyrazolo[4,3-c]pyridine-3-carboxylate hydrochloride (7) To a round-bottom flask containing 5-(tert-butyl) 3-ethyl 1-(4-fluoro-3-nitrobenzyl)-7-methyl-1,4,6,7-tetrahydro-5H-pyrazolo[4,3-c]pyridine-3,5-dicarboxylate (6) (1 g) was added HCl (4 N in EA, 10 mL). The resulting clear solution was stirred at room temperature for 3 h. The reaction mixture was concentrated under reduced pressure and the resulting residue was dried to under high vacuum to afford ethyl 1-(4-fluoro-3-nitrobenzyl)-7-methyl-4,5,6,7-tetrahydro-1H-pyrazolo[4,3-c]pyridine-3-carboxylate hydrochloride (0.85 g, 100%) as a yellow solid.

Ethyl 1-(4-fluoro-2-nitrobenzyl)-7-methyl-5-(1H-pyrrole-2-carbonyl)-4,5,6,7-tetrahydro-1H-pyrazolo[4,3-c]pyridine-3-carboxylate (9) To a solution of ethyl 1-(4-fluoro-2-nitrobenzyl)-7-methyl-4,5,6,7-tetrahydro-1H-pyrazolo[4,3-c]pyridine-3-carboxylate hydrochloride (7) (0.85 g, 2.1 mmol) in DCM (10 mL) was added DIEA(0.67 g, 5.2 mmol) and 1H-pyrrole-2-carbonyl chloride (8A) (0.6 g, 2.5 mmol) at 0° C. for 10 min. The reaction mixture was diluted with water and saturated aqueous $NaHCO_3$ and extracted with DCM. The organic layer was washed with brine, dried over $Na_2SO_4$, concentrated under reduced pressure and the residue was purified by silica gel chromatography (petroleum ether:ethyl acetate=3:1) to afford the compound as a yellow solid (0.76 g, 80%). MS m/z 456.37[M+H]$^+$.

1-(4-fluoro-2-nitrobenzyl)-7-methyl-5-(1H-pyrrole-2-carbonyl)-4,5,6,7-tetrahydro-1H-pyrazolo[4,3-c]pyridine-3-carboxylic acid (10) To a solution of ethyl 1-(4-fluoro-2-nitrobenzyl)-7-methyl-5-(1H-pyrrole-2-carbonyl)-4,5,6,7-tetrahydro-1H-pyrazolo[4,3-c]pyridine-3-carboxylate (9) (0.1 g, 0.22 mmol) in MeOH (3 mL) was added 5N LiOH (1 mL). The clear solution was stirred at room temperature for 1 h. The reaction mixture was added water and pH was adjusted to 6 with 1 N HCl. The resulting precipitate was collected by filtration and dried on a lyophilizer overnight to afford 1-(4-fluoro-2-nitrobenzyl)-7-methyl-5-(1H-pyrrole-2-carbonyl)-4,5,6,7-tetrahydro-1H-pyrazolo[4,3-c]pyridine-3-carboxylic acid (70 mg, 74.5%) as a white solid. MS m/z 428.39[M+H]$^+$.

1-(4-fluoro-2-nitrobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (12) To a solution of 1-(4-fluoro-2-nitrobenzyl)-7-methyl-5-(1H-pyrrole-2-carbonyl)-4,5,6,7-tetrahydro-1H-pyrazolo[4,3-c]pyridine-3-carboxylic acid (10) (70 mg, 0.16 mmol) in DMF (2 mL) were added (S)-1-(3-aminophenyl)ethan-1-ol (25 mg, 0.18 mmol), HATU (92 mg, 0.24 mmol) and DIEA (42 mg, 0.32 mmol). The mixture was stirred at room temperature under nitrogen. After 1 h, the reaction mixture was added water and the resulting precipitate was collected by filtration and dried on a lyophilizer overnight to afford compound (12)(74 mg, 85%) as a white solid. MS m/z 547.48[M+H]$^+$.

1-(2-amino-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (13) To a solution of 5-((1H-pyrrol-2-yl)methyl)-1-(4-fluoro-2-nitrobenzyl)-N-(3-((5)-1-hydroxyethyl)phenyl)-7-methyl-4,5,6,7-tetrahydro-1H-pyrazolo[4,3-c]pyridine-3-carboxamide (12) (0.4 g, 0.73 mmol) in ethyl acetate/methanol (4/1)(10 mL) was added stannous chloride (1.11 g, 5.86 mmol). The resulting mixture was heated at 80° C. overnight. The reaction mixture was added DCM and the p H adjusted to ~8 with saturated aqueous $NaHCO_3$ and extracted with DCM. The organic layer was washed with brine, dried over $Na_2SO_4$, concentrated under reduced pressure and the residue was purified by silica gel chromatography (DCM:MeOH=50:1) to afford the compound as a white solid (0.36 g, 95.5%). MS m/z 517.1[M+H]$^+$.

1-(2-acrylamido-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (ISO-2-7) To a solution of 1-(2-amino-4-fluorobenzyl)-N-(3-((5)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (13) (0.36 g, 0.7 mmol) in DCM (5 mL) was added DIEA (0.18 g, 1.4 mmol) and acryloyl chloride (95 mg, 1.05 mmol) at 0° C. for 10 min. The reaction mixture was diluted with water and saturated aqueous $NaHCO_3$ and extracted with DCM. The organic layer was washed with brine, dried over $Na_2SO_4$, concentrated under reduced pressure and the residue was purified by silica gel chromatography (DCM:MeOH=20:1) to afford the compound as a white solid (60 mg, 15%). MS m/z 571.4[M+H]$^+$. $^1$H NMR (400 MHz, DMSO) δ 11.54 (s, 1H), 10.19 (s, 1H), 9.95 (s, 1H), 7.86 (s, 1H), 7.76 (m, 1H), 7.43 (m, 1H), 7.08 (m, 1H), 7.03 (m, 1H), 6.91 (m, 1H), 6.80 (m, 1H), 6.60 (s, 1H), 6.40-6.33 (m, 1H), 6.29 (s, 1H), 6.20 (m, 1H), 5.96 (dd, J=10.4, 1.6 Hz, 1H), 5.85 (m, 1H), 5.80 (m, 1H), 5.41 (q, J=6.6 Hz, 1H), 5.29 (d, J=16.5 Hz, 1H), 4.67 (d, J=14.7 Hz, 1H), 4.32 (d, J=13.1 Hz, 1H), 3.42 (m, 1H), 3.17 (m, 1H), 3.13 (s, 1H), 1.51 (d, J=6.6 Hz, 3H), 1.08 (d, J=6.9 Hz, 3H).

The synthesis of 1-(2-(acrylamidomethyl)-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (ISO-2-8)
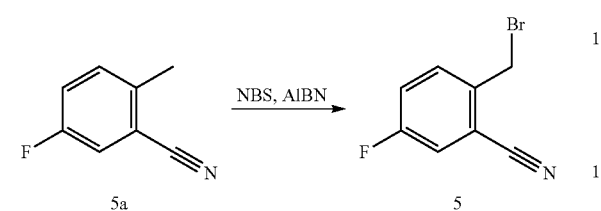
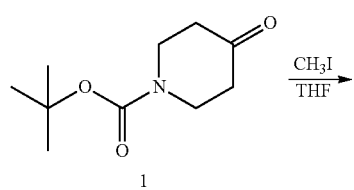
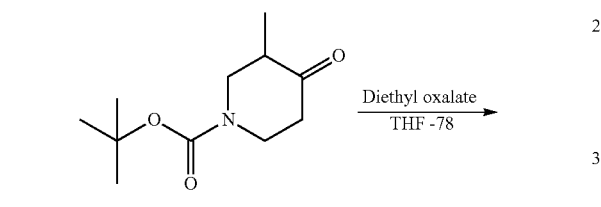
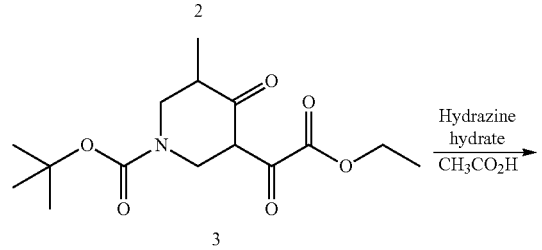
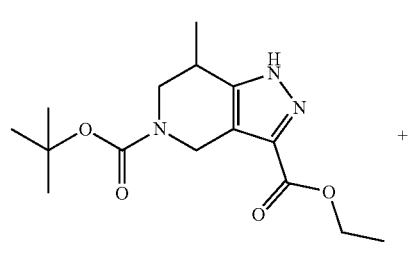
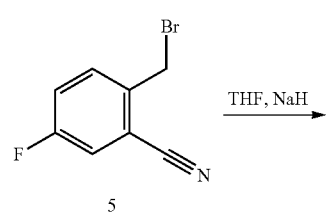
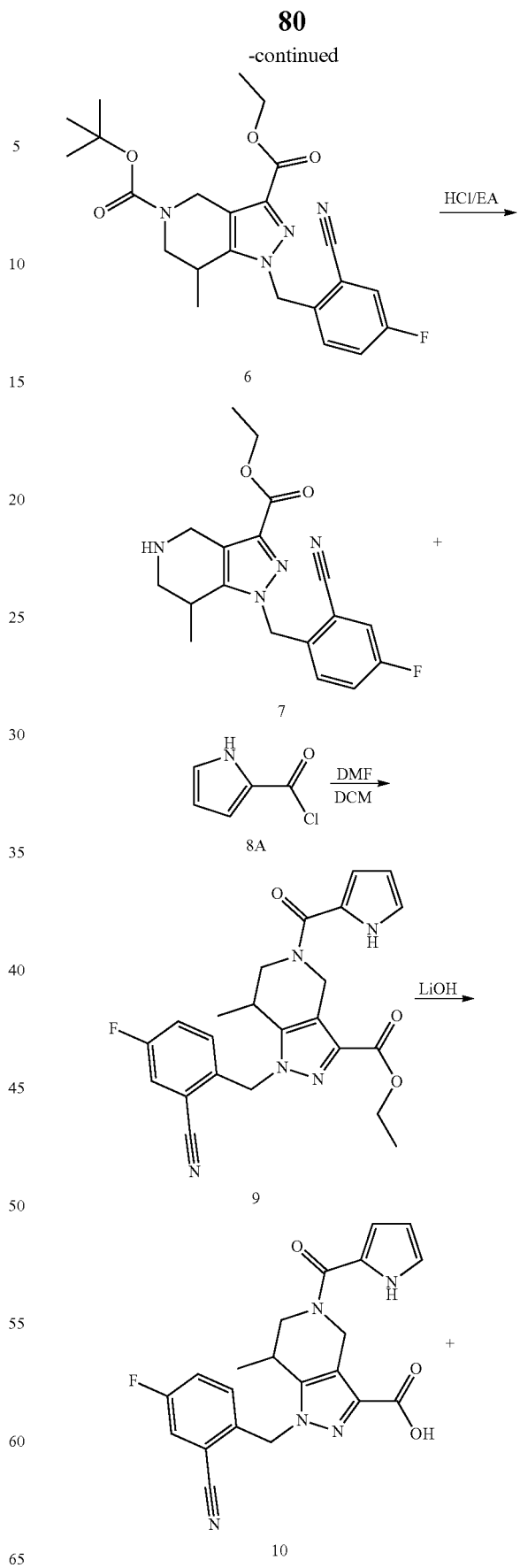

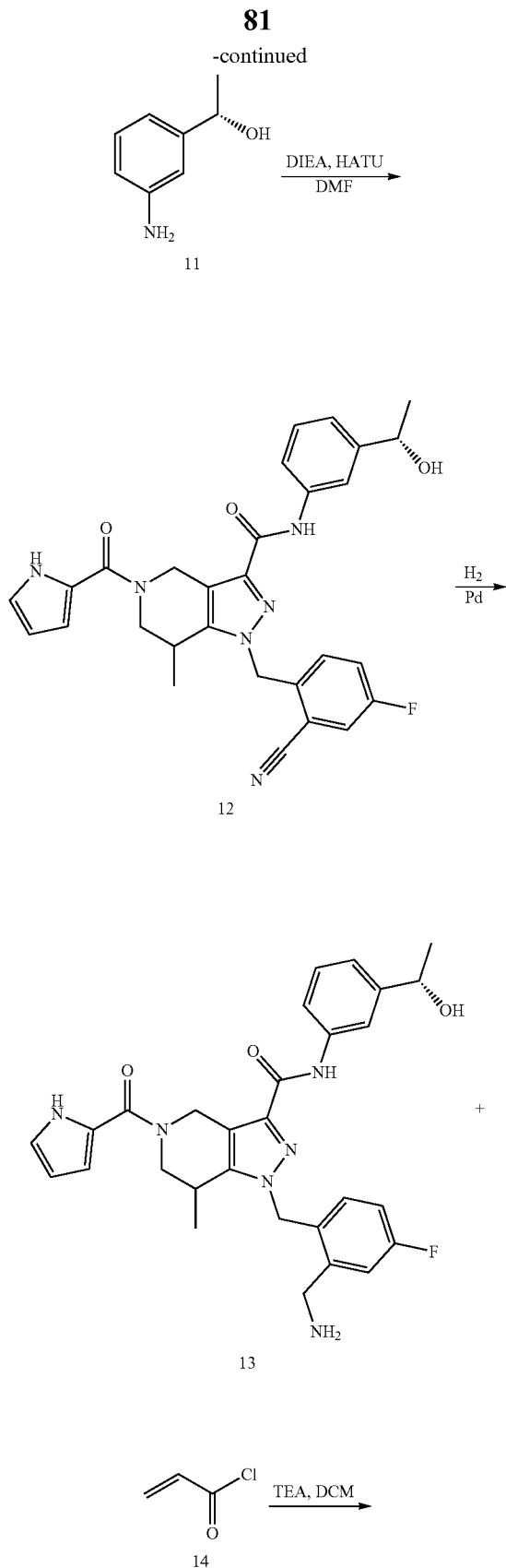

2-(bromomethyl)-5-fluorobenzonitrile (5) To a solution of 5-fluoro-2-methylbenzonitrile (5a)(5 g, 37 mmol) in CCl$_4$ (50 mL) was added NBS (7.3 g, 41 mmol) and AIBN (0.6 g, 3.7 mmol). The resulting mixture was heated at 80° C. overnight. The reaction mixture concentrated under reduced pressure and the residue was purified by silica gel chromatography (petroleum ether/ethylacetate=5:1) to afford the compound as a white solid (2.8 g, 35%). MS m/z 214.96 [M+H]$^+$.

5-(tert-butyl)3-ethyl1-(2-cyano-4-fluorobenzyl)-7-methyl-1,4,6,7-tetrahydro-5H-pyrazolo[4,3-c]pyridine-3,5-dicarboxylate (6) To a solution of 5-(tert-butyl) 3-ethyl 7-methyl-1,4,6,7-tetrahydro-5H-pyrazolo[4,3-c]pyridine-3,5-dicarboxylate (4) (0.8 g, 2.6 mmol) in dry THF (20 mL) was added NaH (60% wt dispersion in mineral oil, 0.2 g, 5 mmol) with stirring under nitrogen. After 1 h, 2-(bromomethyl)-5-fluorobenzonitrile (0.7 g, 3.3 mmol) was added and the reaction mixture was stirred 4 h under nitrogen. The reaction mixture was quenched with water and the pH was adjusted to 6 with 1 N HCl. The mixture was diluted with brine and extracted with ethyl acetate. The combined extracts were dried over Na$_2$SO$_4$, filtered and concentrated under reduced pressure. The residue was purified by silica gel chromatography (petroleum ether:ethyl acetate=5:1) to afford 5-(tert-butyl) 3-ethyl 1-(2-cyano-4-fluorobenzyl)-7-methyl-1,4,6,7-tetrahydro-5H-pyrazolo[4,3-c]pyridine-3,5-dicarboxylate (1.4 g, 95%) as a light yellow solid. MS m/z 443.2[M+H]$^+$.

Ethyl 1-(2-cyano-4-fluorobenzyl)-7-methyl-4,5,6,7-tetrahydro-1H-pyrazolo[4,3-c]pyridine-3-carboxylate (7) To a round-bottom flask containing 5-(tert-butyl) 3-ethyl 1-(2-cyano-4-fluorobenzyl)-7-methyl-1,4,6,7-tetrahydro-5H-pyrazolo[4,3-c]pyridine-3,5-dicarboxylate (6) (1.4 g, 2 mmol) was added HCl (4 N in ethyl acetate, 5 mL). The resulting clear solution was stirred at room temperature for 3 h. The reaction mixture was quenched with water and pH was adjusted to 7 with NaHCO$_3$. The mixture was diluted with brine and extracted with DCM. The combined extracts were dried over Na$_2$SO$_4$, filtered and concentrated under reduced pressure and the resulting residue was dried under high vacuum to afford ethyl 1-(2-cyano-4-fluorobenzyl)-7-methyl-4,5,6,7-tetrahydro-1H-pyrazolo[4,3-c]pyridine-3-carboxylate (0.8 g, 60%) as a yellow solid. MS m/z 343.1 [M+H]$^+$.

Ethyl 1-(2-cyano-4-fluorobenzyl)-7-methyl-5-(1H-pyrrole-2-carbonyl)-4,5,6,7-tetrahydro-1H-pyrazolo[4,3-c]pyridine-3-carboxylate (9) To a solution of ethyl 1-(2-cyano-4-fluorobenzyl)-7-methyl-4,5,6,7-tetrahydro-1H-pyrazolo[4,3-c]pyridine-3-carboxylate (7) (0.8 g, 2.5 mmol) in DCM (10 mL) was added DIEA (0.65 g, 6.25 mmol) and 1H-pyrrole-2-carbonyl chloride (0.31 g, 3 mmol) at 0° C. for 10 min. The reaction mixture was diluted with water and saturated aqueous NaHCO$_3$ and extracted with two portions of DCM. The organic layer was washed with brine, dried over Na$_2$SO$_4$, concentrated under reduced pressure and the residue was purified by silica gel chromatography (petroleum ether:ethyl acetate=2:1) to afford the compound as a yellow solid (0.8 g, 70%). MS m/z 436.1[M+H]$^+$.

1-(2-cyano-4-fluorobenzyl)-7-methyl-5-(1H-pyrrole-2-carbonyl)-4,5,6,7-tetrahydro-1H-pyrazolo[4,3-c]pyridine-3-carboxylic acid (10) To a solution of ethyl 1-(2-cyano-4-fluorobenzyl)-7-methyl-5-(1H-pyrrole-2-carbonyl)-4,5,6,7-tetrahydro-1H-pyrazolo[4,3-c]pyridine-3-carboxylate (9) (0.8 g, 1.84 mmol) in 1,4-dioxane (5 mL) was added 5 N LiOH (5 mL). The clear solution was stirred at room temperature for 1 h. The reaction mixture was added water and pH was adjusted o 6 with 1 N HCl. The resulting precipitate was collected by filtration and dried on a lyophilizer overnight to afford 1-(2-cyano-4-fluorobenzyl)-7-methyl-5-(1H-pyrrole-2-carbonyl)-4,5,6,7-tetrahydro-1H-pyrazolo[4,3-c]pyridine-3-carboxylic acid (0.7 g, 89%) as a white solid. MS m/z 408.1[M+H]$^+$.

1-(2-cyano-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (12) To a solution of 1-(2-cyano-4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.72 g, 1.75 mmol) in DMF (5 mL) were added (S)-1-(3-aminophenyl)ethan-1-ol (0.4 g, 3.5 mmol), HATU (0.8 g, 2.1 mmol) and DIEA (0.4 g, 3 mmol). The mixture was stirred at room temperature under nitrogen. After 1 h, the reaction mixture was added with water and the resulting precipitate was collected by filtration and dried on a lyophilizer overnight to afford compound (12)(0.85 g, 99%) as a white solid. MS m/z 527[M+H]$^+$.

1-(2-(aminomethyl)-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (13) To a solution of 1-(2-cyano-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (12) (0.2 g, 0.4 mmol) in methanol (10 mL) was added hydrochloric acid (2 mL) and Pd/C (0.2 g). The resulting mixture was stirred at room temperature overnight under H2. The organic layer was concentrated under reduced pressure and the residue was purified by silica gel chromatography (DCM:MeOH=50:1) to afford the compound as a white solid (0.06 g, 23%). MS m/z 531[M+H]$^+$.

1-(2-(acrylamidomethyl)-4-fluorobenzyl)-N-(3-((S)1-hydroxyethyl)phenyl)-7-methyl-5-(1H-pyrrole-2-carbonyl)-4,5,6,7-tetrahydro-1H-pyrazolo[4,3-c]pyridine-3-carboxamide (ISO-2-8) To a solution of 1-(2-(aminomethyl)-4-fluorobenzyl)-N-(3-((S)-1-hydroxyethyl)phenyl)-7-methyl-5-(1H-pyrrole-2-carbonyl)-4,5,6,7-tetrahydro-1H-pyrazolo[4,3-c]pyridine-3-carboxamide (13) (0.06 g, 0.13 mmol) in DCM (10 mL) was added TEA (0.05 g, 0.4 mmol) and acryloyl chloride (0.015 g, 0.15 mmol) at 0° C. for 10 min. The reaction mixture was diluted with water and saturated aqueous NaHCO$_3$ and extracted with two portions of DCM. The organic layer was washed with brine, dried over Na$_2$SO$_4$, concentrated under reduced pressure and the residue was purified by silica gel chromatography (DCM:MeOH=20:1) to afford the compound as a white solid (31 mg, 46%). MS m/z 585.25[M+H]$^+$. $^1$H NMR (400 MHz, DMSO) 611.54 (s, 1H), 9.87 (s, 1H), 8.82 (s, 1H), 7.82 (s, 1H), 7.63 (m, 1H), 7.25 (m, 1H), 7.11 (m, 1H), 7.03 (m, 2H), 6.92 (m, 1H), 6.70 (m, 1H), 6.59 (m, 1H), 6.37 (m, 1H), 6.23-6.12 (m, 2H), 5.67 (dd, J=10.2, 2.1 Hz, 1H), 5.56 (q, J=16.4 Hz, 2H), 5.34 (d, J=16.6 Hz, 1H), 5.14 (s, 1H), 4.75-4.45 (m, 4H), 4.37 (d, J=11.8 Hz, 1H), 3.39 (m, 1H), 3.19 (m, 1H), 1.31 (d, J=6.4 Hz, 3H), 1.06 (dd, J=14.1, 6.9 Hz, 3H).

Synthesis of N-(1-acryloylpyrrolidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-9)

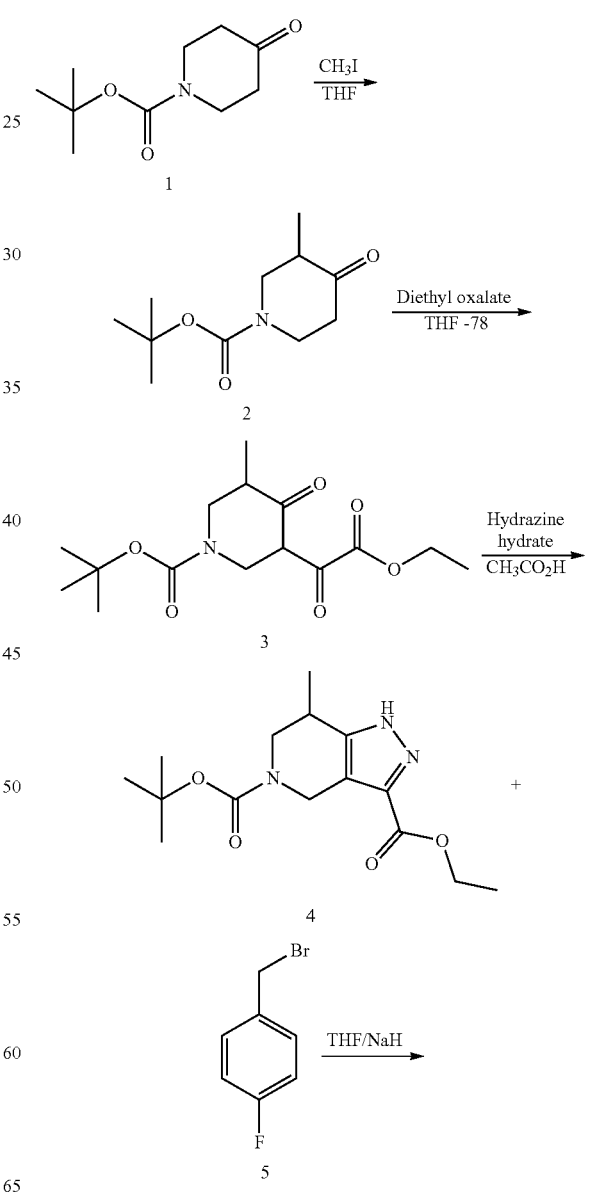

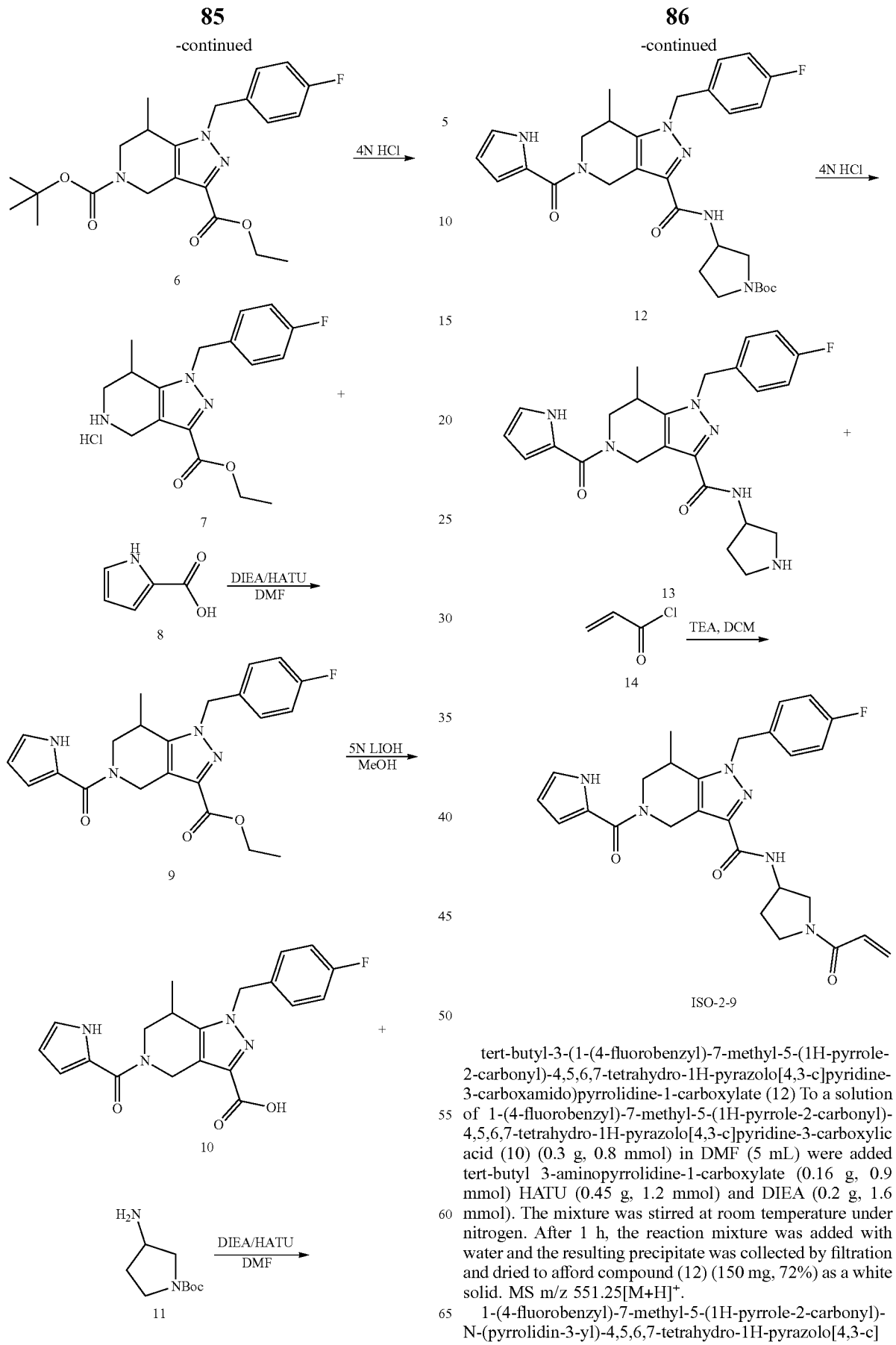

tert-butyl-3-(1-(4-fluorobenzyl)-7-methyl-5-(1H-pyrrole-2-carbonyl)-4,5,6,7-tetrahydro-1H-pyrazolo[4,3-c]pyridine-3-carboxamido)pyrrolidine-1-carboxylate (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.3 g, 0.8 mmol) in DMF (5 mL) were added tert-butyl 3-aminopyrrolidine-1-carboxylate (0.16 g, 0.9 mmol) HATU (0.45 g, 1.2 mmol) and DIEA (0.2 g, 1.6 mmol). The mixture was stirred at room temperature under nitrogen. After 1 h, the reaction mixture was added with water and the resulting precipitate was collected by filtration and dried to afford compound (12) (150 mg, 72%) as a white solid. MS m/z 551.25[M+H]$^+$.

1-(4-fluorobenzyl)-7-methyl-5-(1H-pyrrole-2-carbonyl)-N-(pyrrolidin-3-yl)-4,5,6,7-tetrahydro-1H-pyrazolo[4,3-c]pyridine-3-carboxamide (13) To a round-bottom flask containing tert-butyl-3-(1-(4-fluorobenzyl)-7-methyl-5-(1H-pyrrole-2-carbonyl)-4,5,6,7-tetrahydro-1H-pyrazolo[4,3-c]pyridine-3-carboxamido)pyrrolidine-1-carboxylate (12) (0.15 g, 0.27 mmol) was added HCl (4 N in ethyl acetate, 5 mL). The resulting clear solution was stirred at room temperature. The reaction mixture was concentrated under reduced pressure and the resulting residue was dried to afford the product 13 (130 mg, 100%) as a yellow solid.

N-(1-acryloylpyrrolidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-9) To a solution of 1-(4-fluorobenzyl)-7-methyl-5-(1H-pyrrole-2-carbonyl)-N-(pyrrolidin-3-yl)-4,5,6,7-tetrahydro-1H-pyrazolo[4,3-c]pyridine-3-carboxamide (13) (130 mg, 0.28 mmol) in DCM (5 mL) was added TEA (90 mg, 0.54 mmol) and acryloyl chloride (30 mg, 0.36 mmol) at 0° C. The reaction mixture was diluted with water and saturated aqueous NaHCO₃ and extracted with DCM. The organic layer was washed with brine, dried over Na₂SO₄, concentrated under reduced pressure and the residue was purified by silica gel chromatography to afford the compound as a white solid (50 mg, 36%). MS m/z 505 [M+H]⁺. 1H NMR (400 MHz, DMSO) δ 11.53 (s, 1H), 8.35 (m, 1H), 7.18 (d, J=7.4 Hz, 4H), 6.91 (s, 1H), 6.62 (m, 2H), 6.22 (m, 1H), 6.08 (m, 1H), 5.65 (m, 1H), 5.38 (q, J=16.2 Hz, 2H), 5.24 (d, J=16.4 Hz, 1H), 4.60 (m, 1H), 4.47-4.40 (m, 1H), 4.32 (d, J=12.7 Hz, 1H), 3.88-3.46 (m, 3H), 3.39 (m, 2H), 3.12 (m, 1H), 2.22-1.90 (m, 2H), 1.05 (d, J=6.8 Hz, 3H).

The synthesis of N-(1-acryloylazetidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-10)

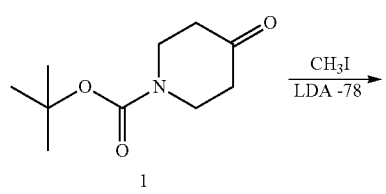

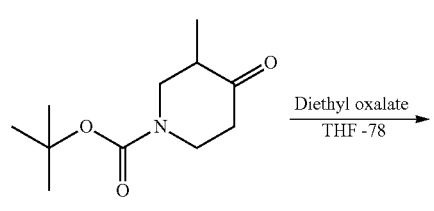

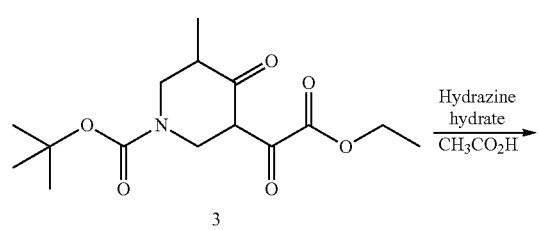

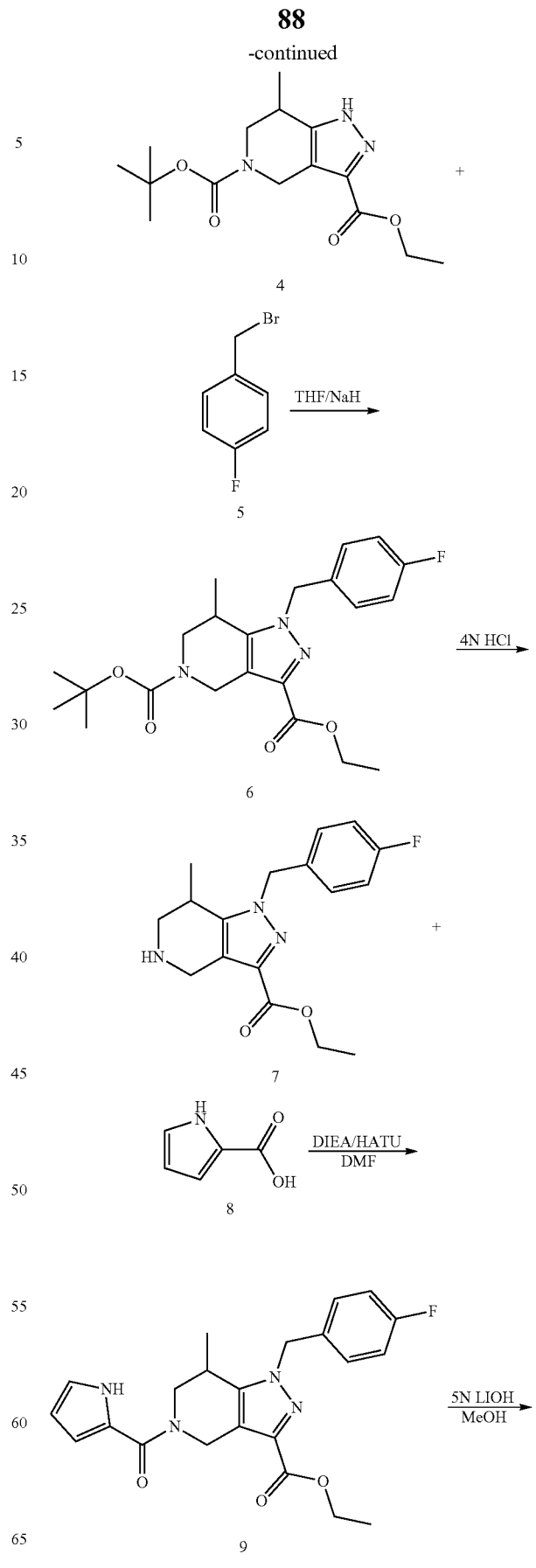

-continued

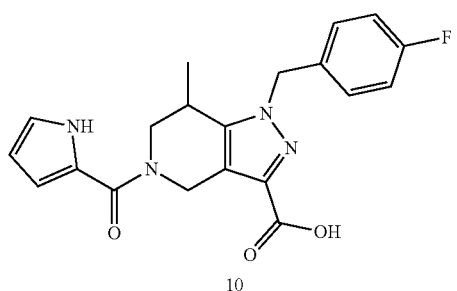

10

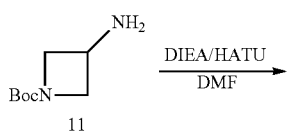

11

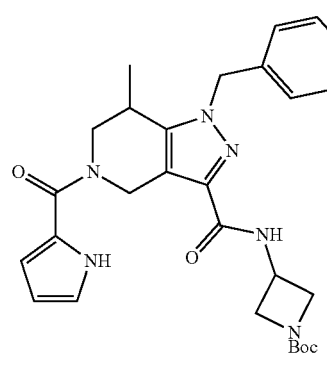

12

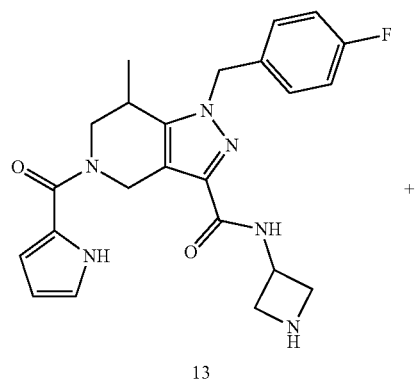

13

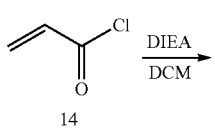

14

-continued

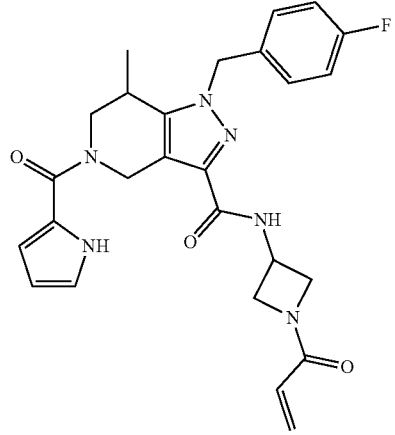

ISO-2-10

3-(1-(4-fluorobenzyl)-7-methyl-5-(1H-pyrrole-2-carbonyl)-4,5,6,7-tetrahydro-1H-pyrazolo[4,3-c]pyridine-3-carboxamido)azetidine-1-carboxylate (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.1 g, 0.26 mmol) in DMF (5 mL) were added tert-butyl 3-aminoazetidine-1-carboxylate (38 mg, 0.28 mmol), HATU (0.15 g, 0.39 mmol) and DIEA (67.2 g, 0.52 mmol). The mixture was stirred at room temperature under nitrogen. After 1 h, the reaction mixture was added with water and the resulting precipitate was collected by filtration and dried to afford compound (12)(95 mg, 72%) as a white solid. MS m/z 537[M+H]$^+$.

N-(azetidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) To a round-bottom flask containing tert-butyl-3-(1-(4-fluorobenzyl)-7-methyl-5-(1H-pyrrole-2-carbonyl)-4,5,6,7-tetrahydro-1H-pyrazolo[4,3-c]pyridine-3-carboxamido)azetidine-1-carboxylate (12) (0.95 g, 0.18 mmol) was added with HCl (4 N in ethyl acetate, 5 mL). The resulting clear solution was stirred at room temperature and then the reaction mixture was concentrated under reduced pressure and the resulting residue was dried under high vacuum to afford the product 13 (90 mg, 100%) as a yellow solid.

N-(1-acryloylazetidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-10) To a solution of N-(azetidin-3-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) (90 mg, 0.106 mmol) in DCM (5 mL) was added TEA (22 mg, 0.212 mmol) and 2-chloroacetyl chloride (30 mg, 0.212 mmol) at 0° C. The reaction mixture was diluted with water and saturated aqueous NaHCO$_3$ and extracted with DCM. The organic layer was washed with brine, dried over Na$_2$SO$_4$, concentrated under reduced pressure and the residue was purified by silica gel chromatography to afford the compound as a white solid (42 mg, 46%). MS m/z 491[M+H]$^+$. $^1$H NMR (400 MHz, DMSO) δ 11.52 (s, 1H), 8.85 (d, J=7.4 Hz, 1H), 7.20 (m, 4H), 6.90 (s, 1H), 6.57 (s, 1H), 6.30 (m, 1H), 6.16 (m, 1H), 6.09 (dd, J=17.0, 2.3 Hz, 1H), 5.66 (dd, J=10.3, 2.2 Hz, 1H), 5.38 (q, J=16.2 Hz, 2H), 5.23 (d, J=16.5 Hz, 1H), 4.76-4.64 (m, 1H), 4.58 (m, 1H), 4.46 (m, 1H), 4.32 (d, J=12.5 Hz, 1H), 4.21 (m, 1H), 4.14 (t, J=9.1 Hz, 1H), 4.04-3.93 (m, 1H), 3.35 (br, 1H), 3.15 (m, 1H), 1.06 (d, J=6.7 Hz, 3H).

The synthesis of N-(5-acrylamidothiophen-2-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-19)
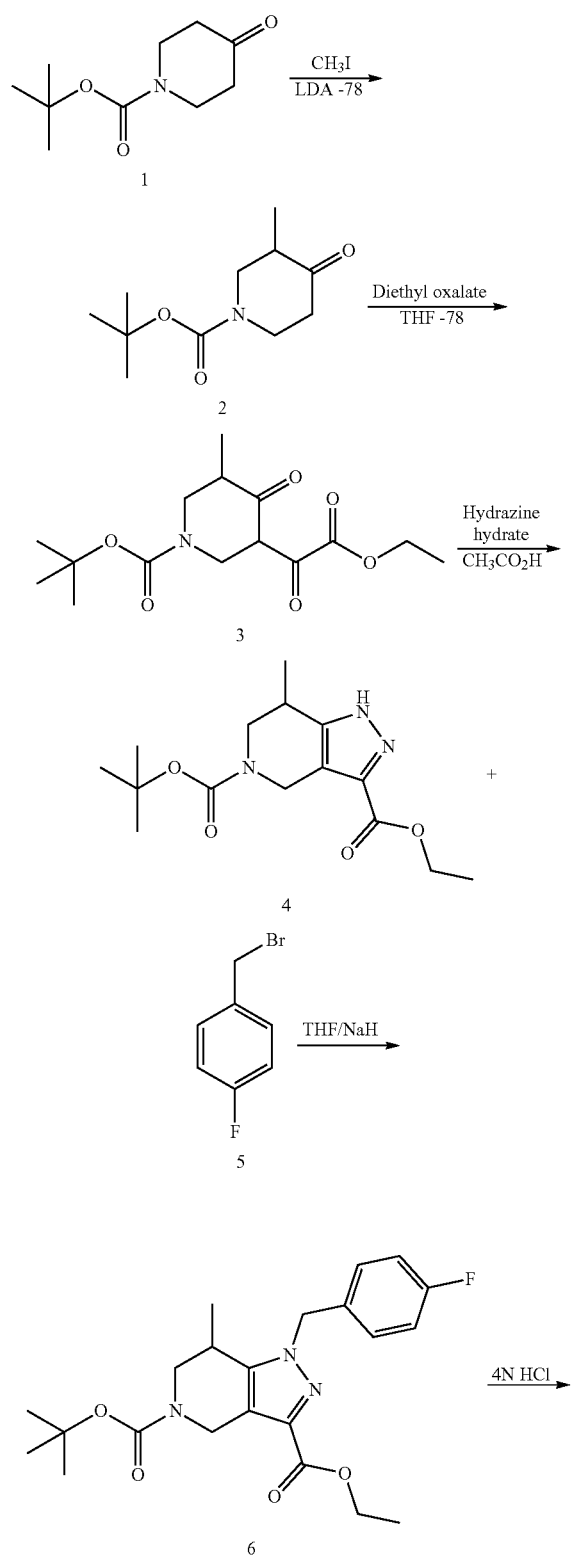
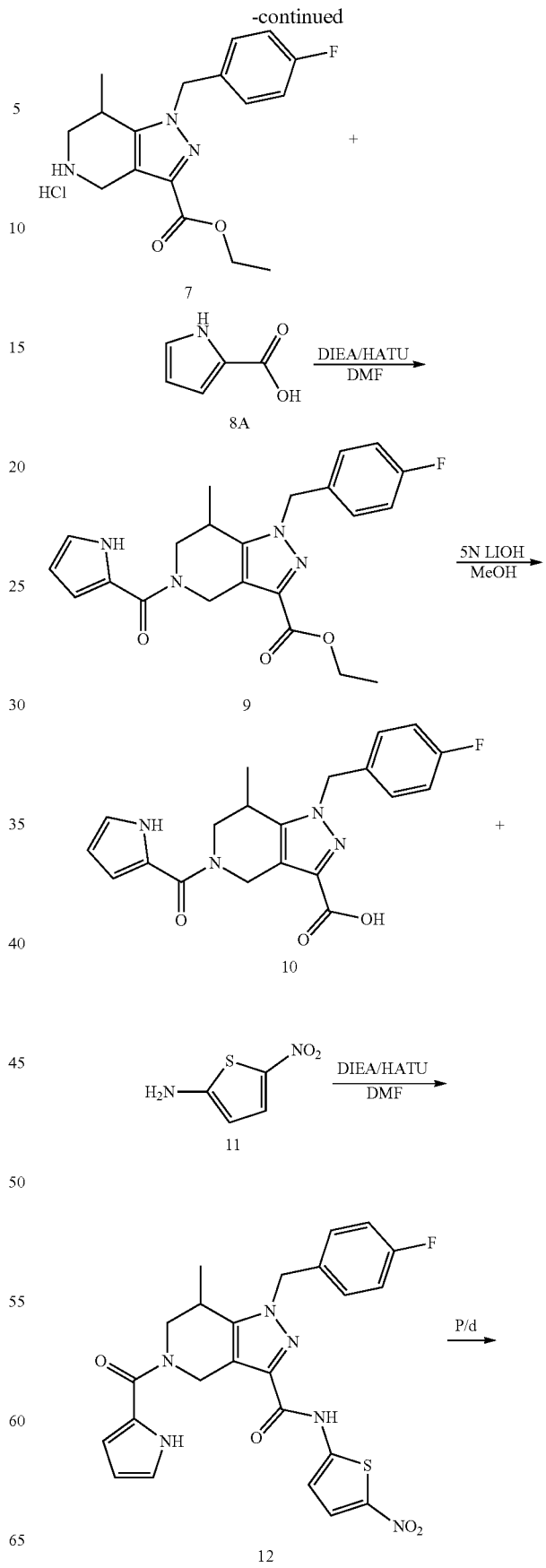

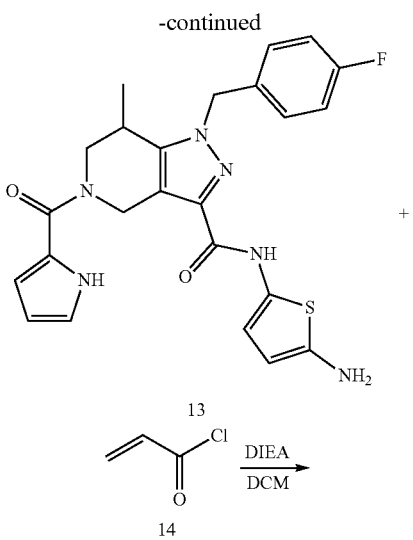

13

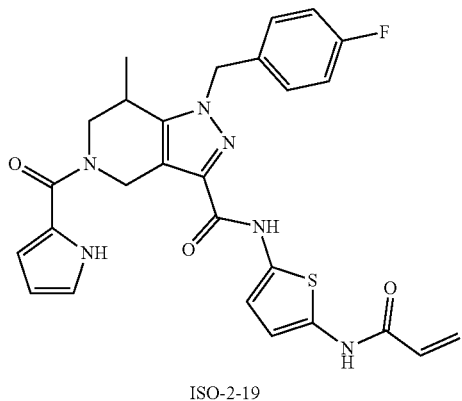

ISO-2-19

1-(4-fluorobenzyl)-7-methyl-N-(5-nitrothiophen-2-yl)-5-(1H-pyrrole-2-carbonyl)-4,5,6,7-tetrahydro-1H-pyrazolo[4,3-c]pyridine-3-carboxamide (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.1 g, 0.26 mmol) in DMF (5 mL) were added 5-nitrothiophen-2-amine (48 mg, 0.28 mmol), HATU (0.15 g, 0.39 mmol) and DIEA (0.067 g, 0.52 mmol). The mixture was stirred at room temperature under nitrogen. After 1 h, the reaction mixture was added with water and the resulting precipitate was collected by filtration and dried to afford compound (12) (120 mg, 82%) as a white solid. MS m/z 509.13[M+H]$^+$.

N-(5-aminothiophen-2-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) To a solution of 1-(4-fluorobenzyl)-7-methyl-N-(5-nitrothiophen-2-yl)-5-(1H-pyrrole-2-carbonyl)-4,5,6,7-tetrahydro-1H-pyrazolo[4,3-c]pyridine-3-carboxamide (12) (0.12 g, 0.25 mmol) in methanol (10 mL) was added hydrochloric acid (2 mL) and Pd/C (0.2 g). The resulting mixture was stirred at room temperature under H2. The organic layer was concentrated under reduced pressure and the residue was purified by silica gel chromatography to afford the compound as a white solid (0.11 g, 88%). MS m/z 479[M+H]$^+$.

N-(5-acrylamidothiophen-2-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-19) To a solution of N-(5-aminothiophen-2-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) (110 mg, 0.206 mmol) in DCM (5 mL) was added TEA (44 mg, 0.42 mmol) and 2-chloroacetyl chloride (48 mg, 0.4 mmol) at 0° C. The reaction mixture was diluted with water and saturated aqueous NaHCO$_3$ and extracted with DCM. The organic layer was washed with brine, dried over Na$_2$SO$_4$, concentrated under reduced pressure and the residue was purified by silica gel chromatography to afford the compound as a white solid (50 mg, 45%). MS m/z 533.17[M+H]$^+$. 1H NMR (400 MHz, DMSO) δ 11.54 (s, 1H), 11.24 (s, 1H), 11.12 (s, 1H), 7.30 (m, 4H), 6.92 (s, 1H), 6.77 (d, J=4.4 Hz, 1H), 6.63 (s, 1H), 6.49 (d, J=4.1 Hz, 1H), 6.39 (m, 1H), 6.28 (m, 2H), 5.76 (d, J=10.1 Hz, 1H), 5.45 (q, J=16.4 Hz, 2H), 5.33 (d, J=16.5 Hz, 1H), 4.69 (d, J=13.4 Hz, 1H), 4.35 (d, J=11.7 Hz, 1H), 3.42 (br, 1H), 3.18 (m, 1H), 1.08 (d, J=6.8 Hz, 3H)

The synthesis of N-(3-acrylamidocyclobutyl)-1-(4-fluorobenzyl)-7-methyl-5-(1H-pyrrole-2 carbonyl)-4,5,6,7-tetrahydro-1H-pyrazolo[4,3-c]pyridine-3-carboxamide (ISO-2-20)

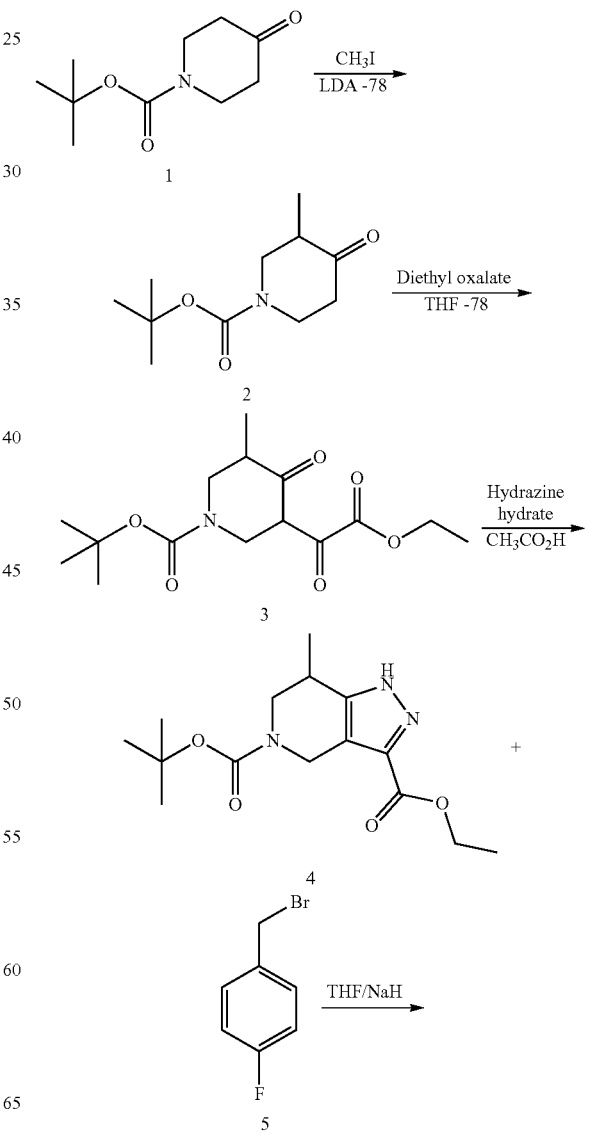

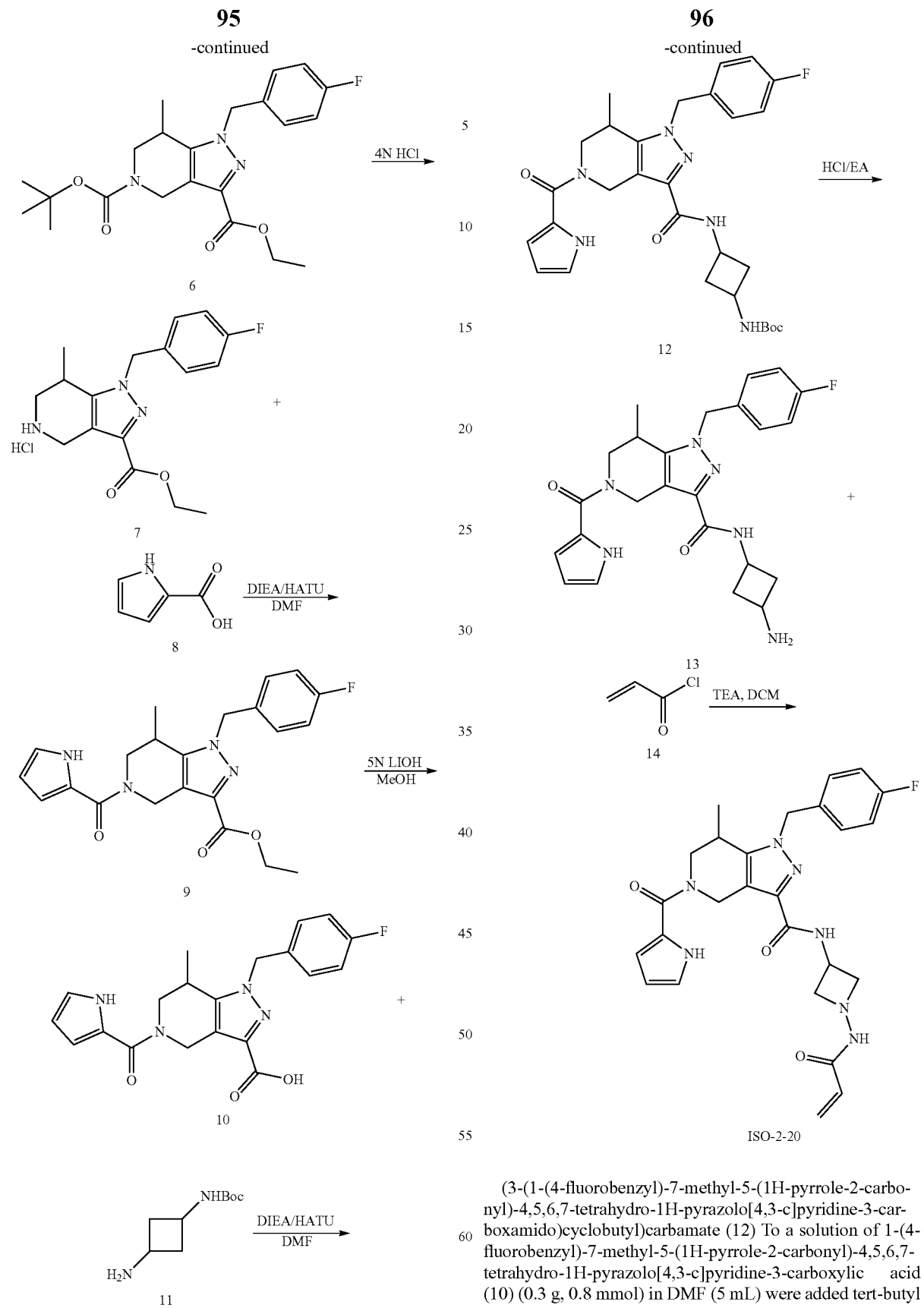

(3-(1-(4-fluorobenzyl)-7-methyl-5-(1H-pyrrole-2-carbonyl)-4,5,6,7-tetrahydro-1H-pyrazolo[4,3-c]pyridine-3-carboxamido)cyclobutyl)carbamate (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.3 g, 0.8 mmol) in DMF (5 mL) were added tert-butyl (3-aminocyclobutyl)carbamate (0.16 g, 0.9 mmol), HATU (0.45 g, 1.2 mmol) and DIEA (0.2 g, 1.6 mmol). The mixture was stirred at room temperature under nitrogen. After 1 h, the reaction mixture was added water and the resulting precipitate was collected by filtration and dried by lyophilizer overnight to provide compound (12) (150 mg, 72%) as a white solid. MS m/z 551.25[M+H]⁺.

N-(3-aminocyclobutyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) To a round-bottom flask containing tert-butyl-3-(1-(4-fluorobenzyl)-7-methyl-5-(1H-pyrrole-2-carbonyl)-4,5,6,7-tetrahydro-1H-pyrazolo[4,3-c]pyridine-3-carboxamido)cyclobutyl)carbamate (12) (0.15 g, 0.27 mmol) was added HCl (4 N in ethyl acetate, 5 mL). The resulting clear solution was stirred at room temperature. The reaction mixture was concentrated under reduced pressure and the resulting residue was dried to constant weight under high vacuum to afford the product (130 mg, 100%) as a yellow solid.

N-(3-acrylamidocyclobutyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-20) To a solution of N-(3-aminocyclobutyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) (130 mg, 0.28 mmol) in DCM (5 mL) was added TEA (90 mg, 0.54 mmol) and acryloyl chloride (30 mg, 0.36 mmol) at 0° C. The reaction mixture was diluted with water and saturated aqueous $NaHCO_3$ and extracted with DCM. The organic layer was washed with brine, dried over $Na_2SO_4$, concentrated under reduced pressure and the residue was purified by silica gel chromatography to afford the compound as a white solid (50 mg, 36%). MS m/z 505 [M+H]⁺. ¹H NMR (400 MHz, DMSO) δ 11.51 (s, 1H), 8.51 (d, J=10.0 Hz, 1H), 8.35 (d, J=10.0 Hz, 1H), 7.28 (m, 4H), 6.90 (s, 1H), 6.53 (s, 1H), 6.28 (m, 2H), 6.07 (m, 1H), 5.57 (d, J=10.0 Hz, 1H), 5.38 (m, 2H), 5.23 (d, J=16.5 Hz, 1H), 4.73-3.85 (m, 4H), 3.36 (m, 1H), 3.15-3.05 (m, 1H), 2.48-2.35 (m, 2H), 2.27-2.01 (m, 2H), 1.06 (d, J=6.8 Hz, 3H)

The synthesis of N-(4-acrylamidophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-25)

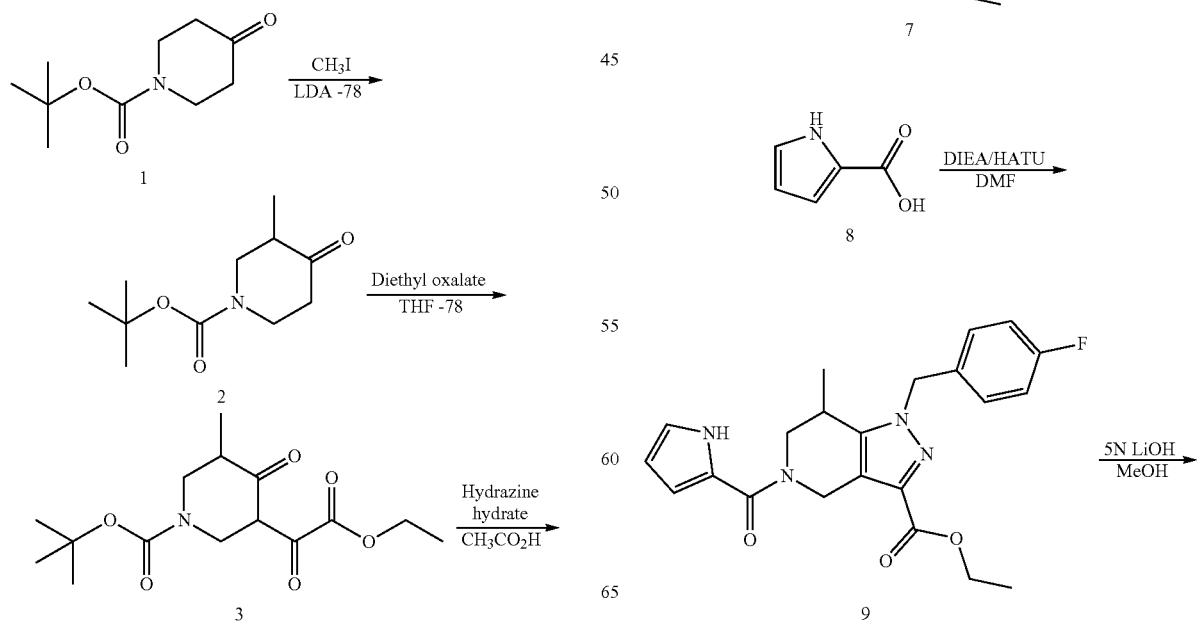

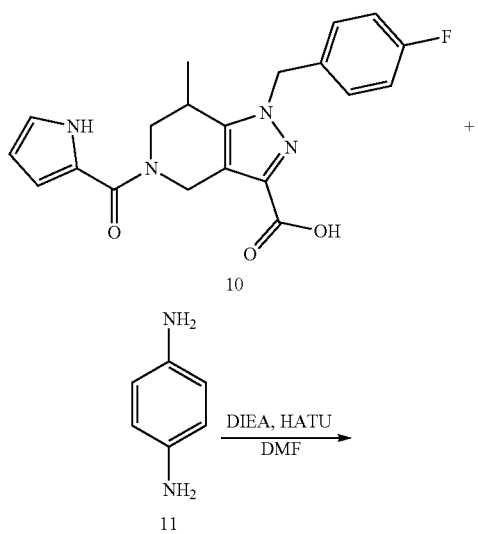

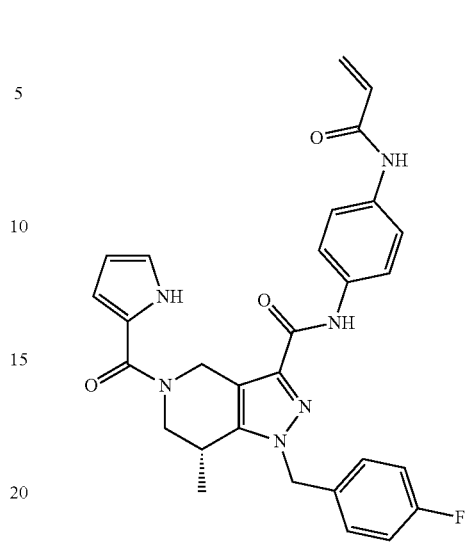

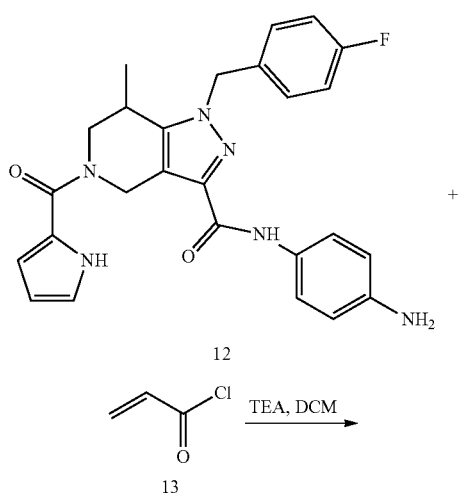

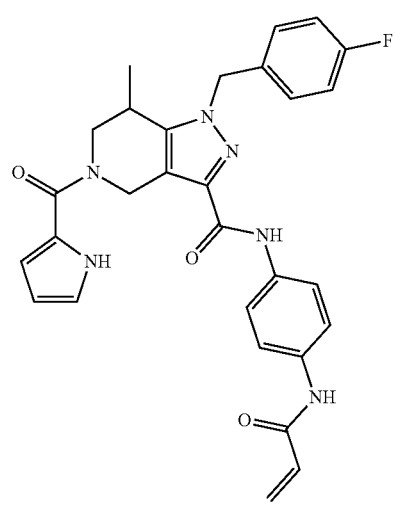

N-(3-aminophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.1 g, 0.26 mmol) in DMF (5 mL) were added benzene-1,4-diamine (28 mg, 0.28 mmol), HATU (0.15 g, 0.39 mmol) and DIEA (67.2 g, 0.52 mmol). The mixture was stirred at room temperature under nitrogen. After 1 h, the reaction mixture was added with water and the resulting precipitate was collected by filtration and dried to provide compound (12) (105 mg, 78%) as a white solid. MS m/z 473.20 [M+H]+.

N-(4-acrylamidophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-25) To a solution of N-(3-aminophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) (90 mg, 0.18 mmol) in DCM (5 mL) was added TEA (44 mg, 0.4 mmol) and acryloyl chloride (30 mg, 0.3 mmol) at 0° C. The reaction mixture was diluted with water and saturated aqueous NaHCO3 and extracted with DCM. The organic layer was washed with brine, dried over Na₂SO₄, concentrated under reduced pressure and the residue was purified by silica gel chromatography to afford the compound as a white solid (36 mg, 25%). MS m/z 527[M+H]⁺. 1H NMR (400 MHz, DMSO) δ 11.54 (s, 1H), 10.37 (s, 1H), 9.98 (s, 1H), 7.80 (d, J=9.0 Hz, 2H), 7.65 (d, J=9.0 Hz, 2H), 7.30 (m, 4H), 6.90 (s, 1H), 6.63 (s, 1H), 6.48 (m, 1H), 6.20 (m, 2H), 5.72 (d, J=10.0 Hz, 1H), 5.44 (q, J=16.0 Hz, 2H), 5.30 (d, J=16.5 Hz, 1H), 4.68 (br, 1H), 4.35 (d, J=13.1 Hz, 1H), 3.37 (m, 1H), 3.10 (m, 1H), 1.06 (d, J=6.9 Hz, 3H).

ISO-2-25-R and ISO-2-25-S were obtained by HPLC separation with a chiral column.

The synthesis of N-(1-acryloylpiperidin-4-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-26)

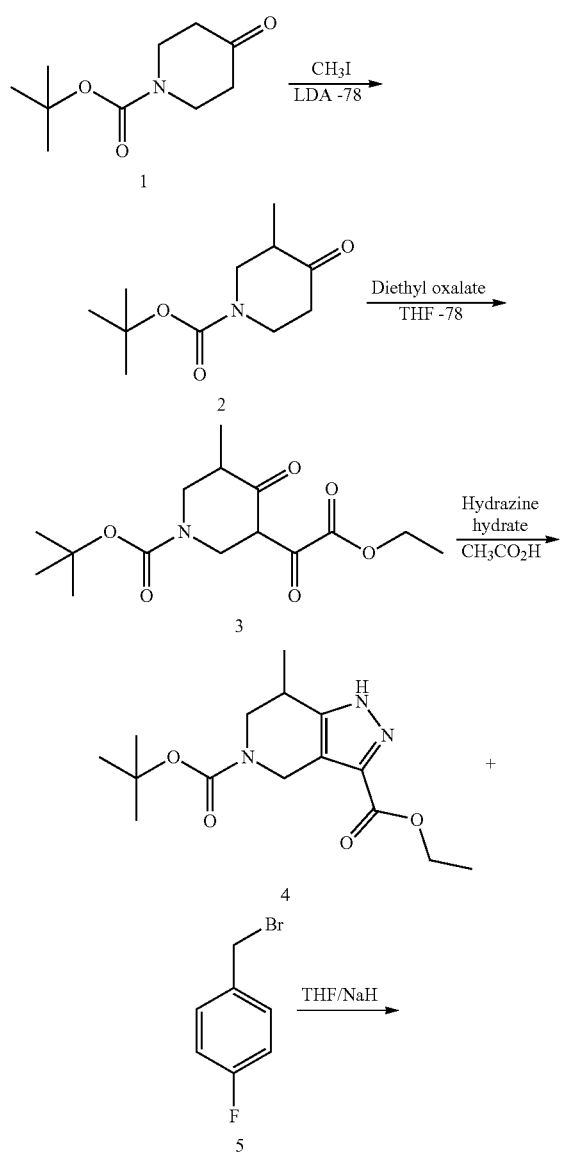

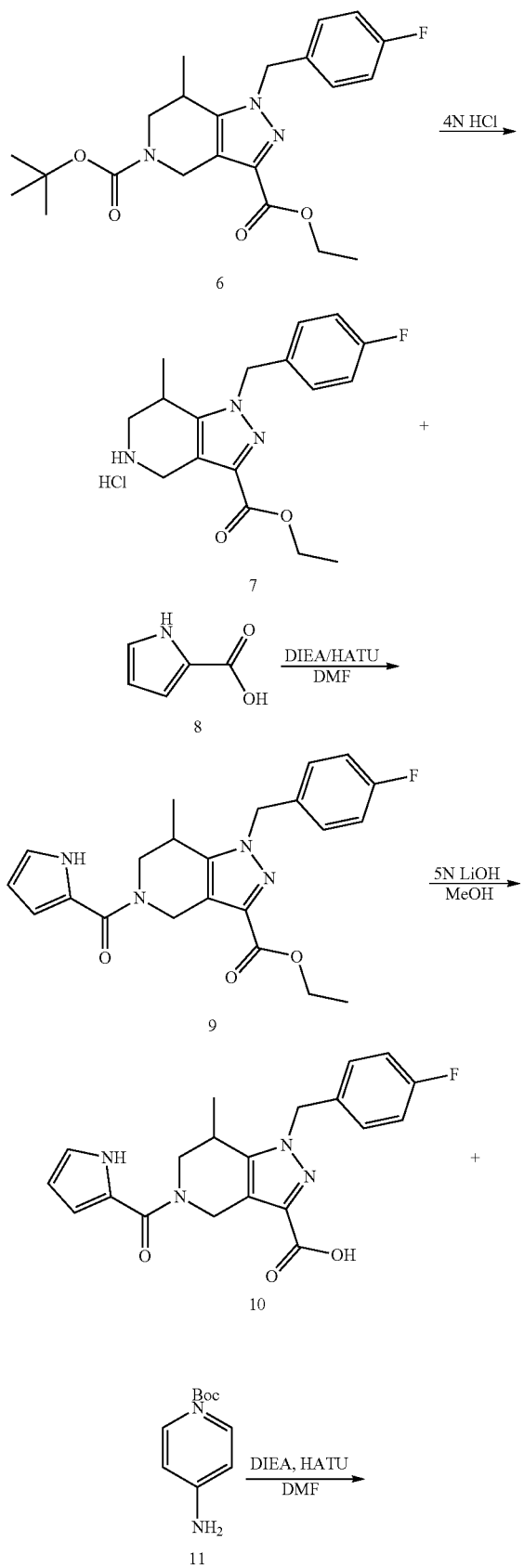

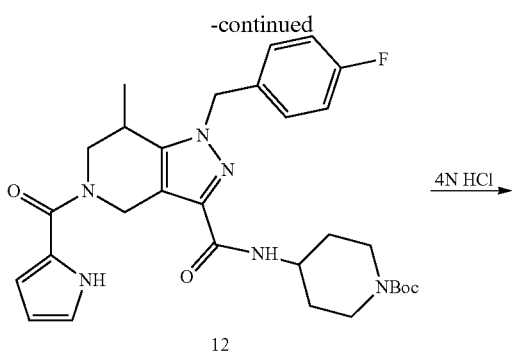

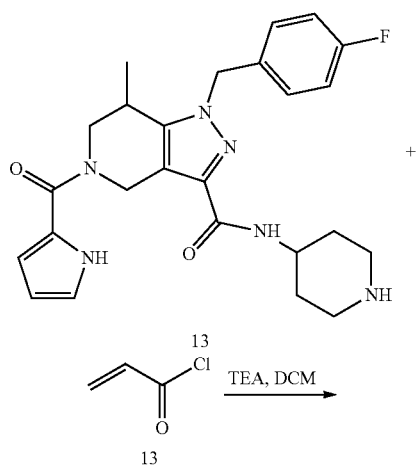

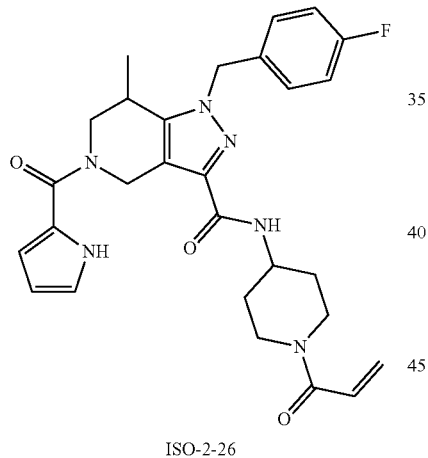

ISO-2-26 tert-butyl-4-(1-(4-fluorobenzyl)-7-methyl-5-(1H-pyrrole-2-carbonyl)-4,5,6,7-tetrahydro-1H-pyrazolo[4,3-c]pyridine-3-carboxamido)piperidine-1-carboxylate (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.1 g, 0.26 mmol) in DMF (5 mL) were added tert-butyl 4-aminopiperidine-1-carboxylate (32.6 mg, 0.28 mmol), HATU (0.15 g, 0.39 mmol) and DIEA (0.067 g, 0.52 mmol). The mixture was stirred at room temperature under nitrogen. After 1 h, the reaction mixture was added water and the resulting precipitate was collected by filtration and dried to afford compound (12) (107 mg, 82%) as a white solid. MS m/z 565[M+H]⁺.

1-(4-fluorobenzyl)-7-methyl-N-(piperidin-4-yl)-5-(1H-pyrrole-2-carbonyl)-4,5,6,7-tetrahydro-1H-pyrazolo[4,3-c]pyridine-3-carboxamide (13) To a round-bottom flask containing tert-butyl-4-(1-(4-fluorobenzyl)-7-methyl-5-(1H-pyrrole-2-carbonyl)-4,5,6,7-tetrahydro-1H-pyrazolo[4,3-c]pyridine-3-carboxamido)piperidine-1-carboxylate (12) (0.1 g, 0.18 mmol) was added with HCl (4 N in ethyl acetate, 5 mL). The resulting clear solution was stirred at room temperature. The reaction mixture was concentrated under reduced pressure and the resulting residue was dried to afford the product (90 mg, 100%) as a yellow solid.

N-(1-acryloylpiperidin-4-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-26) To a solution of 1-(4-fluorobenzyl)-7-methyl-N-(piperidin-4-yl)-5-(1H-pyrrole-2-carbonyl)-4,5,6,7-tetrahydro-1H-pyrazolo[4,3-c]pyridine-3-carboxamide (13) (90 mg, 0.18 mmol) in DCM (5 mL) was added with TEA (44 mg, 0.4 mmol) and acryloyl chloride (30 mg, 0.3 mmol) at 0° C. The reaction mixture was diluted with water and saturated aqueous NaHCO₃ and extracted with DCM. The organic layer was washed with brine and dried. Then the mixture was then concentrated under reduced pressure and the residue was purified by silica gel chromatography to afford the compound as a white solid (35 mg, 37%). MS m/z 519[M+H]⁺. 1H NMR (400 MHz, DMSO) δ 11.52 (s, 1H), 8.01 (d, J=8.3 Hz, 1H), 7.20 (m, 4H), 6.90 (s, 1H), 6.81 (m, 1H), 6.55 (m, 1H), 6.16 (m, 1H), 6.08 (d, J=16.7 Hz, 1H), 5.66 (dd, J=10.5, 2.5 Hz, 1H), 5.40 (q, J=16.2 Hz, 2H), 5.24 (d, J=16.5 Hz, 1H), 4.59 (br, 1H), 4.41 (m, 1H), 4.32 (d, J=11.3 Hz, 1H), 4.02 (m, 2H), 3.30 (m, 1H), 3.11 (m, 2H), 2.69 (t, J=6.7 Hz, 1H), 1.76 (m, 2H), 1.50 (m, 2H), 1.05 (d, J=6.8 Hz, 3H).

The synthesis of 1-(3-acrylamidobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-27)

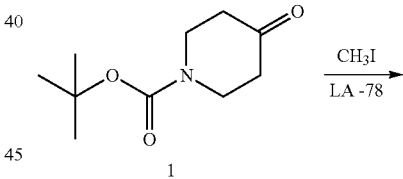

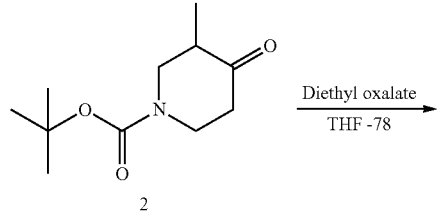

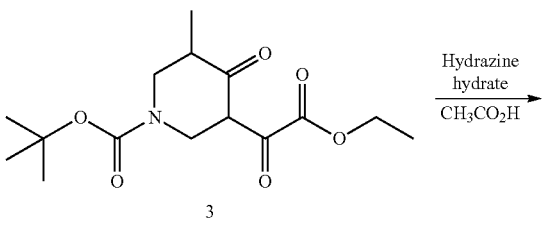

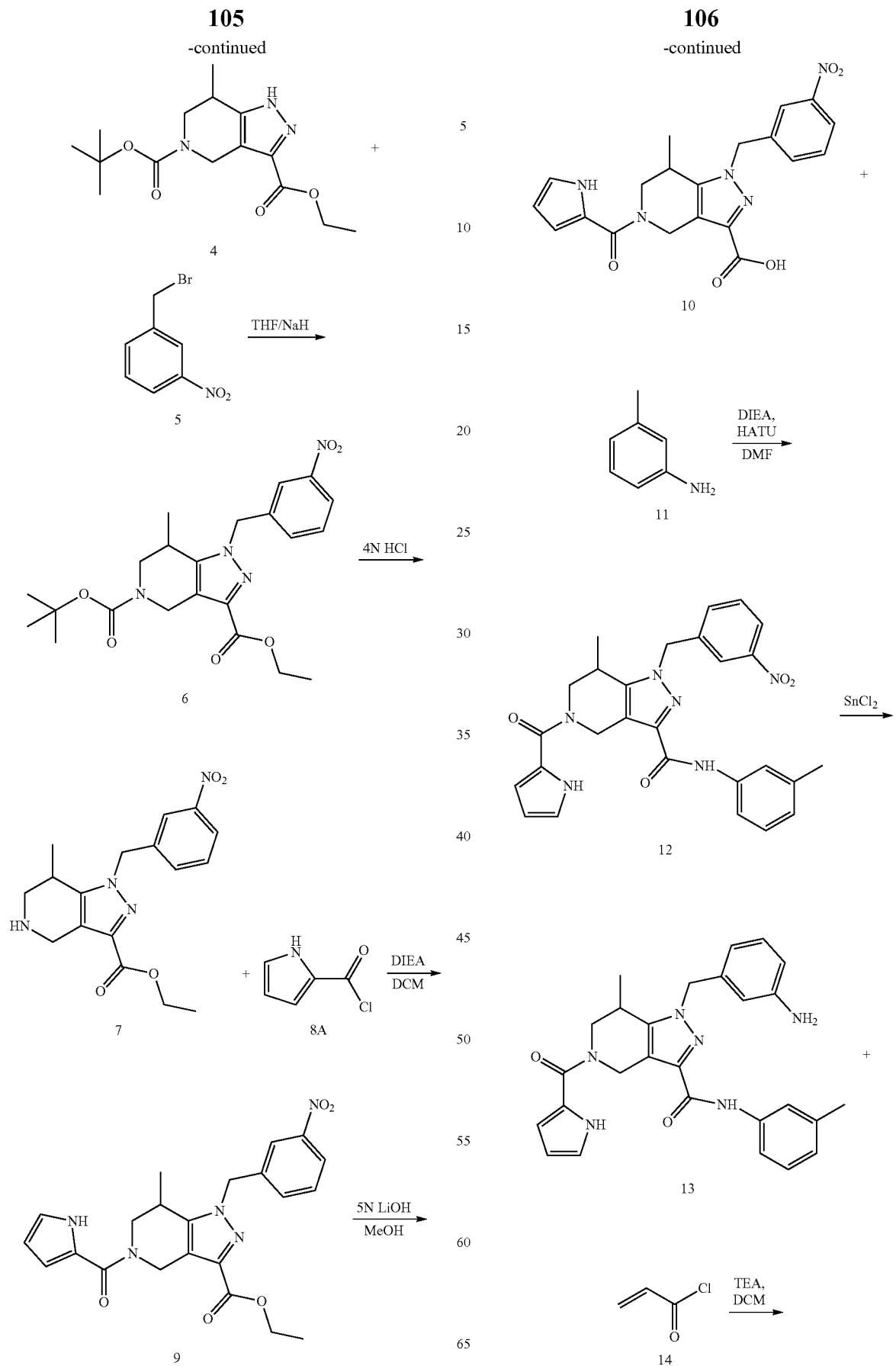

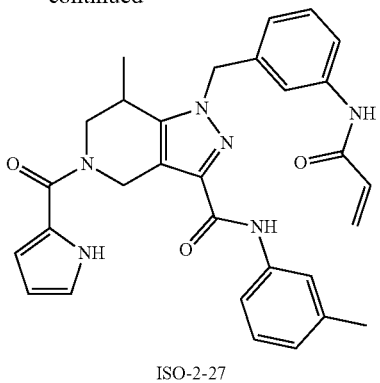

ISO-2-27

5-(tert-butyl)-3-ethyl-7-methyl-1-(3-nitrobenzyl)-1,4,6,7-tetrahydro-5H-pyrazolo[4,3-c]pyridine-3,5-dicarboxylate (6) To a solution of 5-(tert-butyl)-3-ethyl 7-methyl-1,4,6,7-tetrahydro-5H-pyrazolo[4,3-c]pyridine-3,5-dicarboxylate (4) (1.24 g, 4 mmol) in dry THF (10 mL) was added NaH (60% wt dispersion in mineral oil, 0.2 g, 4.8 mmol) with stirring under nitrogen. After 1 h, 1-(bromomethyl)-3-nitrobenzene (1.04 g, 4 mmol) was added and the reaction mixture was stirred 4 h under nitrogen. The reaction mixture was quenched with water and the pH was adjusted to 6.0 with 1 N HCl. The mixture was diluted with brine and extracted with ethyl acetate. The combined extracts were dried over $Na_2SO_4$, filtered and concentrated under reduced pressure. The residue was purified by silica gel chromatography. The appropriate fractions were combined, concentrated under reduced pressure and the residue was dried to afford the product. MS m/z 445[M+H]$^+$.

Ethyl-7-methyl-1-(3-nitrobenzyl)-4,5,6,7-tetrahydro-1H-pyrazolo[4,3-c]pyridine-3-carboxylate (7) To a round-bottom flask containing 5-(tert-butyl) 3-ethyl 7-methyl-1-(3-nitrobenzyl)-1,4,6,7-tetrahydro-5H-pyrazolo[4,3-c]pyridine-3,5-dicarboxylate (6) (1 g, 2.25 mmol) was added with HCl (4 N in ethyl acetate, 10 mL). The resulting clear solution was stirred at room temperature. The reaction mixture was concentrated under reduced pressure and the resulting residue was dried to afford the product (0.85 g, 100%) as a yellow solid.

Ethyl-7-methyl-1-(3-nitrobenzyl)-5-(1H-pyrrole-2-carbonyl)-4,5,6,7-tetrahydro-1H-pyrazolo[4,3-c]pyridine-3-carboxylate (9) To a solution of ethyl 7-methyl-1-(3-nitrobenzyl)-4,5,6,7-tetrahydro-1H-pyrazolo[4,3-c]pyridine-3-carboxylate (7) (0.85 g, 2.1 mmol) in DCM (10 mL) was added DIEA (0.67 g, 5.2 mmol) and 1H-pyrrole-2-carbonyl chloride (8A) (0.6 g, 2.5 mmol) at 0° C. The reaction mixture was diluted with water and saturated aqueous NaHCO$_3$ and extracted with DCM. The organic layer was washed with brine and concentrated under reduced pressure and the residue was purified by silica gel chromatography to afford the compound as a yellow solid (0.76 g, 80%). MS m/z 438 [M+H]$^+$.

7-methyl-1-(3-nitrobenzyl)-5-(1H-pyrrole-2-carbonyl)-4,5,6,7-tetrahydro-1H-pyrazolo[4,3-c]pyridine-3-carboxylic acid (10) To a solution of ethyl 7-methyl-1-(3-nitrobenzyl)-5-(1H-pyrrole-2-carbonyl)-4,5,6,7-tetrahydro-1H-pyrazolo[4,3-c]pyridine-3-carboxylate (9) (0.1 g, 0.22 mmol) in MeOH (3 mL) was added with 5N LiOH (1 mL). The clear solution was stirred at room temperature for 1 h. The reaction mixture was added with water and pH was adjusted to 6.0 with 1N HCl. The resulting precipitate was collected by filtration and dried to afford the product (70 mg, 74.5%) as a white solid. MS m/z 410 [M+H]$^+$.

7-methyl-1-(3-nitrobenzyl)-5-(1H-pyrrole-2-carbonyl)-N-(m-tolyl)-4,5,6,7-tetrahydro-1H-pyrazolo[4,3-c]pyridine-3-carboxamide (12) To a solution of 7-methyl-1-(3-nitrobenzyl)-5-(1H-pyrrole-2-carbonyl)-4,5,6,7-tetrahydro-1H-pyrazolo[4,3-c]pyridine-3-carboxylic acid (10) (70 mg, 0.16 mmol) in DMF (2 mL) were added m-toluidine (25 mg, 0.18 mmol), HATU (92 mg, 0.24 mmol) and DIEA (42 mg, 0.32 mmol). The mixture was stirred at room temperature under nitrogen. After 1 h, the reaction mixture was added with water and the resulting precipitate was collected by filtration and dried to afford compound (12) (74 mg, 85%) as a white solid. MS m/z 499[M+H]$^+$.

1-(3-aminobenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) To a solution of 7-methyl-1-(3-nitrobenzyl)-5-(1H-pyrrole-2-carbonyl)-N-(m-tolyl)-4,5,6,7-tetrahydro-1H-pyrazolo[4,3-c]pyridine-3-carboxamide (12) (0.4 g, 0.73 mmol) in ethyl acetate/methanol (4/1)(10 mL) was added stannous chloride (1.11 g, 5.86 mmol). The resulting mixture was heated at 80° C. The reaction mixture was added DCM and the pH adjusted to 8 with saturated aqueous NaHCO$_3$ and extracted with DCM. The organic layer was washed with brine and dried. Then concentrated under reduced pressure and the residue was purified by silica gel chromatography to afford the compound as a white solid (0.36 g, 95.5%). MS m/z 469[M+H]$^+$.

1-(3-acrylamidobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-27) To a solution of 1-(3-aminobenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) (0.36 g, 0.7 mmol) in DCM (5 mL) was added DIEA (0.18 g, 1.4 mmol) and acryloyl chloride (95 mg, 1.05 mmol) at 0° C. The reaction mixture was diluted with water and saturated aqueous NaHCO$_3$ and extracted with DCM. The organic layer was washed with brine and then concentrated under reduced pressure and the residue was purified by silica gel chromatography to afford the compound as a white solid (60 mg, 15%). MS m/z 523 [M+H]$^+$. $^1$H NMR (400 MHz, DMSO) δ 11.54 (s, 1H), 10.40 (s, 1H), 9.88 (s, 1H), 7.69 (m, 2H), 7.58 (d, J=8.2 Hz, 1H), 7.52 (s, 1H), 7.31 (t, J=7.9 Hz, 1H), 7.18 (t, J=7.8 Hz, 1H), 6.88 (m, 3H), 6.60 (s, 1H), 6.49 (m, 1H), 6.27-6.15 (m, 2H), 5.72 (d, J=10.1 Hz, 1H), 5.44 (q, J=16.2 Hz, 2H), 5.32 (d, J=16.6 Hz, 1H), 4.67 (br, 1H), 4.36 (d, J=11.6 Hz, 1H), 3.40 (br, 1H), 3.18 (s, 1H), 2.29 (s, 3H), 1.11 (d, J=6.8 Hz, 3H).

The synthesis of 1-(4-acrylamido-3-methylbenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-28)

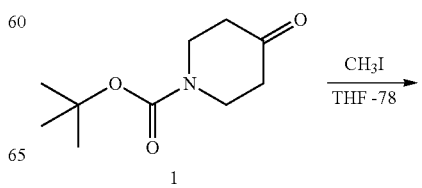

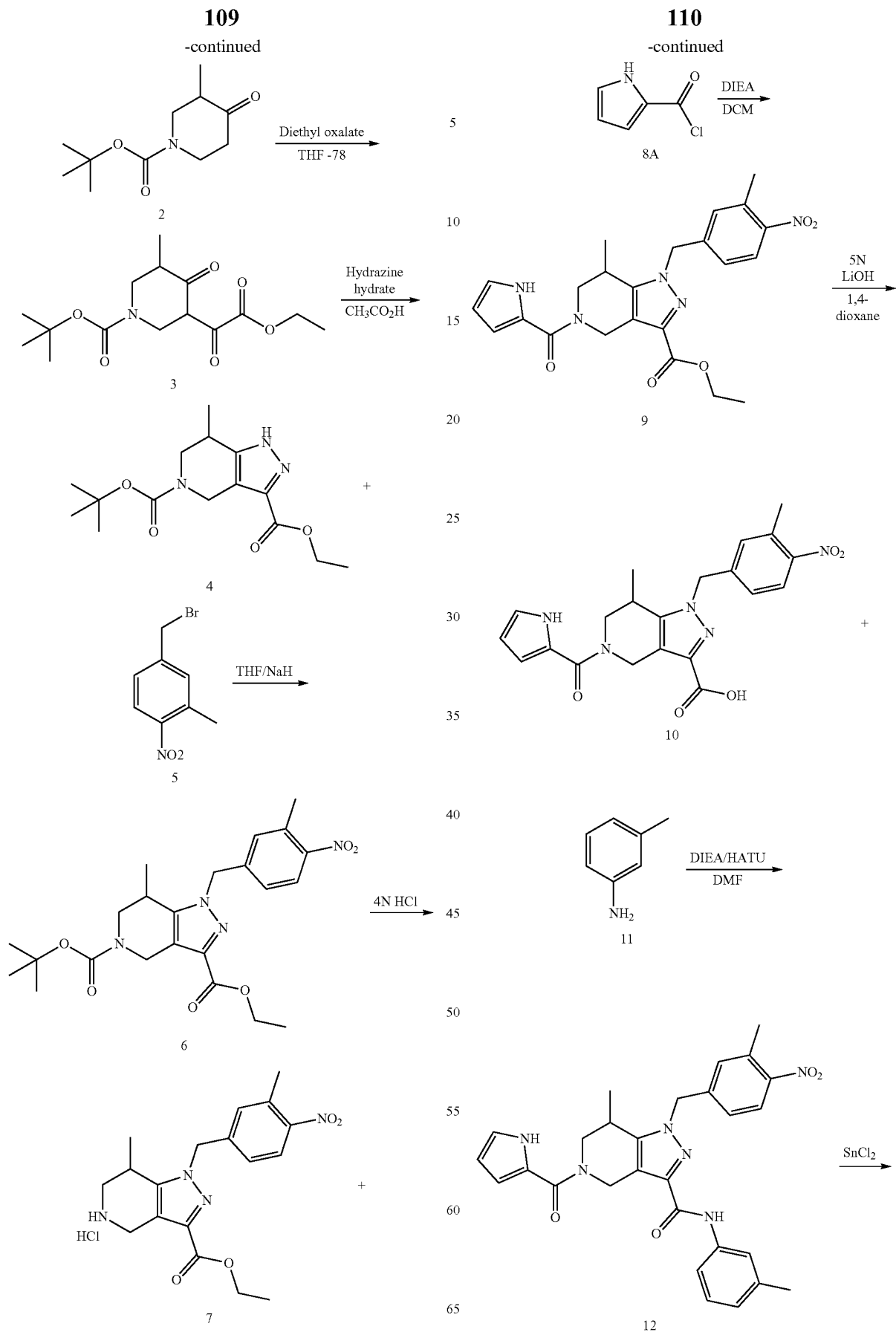

-continued

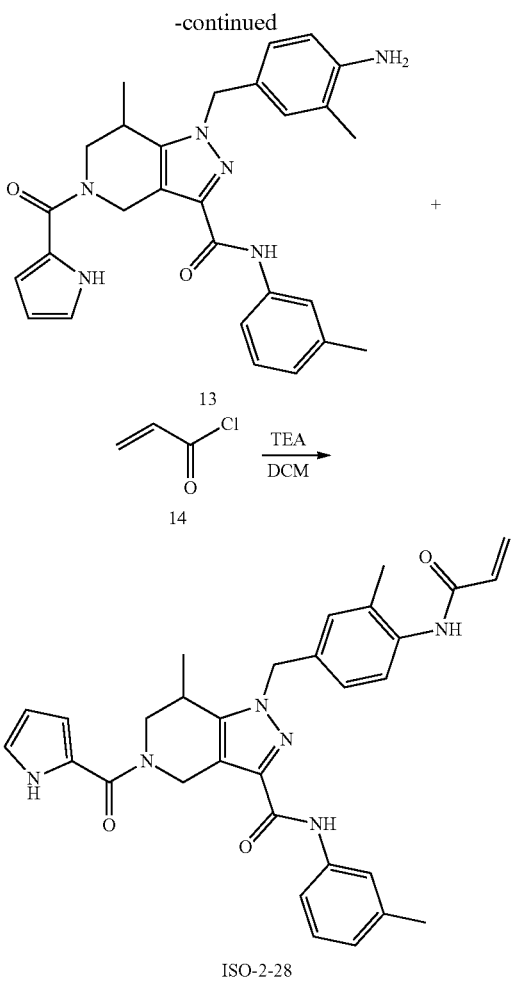

5-(tert-butyl)-3-ethyl-7-methyl-1-(3-methyl-4-nitrobenzyl)-1,4,6,7-tetrahydro-5H-pyrazolo[4,3-c]pyridine-3,5-dicarboxylate (6) To a solution of 5-(tert-butyl) 3-ethyl 7-methyl-1,4,6,7-tetrahydro-5H-pyrazolo[4,3-c]pyridine-3,5-dicarboxylate (4) (1.5 g, 4.85 mmol) in dry THF (20 mL) was added NaH (60% wt dispersion in mineral oil, 0.23 g, 5.82 mmol) with stirring under nitrogen. After 1 h, 4-(bromomethyl)-2-methyl-1-nitrobenzene (1.26 g, 4.85 mmol) was added and the reaction mixture was stirred for 4 h under nitrogen. The reaction mixture was quenched with water and the pH was adjusted to 6.0 with 1 N HCl. The mixture was diluted with brine and extracted with ethyl acetate. The organic layer was dried and concentrated. The residue was purified by silica gel chromatography to afford 5-(tert-butyl) 3-ethyl 7-methyl-1-(3-methyl-4-nitrobenzyl)-1,4,6,7-tetrahydro-5H-pyrazolo[4,3-c]pyridine-3,5-dicarboxylate (0.91 g, 40.6%) as a light yellow solid. MS m/z 459[M+H]$^+$.

Ethyl-7-methyl-1-(3-methyl-4-nitrobenzyl)-4,5,6,7-tetrahydro-1H-pyrazolo[4,3-c]pyridine-3-carboxylate (7) To a round-bottom flask containing 5-(tert-butyl) 3-ethyl 7-methyl-1-(3-methyl-4-nitrobenzyl)-1,4,6,7-tetrahydro-5H-pyrazolo[4,3-c]pyridine-3,5-dicarboxylate (6) (0.91 g, 2 mmol) was added with HCl (4 N in ethyl acetate, 5 mL). The resulting clear solution was stirred at room temperature. The reaction mixture was concentrated under reduced pressure and the resulting residue was dried to afford ethyl 7-methyl-1-(3-methyl-4-nitrobenzyl)-4,5,6,7-tetrahydro-1H-pyrazolo[4,3-c]pyridine-3-carboxylate (0.78 g, 100%) as a yellow solid.

Ethyl-7-methyl-1-(3-methyl-4-nitrobenzyl)-5-(1H-pyrrole-2-carbonyl)-4,5,6,7-tetrahydro-1H-pyrazolo[4,3-c]pyridine-3-carboxylate (9) To a solution of ethyl 7-methyl-1-(3-methyl-4-nitrobenzyl)-4,5,6,7-tetrahydro-1H-pyrazolo[4,3-c]pyridine-3-carboxylate (7) (0.8 g, 2.5 mmol) in DCM (10 mL) was added DIEA (0.65 g, 6.25 mmol) and 1H-pyrrole-2-carbonyl chloride (0.31 g, 3 mmol) at 0° C. for 10 min. The reaction mixture was diluted with water and saturated aqueous NaHCO$_3$ and extracted with DCM. The organic layer was washed with brine and dried. Then concentrated under reduced pressure and the residue was purified by silica gel chromatography to afford the compound as a yellow solid (0.8 g, 73%). MS m/z 452[M+H]$^+$.

7-methyl-1-(3-methyl-4-nitrobenzyl)-5-(1H-pyrrole-2-carbonyl)-4,5,6,7-tetrahydro-1H-pyrazolo[4,3-c]pyridine-3-carboxylic acid (10) To a solution of ethyl 7-methyl-1-(3-methyl-4-nitrobenzyl)-5-(1H-pyrrole-2-carbonyl)-4,5,6,7-tetrahydro-1H-pyrazolo[4,3-c]pyridine-3-carboxylate (9) (0.8 g, 1.76 mmol) in 1,4-dioxane (5 mL) was added with 5 N LiOH (5 mL). The clear solution was stirred at room temperature. The reaction mixture was added with water and pH was adjusted to 6.0 with 1 N HCl. The resulting precipitate was collected by filtration and dried to afford 7-methyl-1-(3-methyl-4-nitrobenzyl)-5-(1H-pyrrole-2-carbonyl)-4,5,6,7-tetrahydro-1H-pyrazolo[4,3-c]pyridine-3-carboxylic acid (0.7 g, 92%) as a white solid. MS m/z 424[M+H]$^+$.

7-methyl-1-(3-methyl-4-nitrobenzyl)-5-(1H-pyrrole-2-carbonyl)-N-(m-tolyl)-4,5,6,7-tetrahydro-1H-pyrazolo[4,3-c]pyridine-3-carboxamide (12) To a solution of 7-methyl-1-(3-methyl-4-nitrobenzyl)-5-(1H-pyrrole-2-carbonyl)-4,5,6,7-tetrahydro-1H-pyrazolo[4,3-c]pyridine-3-carboxylic acid (10) (0.32 g, 0.75 mmol) in DMF (5 mL) were added m-toluidine (0.1 g, 0.9 mmol), HATU (0.43 g, 1.125 mmol) and DIEA (0.2 g, 1.5 mmol). The mixture was stirred at room temperature under nitrogen. After 1 h, the reaction mixture was added with water and the resulting precipitate was collected by filtration and dried to afford compound (12) (0.36 g, 95%) as a white solid. MS m/z 513[M+H]$^+$.

1-(4-amino-3-methylbenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) To a solution of 7-methyl-1-(3-methyl-4-nitrobenzyl)-5-(1H-pyrrole-2-carbonyl)-N-(m-tolyl)-4,5,6,7-tetrahydro-1H-pyrazolo[4,3-c]pyridine-3-carboxamide (12) (0.36 g, 0.7 mmol) in ethyl acetate/methanol (4/1, 10 mL) was added Tin(II) chloride (1.12 g, 5.6 mmol). The resulting mixture was heated at 80° C. overnight. The reaction mixture was added DCM and the pH was adjusted to 8.0 with saturated aqueous NaHCO$_3$ and extracted with DCM. The organic layer was washed with brine and dried. Then concentrated under reduced pressure and the residue was purified by silica gel chromatography to afford the compound as a white solid (0.3 g, 88%). MS m/z 483[M+H]$^+$.

1-(4-acrylamido-3-methylbenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-28) To a solution of 1-(4-amino-3-methylbenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) (0.3 g, 0.62 mmol) in DCM (10 mL) was added TEA (0.19 g, 1.86 mmol) and acryloyl chloride (0.17 g, 1.86 mmol) at 0° C. The reaction mixture was diluted with water and saturated aqueous NaHCO$_3$ and extracted with DCM. The organic layer was washed with brine and dried. Then concentrated under reduced pressure and the residue was purified by silica gel chromatography to afford the compound as a white solid (86 mg, 26%). MS m/z 537 [M+], H NMR (400 MHz, DMSO), δ 11.54 (s, 1H), 9.88 (s, 1H), 9.53 (s, 1H), 7.69 (s, 1H), 7.56 (d, J=8.5 Hz, 1H), 7.46 (d, J=8.2 Hz, 1H), 7.19 (t, J=7.8 Hz, 1H), 7.10 (s, 1H), 6.99 (d, J=8.2 Hz, 1H), 6.91 (m, 2H), 6.56 (m, 1H), 6.49 (m, 1H), 6.28-6.15 (m, 2H), 5.73 (d, J=10.2 Hz, 1H), 5.40 (q, J=16.0 Hz, 2H), 5.31 (d, J=16.2 Hz, 1H), 4.67 (br, 1H), 4.36 (d, J=11.0 Hz, 1H), 3.30 (m, 1H), 3.18 (s, 1H), 2.29 (s, 3H), 2.19 (s, 3H), 1.12 (d, J=6.8 Hz, 3H).
The synthesis of N-(3-acrylamido-4-chlorophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-29)
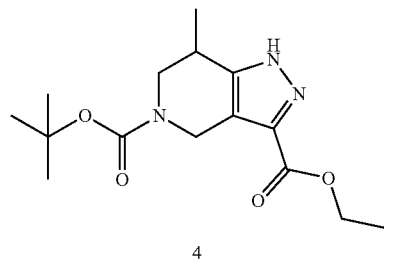
4
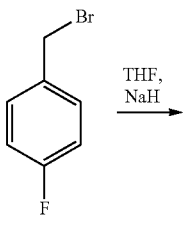
5
THF, NaH →
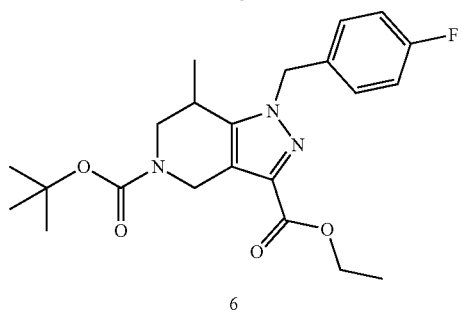
6
HCl/EA →
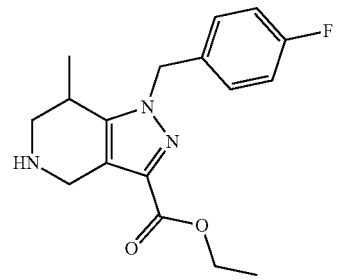
7
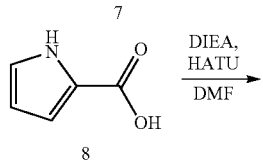
8
DIEA, HATU, DMF →
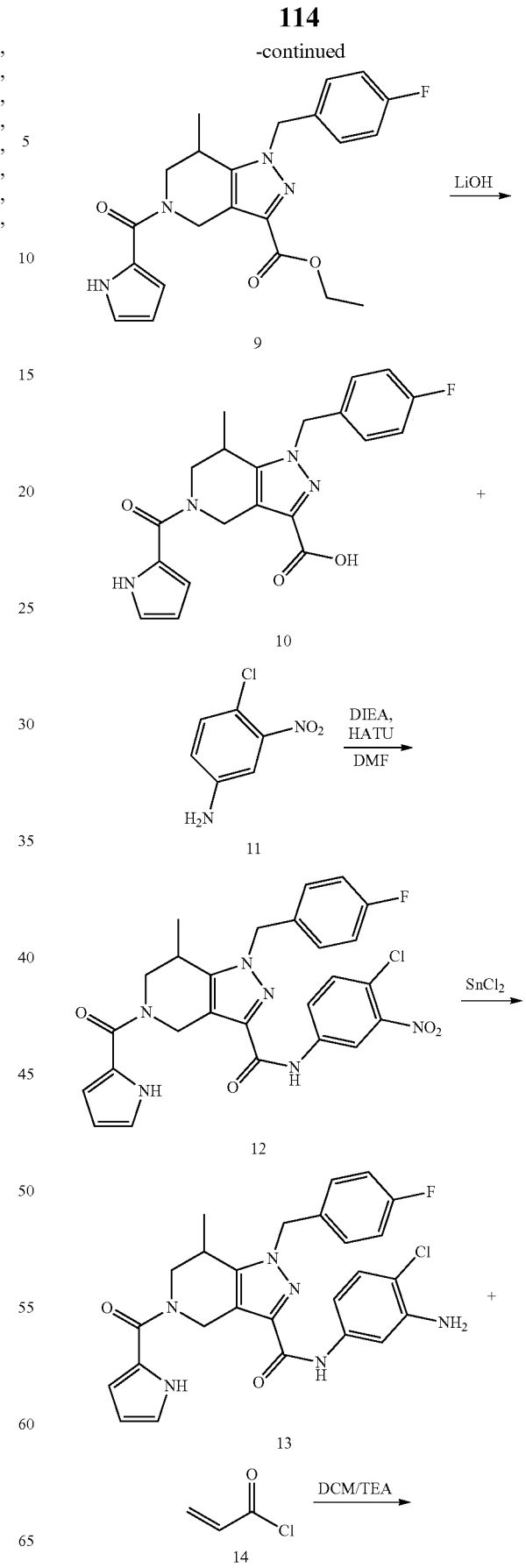

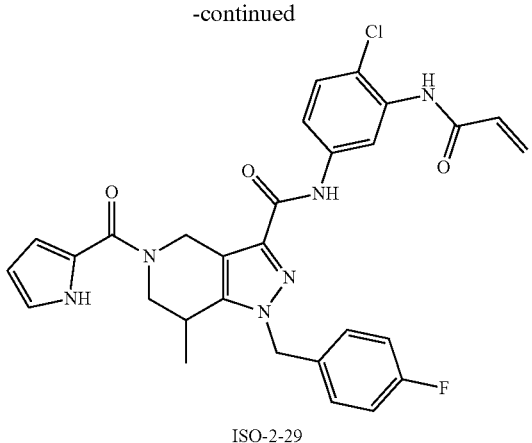

ISO-2-29

N-(4-chloro-3-nitrophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.1 g, 0.26 mmol) in DMF (5 mL) were added 4-chloro-3-nitroaniline (32 mg, 0.28 mmol), HATU (0.15 g, 0.39 mmol) and DIEA (0.37 g, 0.52 mmol). The mixture was stirred at room temperature under nitrogen. After 1 h, the reaction mixture was added with water and the resulting precipitate was collected by filtration and dried to afford compound (12) (115 mg, 82%) as a white solid. MS m/z 537[M+H]⁺.

N-(3-amino-4-chlorophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) To a solution of N-(4-chloro-3-nitrophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) (0.4 g, 0.7 mmol) in ethyl acetate/methanol (4/1)(10 mL) was added stannous chloride (1.12 g, 5.6 mmol). The resulting mixture was heated at 80° C. and dichloromethane was added, the pH adjusted to 8 and extracted with dichloromethane. The organic layer was washed with brine, dried over Na₂SO₄, concentrated under reduced pressure and the residue was purified by silica gel chromatography to afford the compound as a white solid (0.31 g, 82%). MS m/z507[M+H]⁺.

N-(3-acrylamido-4-chlorophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-29) To a solution of N-(3-amino-4-chlorophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) (110 mg, 0.21 mmol) in dichloromethane (5 mL) was added TEA (48 mg, 0.42 mmol) and acryloyl chloride (35 mg, 0.33 mmol) at 0° C. The reaction mixture was diluted with water and saturated aqueous NaHCO₃. Dichloromethane was added and the organic layer was washed with brine and dried. Then concentrated under reduced pressure and the residue was purified by silica gel chromatography to afford the compound as a white solid (28 mg, 20%). MS m/z 561[M+H]⁺. ¹H NMR (400 MHz, DMSO) δ 11.54 (s, 1H), 10.24 (s, 1H), 9.79 (s, 1H), 8.29 (d, J=2.3 Hz, 1H), 7.69 (dd, J=8.8, 2.5 Hz, 1H), 7.43 (d, J=8.8 Hz, 1H), 7.27 (m, 2H), 7.19 (m, 2H), 6.91 (m, 1H), 6.69-6.55 (m, 2H), 6.28 (dd, J=17.2, 2.0 Hz, 1H), 6.17 (m, 1H), 5.79 (dd, J=10.0, 1.6 Hz, 1H), 5.45 (q, J=16.0 Hz, 2H), 5.30 (d, J=16.4 Hz, 1H), 4.67 (br, 1H), 4.35 (d, J=12.0 Hz, 1H), 3.37 (m, 1H), 3.17 (m, 1H), 1.08 (d, J=6.8 Hz, 3H).

The synthesis of N-(3-acrylamido-4-methoxyphenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-30)

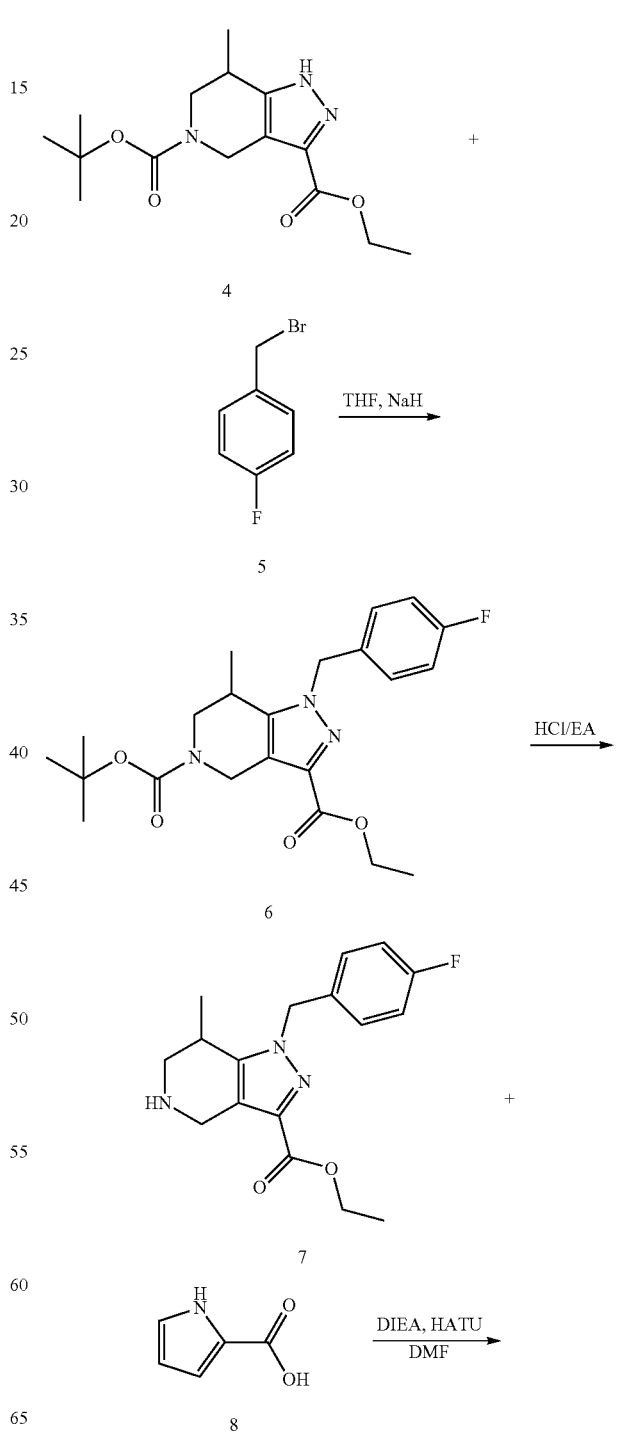

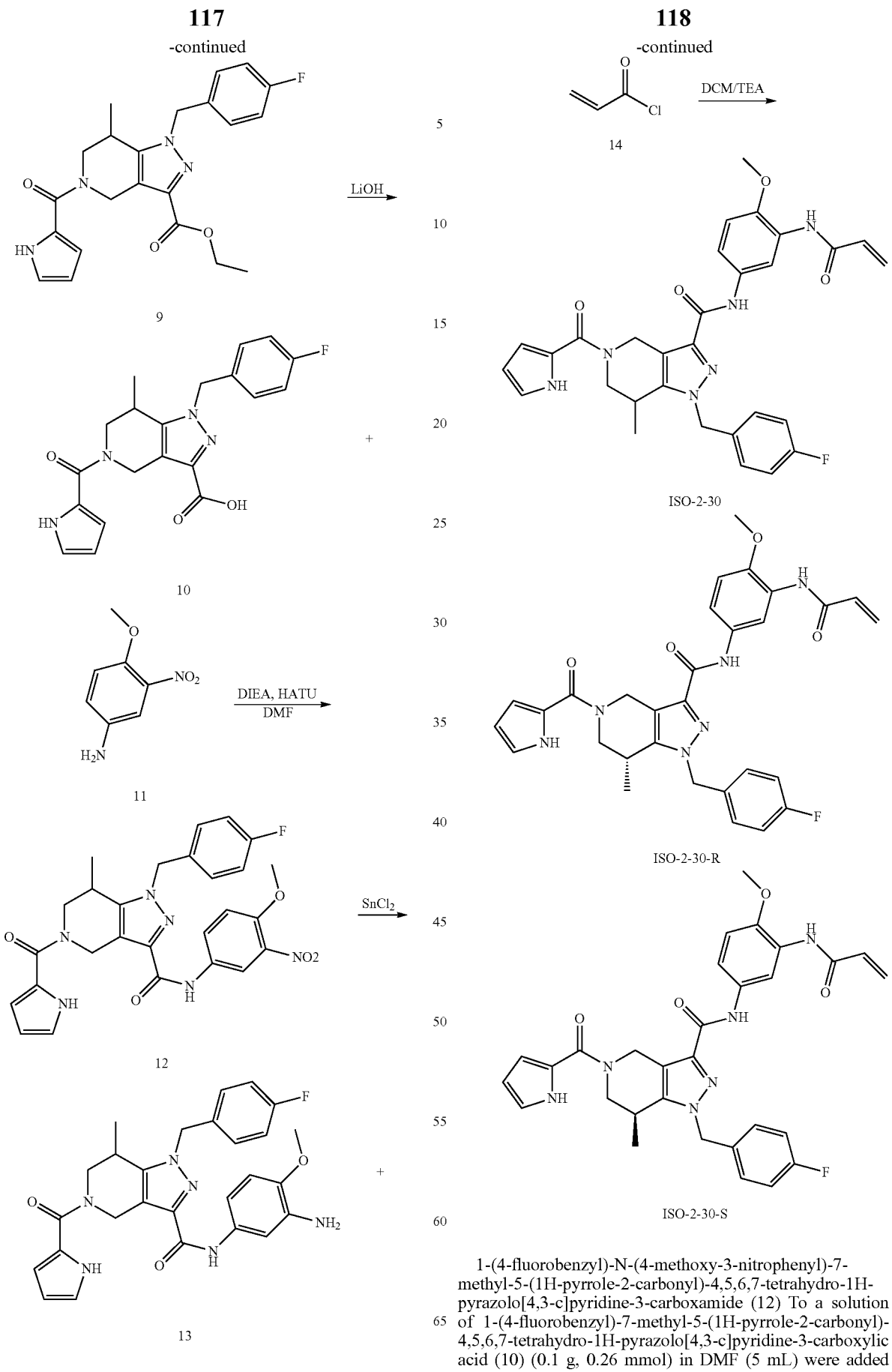
1-(4-fluorobenzyl)-N-(4-methoxy-3-nitrophenyl)-7-methyl-5-(1H-pyrrole-2-carbonyl)-4,5,6,7-tetrahydro-1H-pyrazolo[4,3-c]pyridine-3-carboxamide (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.1 g, 0.26 mmol) in DMF (5 mL) were added 4-methoxy-3-nitroaniline (32 mg, 0.28 mmol), HATU (0.15 g, 0.39 mmol) and DIEA (0.37 g, 0.52 mmol). The mixture was stirred at room temperature under nitrogen. After 1 h, the reaction mixture was added with water and the resulting precipitate was collected by filtration and dried to afford compound (12) (105 mg, 78%) as a white solid. MS m/z 533[M+H]$^+$.

N-(3-amino-4-methoxyphenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) To a solution of 1-(4-fluorobenzyl)-N-(4-methoxy-3-nitrophenyl)-7-methyl-5-(1H-pyrrole-2-carbonyl)-4,5,6,7-tetrahydro-1H-pyrazolo[4,3-c]pyridine-3-carboxamide (12) (0.35 g, 0.66 mmol) in ethyl acetate/methanol (4/1)(10 mL) was added stannous chloride (1.12 g, 5.6 mmol). The resulting mixture was heated at 80° C. DCM was added and pH was adjusted to 8. The organic layer was washed with brine, dried over Na$_2$SO$_4$, concentrated under reduced pressure and the residue was purified by silica gel chromatography to afford the compound as a white solid (0.23 g, 75%). MS m/z503[M+H]$^+$.

N-(3-acrylamido-4-chlorophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-30) To a solution of N-(3-amino-4-methoxyphenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) (110 mg, 0.21 mmol) in dichloromethane (5 mL) was added TEA (48 mg, 0.42 mmol) and acryloyl chloride (35 mg, 0.33 mmol) at 0° C. The reaction mixture was diluted with water and saturated aqueous NaHCO$_3$. Dichloromethane was added and the organic layer was washed with brine and dried. Then concentrated under reduced pressure and the residue was purified by silica gel chromatography to afford the compound as a white solid (42 mg, 36%). MS m/z 557[M+H]$^+$. $^1$H NMR (400 MHz, DMSO) δ 11.53 (s, 1H), 9.87 (s, 1H), 9.37 (s, 1H), 8.44 (s, 1H), 7.51 (dd, J=8.9, 2.5 Hz, 1H), 7.27 (m, 2H), 7.20 (m, 2H), 7.00 (d, J=9.0 Hz, 1H), 6.91 (m, 1H), 6.69 (m, 1H), 6.59 (m, 1H), 6.28 (dd, J=17.2, 2.0 Hz, 1H), 6.17 (m, 1H), 5.79 (dd, J=10.0, 1.6 Hz, 1H), 5.45 (q, J=16.4 Hz, 2H), 5.30 (d, J=16.4 Hz, 1H), 4.67 (br, 1H), 4.34 (d, J=12.0 Hz, 1H), 3.83 (s, 3H), 3.39 (s, 1H), 3.22-3.10 (m, 1H), 1.08 (d, J=6.8 Hz, 3H).

ISO-2-30-R and ISO-2-30-S were obtained by HPLC purification on a chiral column.

The synthesis of N-(1-acryloylindolin-6-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-31)

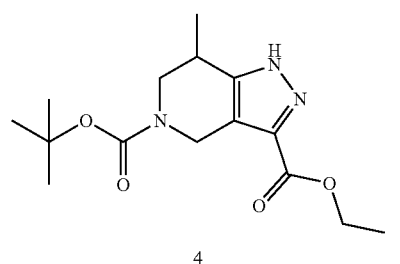

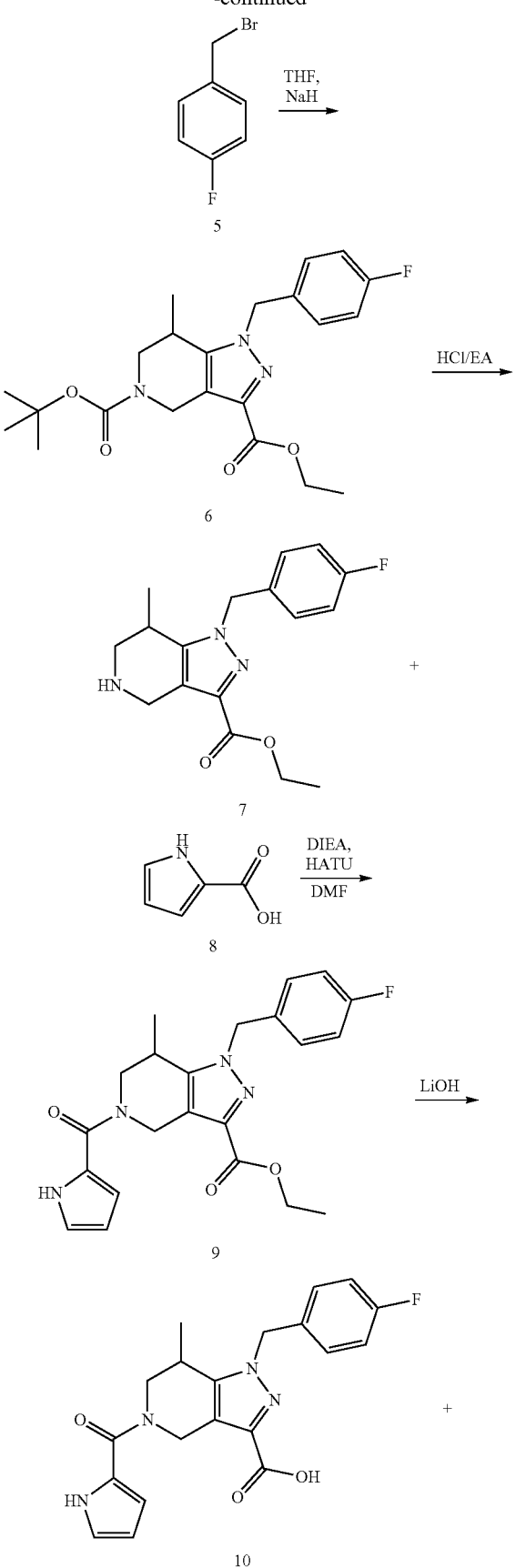

-continued

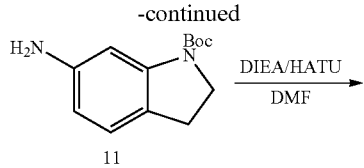

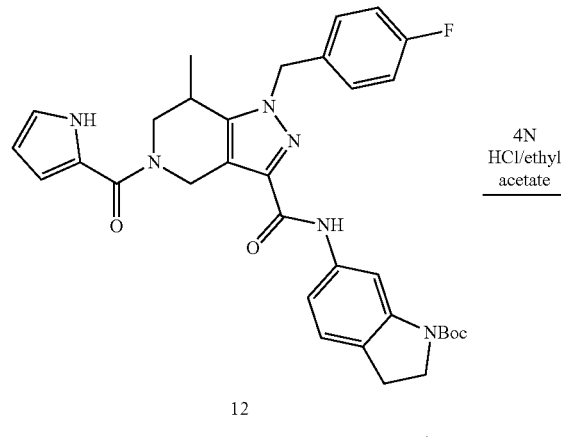

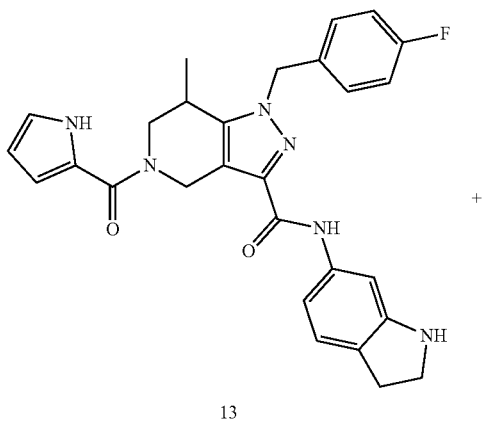

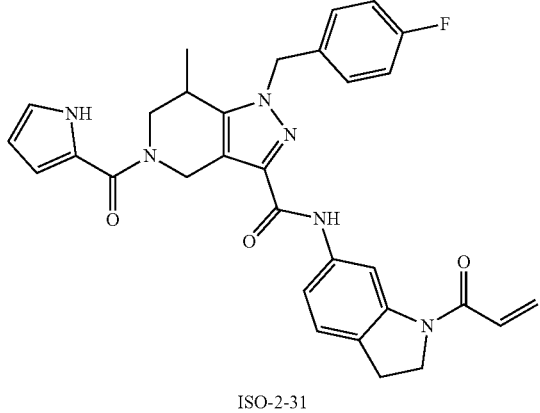

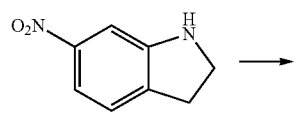

-continued

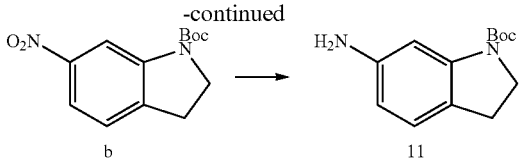

Tert-butyl 6-nitroindoline-1-carboxylate (b) To a solution of 6-nitroindoline (a) (3 g, 18.3 mmol) in DCM (30 mL) was added di-tert-butyl dicarbonate (4.8 g, 22 mmol) and TEA (3.7 g, 36.6 mmol). The solution was stirred for 5 h at room temperature then washed with water and brine. The organic layer was dried, filtered and concentrated. Silica gel column chromatography provided tert-butyl 6-nitroindoline-1-carboxylate (b) as a white solid (2.4 g, 50%).

Tert-butyl 6-aminoindoline-1-carboxylate(11) A mixture of tert-butyl 6-nitroindoline-1-carboxylate (b) (2.4 g, 9.1 mmol) and 10% Pd-C (0.1 g) in MeOH (10 mL) is stirred under 1 atmosphere pressure of hydrogen for 2 h. The mixture is filtered and concentrated. Silica gel column chromatography provided tert-butyl 6-aminoindoline-1-carboxylate (11) as a solid (2 g, 94%). MS m/z235[M+H]$^+$.

Tert-butyl 6-(1-(4-fluorobenzyl)-7-methyl-5-(1H-pyrrole-2-carbonyl)-4,5,6,7-tetrahydro-1H-pyrazolo[4,3-c]pyridine-3-carboxamido)indoline-1-carboxylate(12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.2 g, 0.52 mmol) in DMF (5 mL) were added tert-butyl 6-aminoindoline-1-carboxylate (11) (0.13 g, 0.57 mmol), HATU (0.3 g, 0.78 mmol) and DIEA (0.13 g, 1.04 mmol). The mixture was stirred at room temperature under nitrogen. After 1 h, the reaction mixture was added water and the resulting precipitate was collected by filtration and dried on a lyophilizer overnight to afford tert-butyl 6-(1-(4-fluorobenzyl)-7-methyl-5-(1H-pyrrole-2-carbonyl)-4,5,6,7-tetrahydro-1H-pyrazolo[4,3-c]pyridine-3-carboxamido)indoline-1-carboxylate(12) as a white solid. MS m/z599[M+H]$^+$.

1-(4-fluorobenzyl)-N-(indolin-6-yl)-7-methyl-5-(1H-pyrrole-2-carbonyl)-4,5,6,7-tetrahydro-1H-pyrazolo[4,3-c]pyridine-3-carboxamide (13) To a round-bottom flask containing tert-butyl 6-(1-(4-fluorobenzyl)-7-methyl-5-(1H-pyrrole-2-carbonyl)-4,5,6,7-tetrahydro-1H-pyrazolo[4,3-c]pyridine-3-carboxamido)indoline-1-carboxylate(12) (0.33 g, 0.55 mmol) was added HCl (4 N in ethyl acetate, 10 mL). The resulting clear solution was stirred at room temperature for 3 h. The reaction mixture was concentrated under reduced pressure and the resulting residue was dried to constant weight under high vacuum to afford 1-(4-fluorobenzyl)-N-(indolin-6-yl)-7-methyl-5-(1H-pyrrole-2-carbonyl)-4,5,6,7-tetrahydro-1H-pyrazolo[4,3-c]pyridine-3-carboxamide (13) (0.27 g, 100%) as a solid. MS m/z499 [M+H]$^+$.

N-(1-acryloylindolin-6-yl)-1-(4-fluorobenzyl)-7-methyl-5-(1H-pyrrole-2-carbonyl)-4,5,6,7-tetrahydro-1H-pyrazolo[4,3-c]pyridine-3-carboxamide(ISO-2-31) To a solution of 1-(4-fluorobenzyl)-N-(indolin-6-yl)-7-methyl-5-(1H-pyrrole-2-carbonyl)-4,5,6,7-tetrahydro-1H-pyrazolo[4,3-c]pyridine-3-carboxamide (13) (0.27 g, 0.54 mmol) in DCM (5 mL) was added DIEA (140 mg, 1.08 mmol) and acryloyl chloride (98 mg, 1.08 mmol) at −20° C. for 5 min. The reaction mixture was diluted with water and saturated aqueous NaHCO$_3$ and extracted with two portions of DCM. The organic layer was washed with brine, dried and concentrated under reduced pressure and the residue was purified by silica gel chromatography to afford the compound as a white solid.

MS m/z 553[M+H]+. 1H NMR (400 MHz, DMSO) δ 11.52 (s, 1H), 9.90 (s, 1H), 8.64 (s, 1H), 7.44 (d, J=7.7 Hz, 1H), 7.28 (m, 2H), 7.23-7.13 (m, 3H), 6.91 (m, 1H), 6.75 (m, 1H), 6.60 (m, 1H), 6.31 (d, J=17.2, 2.0 Hz, 1H), 6.18 (m, 1H), 5.82 (dd, J=10.2, 1.6 Hz, 1H), 5.44 (q, J=16.4 Hz, 2H), 5.30 (d, J=16.8 Hz, 1H), 4.68 (br, 1H), 4.35 (d, J=12.0 Hz, 1H), 4.22 (s, 2H), 3.38 (m, 1H), 3.10 (m, 3H), 1.08 (d, J=6.8 Hz, 3H).
The synthesis of N-(3-acrylamidobenzyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-32)
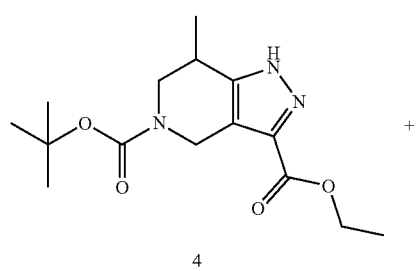
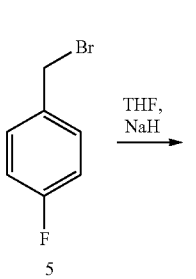
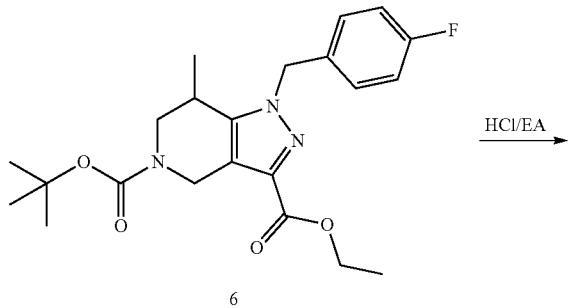
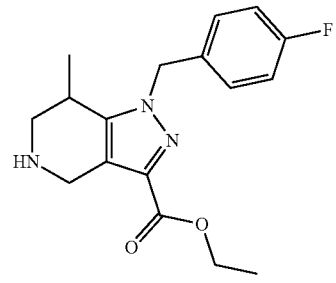
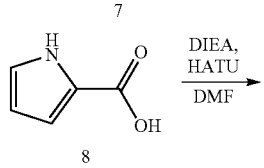
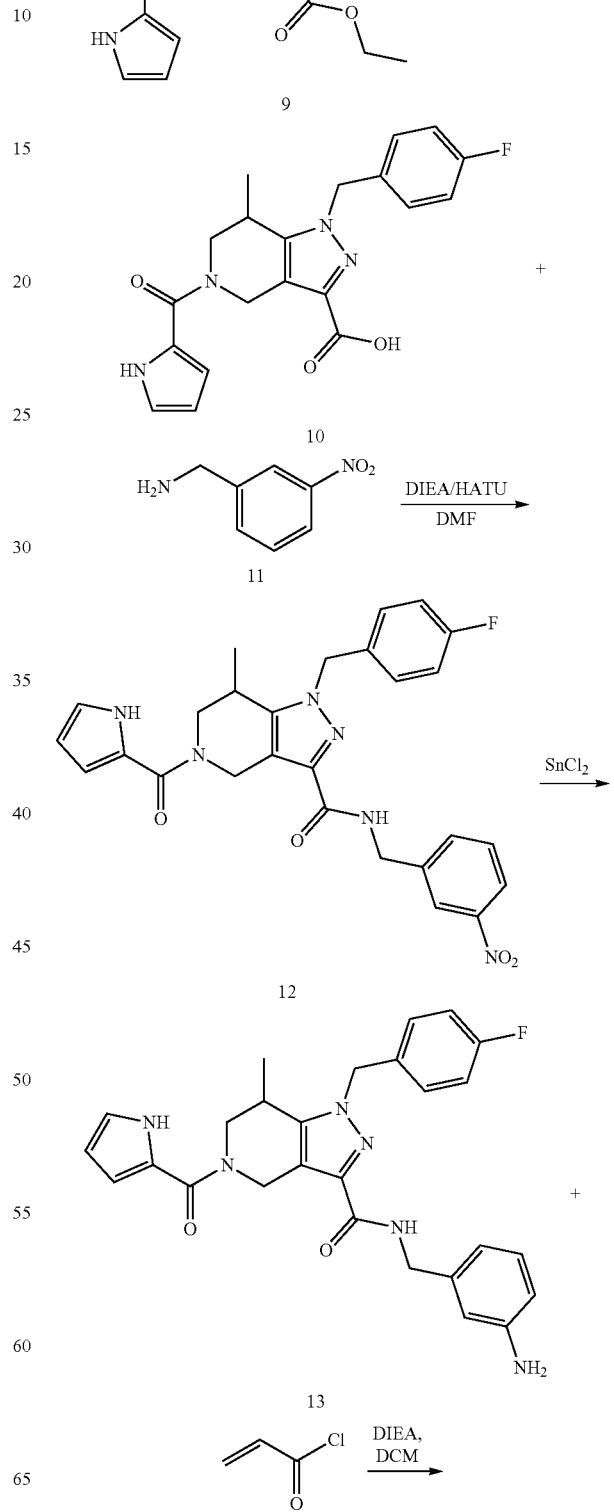

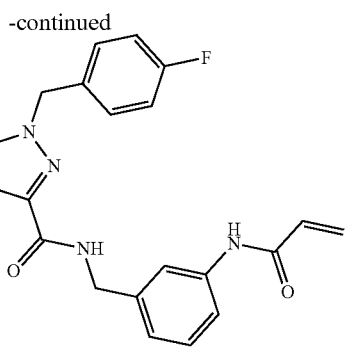

ISO-2-32

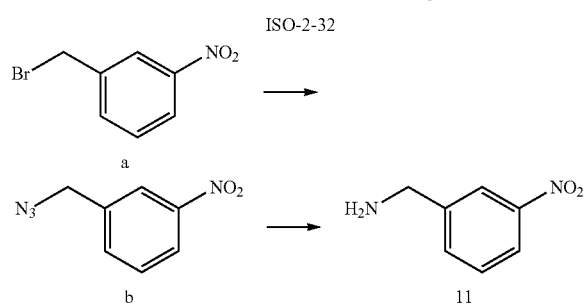

1-(azidomethyl)-3-nitrobenzene (b) A stock solution of 0.5 M NaN3 in DMSO was prepared after stirring for 24 h at room temperature. A 250 mL round-bottom flask equipped with a magnetic stir bar, was charged with a 0.5 M solution of NaN$_3$ (2.26 g, 34.7 mmol) in DMSO (70 mL) followed by 1-(bromomethyl)-3-nitrobenzene (5 g, 23.1 mmol). The mixture was stirred overnight at room temperature, treated with H$_2$O and stirred until it was cooled to room temperature. The mixture was extracted with ethyl acetate (3 times). The ethyl acetate extracts were combined, washed with H$_2$O and brine, dried, filtered and evaporated under reduced pressure.

(3-nitrophenyl)methanamine (11) A stirred mixture of 1-(azidomethyl)-3-nitrobenzene (4.15 g, 23.3 mmol), CeCl$_3$ (8.6 g, 34.9 mmol), and NaI (31.4 g, 209.7 mmol) in acetonitrile (230 mL) was stirred for 1 h at 100° C. The reaction mixture was concentrated under reduced pressure and the resulting residue was dried under high vacuum to provide (3-nitrophenyl)methanamine (11).

1-(4-fluorobenzyl)-7-methyl-N-(3-nitrobenzyl)-5-(1H-pyrrole-2-carbonyl)-4,5,6,7-tetrahydro-1H-pyrazolo[4,3-c]pyridine-3-carboxamide (12) To a solution of 1-(4-fluorobenzyl)-7-methyl-5-(1H-pyrrole-2-carbonyl)-4,5,6,7-tetrahydro-1H-pyrazolo[4,3-c]pyridine-3-carboxylic acid (10) (0.2 g, 0.52 mmol) in DMF (5 mL) were added (3-nitrophenyl)methanamine (11) (87 mg, 0.57 mmol), HATU (0.3 g, 0.78 mmol) and DIEA (0.13 g, 1.04 mmol). The mixture was stirred at room temperature under nitrogen. After 1 h, the reaction mixture was added water and the resulting precipitate was collected by filtration and dried on a lyophilizer overnight to afford 1-(4-fluorobenzyl)-7-methyl-N-(3-nitrobenzyl)-5-(1H-pyrrole-2-carbonyl)-4,5,6,7-tetrahydro-1H-pyrazolo[4,3-c]pyridine-3-carboxamide (12) as a white solid. MS m/z517[M+H]$^+$.

N-(3-aminobenzyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) To a solution of 1-(4-fluorobenzyl)-7-methyl-N-(3-nitrobenzyl)-5-(1H-pyrrole-2-carbonyl)-4,5,6,7-tetrahydro-1H-pyrazolo[4,3-c]pyridine-3-carboxamide (12) (0.3 g, 0.58 mmol) in ethyl acetate/methanol (4/1)(10 mL) was added SnCl$_2$ (0.88 g, 4.64 mmol). The resulting mixture was heated at 80° C. overnight. The reaction mixture was added DCM and the pH adjusted to ~8 with saturated aqueous NaHCO$_3$ and extracted with DCM. The organic layer was washed with brine, dried, concentrated under reduced pressure and the residue was purified by silica gel chromatography to afford the compound as a white solid. MS m/z487[M+H]$^+$.

N-(3-acrylamidobenzyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (ISO-2-32) To a solution of N-(3-aminobenzyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) (0.18 g, 0.37 mmol) in dichloromethane (5 mL) was added DIEA (96 mg, 0.74 mmol) and acryloyl chloride (67 mg, 0.74 mmol) at −20° C. for 5 min. The reaction mixture was diluted with water and saturated aqueous NaHCO$_3$ and extracted with dichloromethane (DCM). The organic layer was washed with brine, dried, concentrated under reduced pressure and the residue was purified by silica gel chromatography to afford N-(3-acrylamidobenzyl)-1-(4-fluorobenzyl)-7-methyl-5-(1H-pyrrole-2-carbonyl)-4,5,6,7-tetrahydro-1H-pyrazolo[4,3-c]pyridine-3-carboxamide as a white solid. MS m/z541[M+H]$^+$. $^1$H NMR (400 MHz, DMSO) δ 11.50 (s, 1H), 10.10 (s, 1H), 8.62 (t, J=6.3 Hz, 1H), 7.62 (d, J=8.2 Hz, 1H), 7.52 (s, 1H), 7.28-7.21 (m, 3H), 7.18 (m, 2H), 7.00 (d, J=7.8 Hz, 1H), 6.90 (m, 1H), 6.56 (m, 1H), 6.43 (m, 1H), 6.25 (dd, J=17.2, 2.0 Hz, 1H), 6.15 (m, 1H), 5.73 (m, 1H), 5.37 (q, J=16.4 Hz, 2H), 5.26 (d, J=16.4 Hz, 1H), 4.62 (br, 1H), 4.38 (d, J=6.3 Hz, 2H), 4.33 (d, J=12.0 Hz, 1H), 3.37 (m, 1H), 3.19-3.08 (m, 1H), 1.08 (d, J=6.8 Hz, 3H).

The synthesis of (E)-1-(3-(4-chlorobut-2-enamido)-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-36)

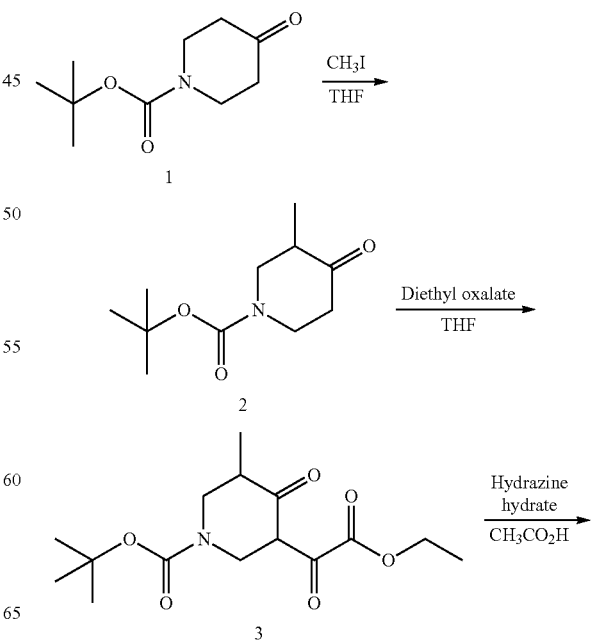

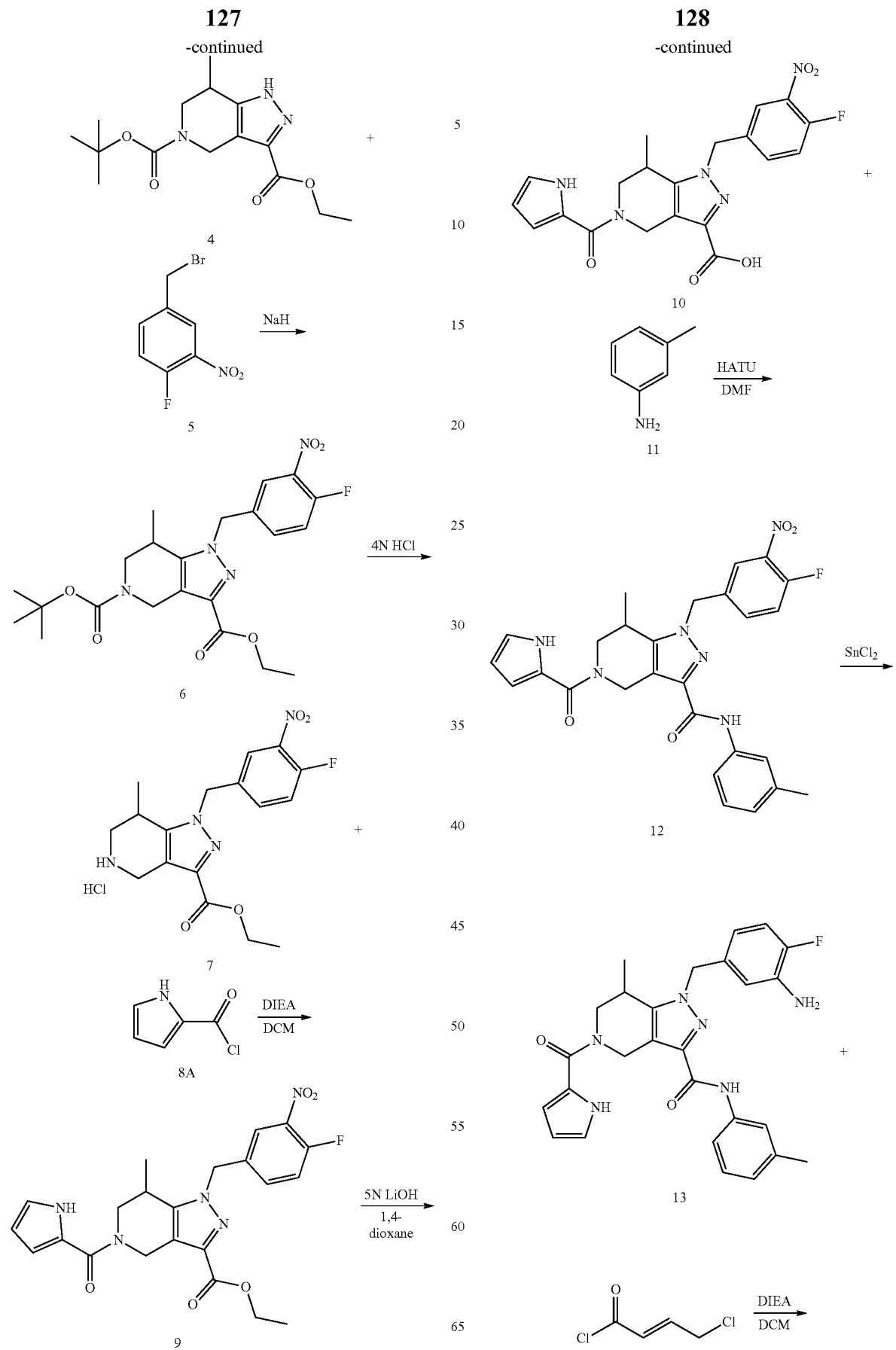

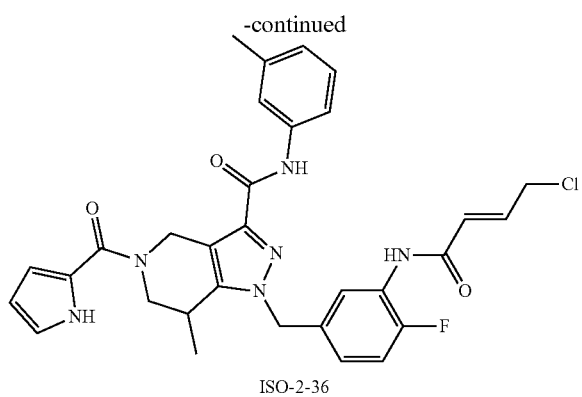

ISO-2-36

5-((1H-pyrrol-2-yl)methyl)-1-(4-fluoro-3-nitrobenzyl)-7-methyl-N-(m-tolyl)-4,5,6,7-tetrahydro-1H-pyrazolo[4,3-c]pyridine-3-carboxamide(12) To a solution of 1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylic acid (10) (0.32 g, 0.75 mmol) in DMF (5 mL) were added m-toluidine (0.1 g, 0.9 mmol), HATU (0.43 g, 1.125 mmol) and DIEA (0.2 g, 1.5 mmol). The mixture was stirred at room temperature under nitrogen. After 1 h, the reaction mixture was added water and the resulting precipitate was collected by filtration and dried on a lyophilizer overnight to afford compound (12) (0.36 g, 95%) as a white solid. MS m/z 517[M+H]$^+$.

1-(3-amino-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide(13) To a solution of 5-((1H-pyrrol-2-yl)methyl)-1-(4-fluoro-3-nitrobenzyl)-7-methyl-N-(m-tolyl)-4,5,6,7-tetrahydro-1H-pyrazolo[4,3-c]pyridine-3-carboxamide (12) (0.36 g, 0.7 mmol) in ethyl acetate/methanol (4/1) 10 mL) was added stannous chloride (1.12 g, 5.6 mmol). The resulting mixture was heated at 80° C. overnight. The reaction mixture was added DCM and the pH was adjusted to 8 with saturated aqueous NaHCO$_3$ and extracted with DCM. The organic layer was washed with brine, dried, concentrated under reduced pressure and the residue was purified by silica gel chromatography to afford the compound as a white solid (0.3 g, 88%). MS m/z 487 [M+H]$^+$.

1-(3-amino-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide(ISO-2-36) To a solution of 1-(3-acrylamido-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (13) (0.12 g, 0.247 mmol) in DCM (2 mL) was added DIEA (64 mg, 0.494 mmol) and (E)-4-chlorobut-2-enoyl chloride (41 mg, 0.296 mmol) at −20° C. for 5 min. The reaction mixture was diluted with water and saturated aqueous NaHCO$_3$ and extracted with DCM. The organic layer was washed with brine, dried, concentrated under reduced pressure and the residue was purified by silica gel chromatography to afford the compound as a white solid. MS m/z 590[M+H]$^+$. $^1$H NMR (400 MHz, DMSO) δ 11.52 (s, 1H), 9.89 (s, 1H), 9.83 (s, 1H), 7.83 (d, J=6.8 Hz, 1H), 7.68 (s, 1H), 7.56 (d, J=8.2 Hz, 1H), 7.27-7.15 (m, 2H), 6.96 (m, 1H), 6.91 (m, 2H), 6.59 (m, 1H), 6.42 (d, J=7.0 Hz, 1H), 6.17 (m, 1H), 6.12 (m, 1H), 5.41 (q, J=16.4 Hz, 2H), 5.30 (d, J=16.4 Hz, 1H), 4.67 (br, 1H), 4.36 (d, J=12.0 Hz, 1H), 3.39 (d, J=5.0 Hz, 3H), 3.18 (m, 1H), 2.29 (s, 3H), 1.11 (d, J=6.8 Hz, 3H).

The synthesis of 1-(((6-acrylamidonaphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-38)

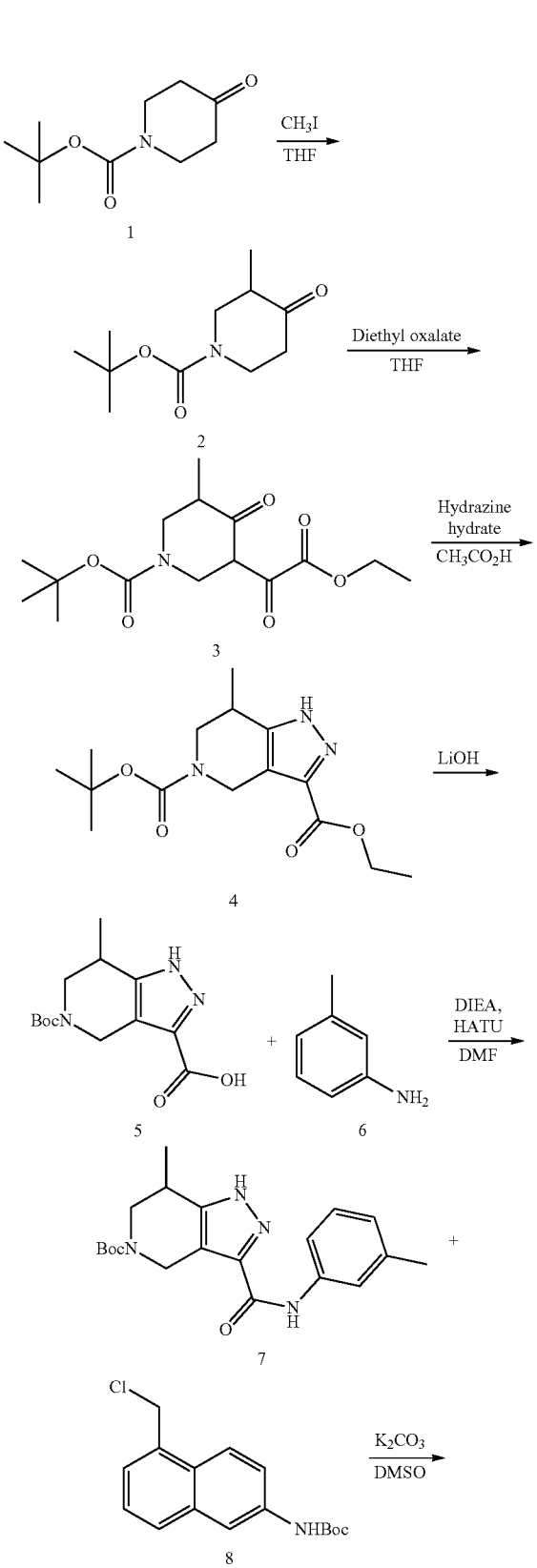

-continued

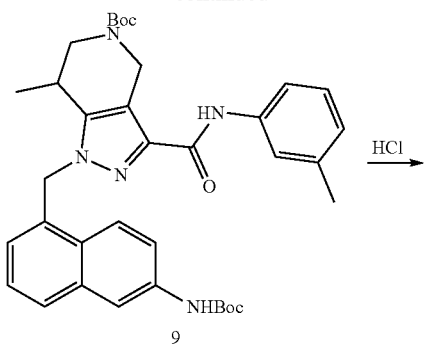
9

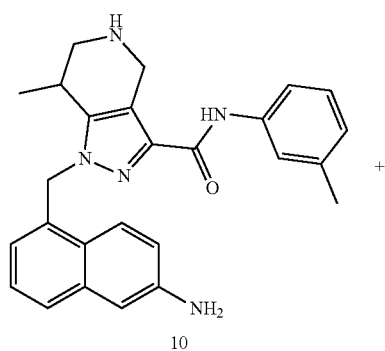
10

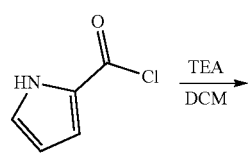

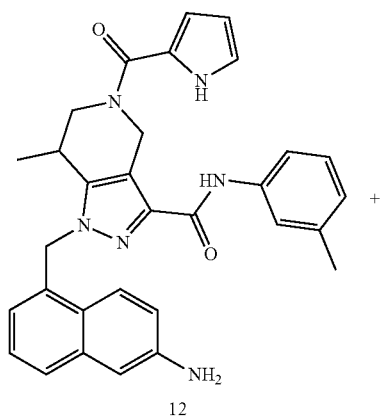
12

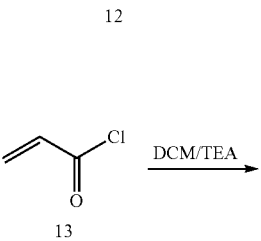
13

-continued

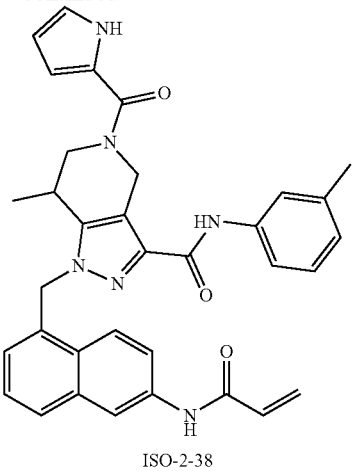 [SMILES: C=CC(=O)Nc1ccc2c(Cn3nc(C(=O)Nc4cccc(C)c4)c4c3C(C)CN(C(=O)c3ccc[nH]3)C4)cccc2c1]
ISO-2-38

5-(tert-butoxycarbonyl)-7-methyl-4,5,6,7-tetrahydro-1H-pyrazolo[4,3-c]pyridine-3-carboxylic acid (5) To a solution of 5-(tert-butyl) 3-ethyl 7-methyl-1,4,6,7-tetrahydro-5H-pyrazolo[4,3-c]pyridine-3,5-dicarboxylate (4) (5 g, 16.1 mmol) in MeOH (30 mL) was added with 5N LiOH (20 mL). The clear solution was stirred at room temperature. The reaction mixture was added with water and pH was adjusted to 6 with 6N HCl. The resulting precipitate was collected by filtration and dried to afford 5-(tert-butoxycarbonyl)-7-methyl-4,5,6,7-tetrahydro-1H-pyrazolo[4,3-c]pyridine-3-carboxylic acid (4.5 g, 99%) as a white solid. MS m/z 282 [M+H]$^+$.

Tert-butyl 7-methyl-3-(m-tolylcarbamoyl)-1,4,6,7-tetrahydro-5H-pyrazolo[4,3-c]pyridine-5-carboxylate (7) To a solution of 5-(tert-butoxycarbonyl)-7-methyl-4,5,6,7-tetrahydro-1H-pyrazolo[4,3-c]pyridine-3-carboxylic acid (5) (2.4 g, 8.5 mmol) in DMF (10 mL) were added m-toluidine (1.2 g, 10.2 mmol), HATU (4.8 g, 12.75 mmol) and DIEA (2.5 g, 17 mmol). The mixture was stirred at room temperature. The reaction mixture was added with water and the resulting precipitate was collected by filtration and dried to afford compound (7) (2.3 g, 74%) as a white solid. MS m/z 371[M+H]$^+$.

5-(tert-butyl) 3-ethyl 1-(4-fluorobenzyl)-7-methyl-1,4,6,7-tetrahydro-5H-pyrazolo[4,3-c]pyridine-3,5-dicarboxylate (9) To a solution of tert-butyl 7-methyl-3-(m-tolylcarbamoyl)-1,4,6,7-tetrahydro-5H-pyrazolo[4,3-c]pyridine-5-carboxylate (7) (1 g, 2.7 mmol) in dry DMSO (30 mL) was added K$_2$CO$_3$ (0.6 g, 4 mmol) and tert-butyl (5-(chloromethyl)naphthalen-2-yl)carbamate (1.5 g, 4 mmol). The mixture was stirred at 80° C. After 1 h the reaction mixture was quenched with water and extracted with ethyl acetate. The combined extracts were dried, filtered and concentrated under reduced pressure. The residue was purified by silica gel chromatography. The appropriate fractions were combined concentrated under reduced pressure and the residue was dried to afford tert-butyl 1-((6-((tert-butoxycarbonyl)amino)naphthalen-1-yl)methyl)-7-methyl-3-(m-tolylcarbamoyl)-1,4,6,7-tetrahydro-5H-pyrazolo[4,3-c]pyridine-5-carboxylate (1.05 g, 60%) as a light yellow solid. MS m/z 626 [M+H]$^+$.

1-((6-aminonaphthalen-1-yl)methyl)-7-methyl-N-(m-tolyl)-4,5,6,7-tetrahydro-1H-pyrazolo[4,3-c]pyridine-3-carboxamide (10) To a round-bottom flask containing tert-butyl 1-((6-((tert-butoxycarbonyl)amino)naphthalen-1-yl)methyl)-7-methyl-3-(m-tolylcarbamoyl)-1,4,6,7-tetrahydro- 5H-pyrazolo[4,3-c]pyridine-5-carboxylate (9) (1 g, 1.6 mmol) was added with HCl (4 N in ethyl acetate, 20 mL). The resulting solution was stirred at room temperature. The reaction mixture was concentrated under reduced pressure and the resulting residue was dried to afford 1-((6-aminonaphthalen-1-yl)methyl)-7-methyl-N-(m-tolyl)-4,5,6,7-tetrahydro-1H-pyrazolo[4,3-c]pyridine-3-carboxamide (0.75 g, 100%) as a yellow solid.

Ethyl 1-(4-fluoro-3-nitrobenzyl)-7-methyl-5-(1H-pyrrole-2-carbonyl)-4,5,6,7-tetrahydro-1H-pyrazolo[4,3-c]pyridine-3-carboxylate(12) To a solution of 1-((6-aminonaphthalen-1-yl)methyl)-7-methyl-N-(m-tolyl)-4,5,6,7-tetrahydro-1H-pyrazolo[4,3-c]pyridine-3-carboxamide (10) (0.75 g, 1.76 mmol) in dichloromethane (10 mL) was added TEA (0.27 g, 2.64 mmol) and 1H-pyrrole-2-carbonyl chloride (0.227 g, 1.76 mmol) at −20° C. for 50 min. The reaction mixture was diluted with water and extracted with dichloromethane. The organic layer was dried, concentrated under reduced pressure and the residue was purified by silica gel chromatography to afford the compound as a yellow solid (0.4 g, 44%). MS m/z 519[M+H]$^+$.

1-((6-acrylamidonaphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-38) To a solution of 1-((6-aminonaphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (12) (110 mg, 0.21 mmol) in dichloromethane (5 mL) was added TEA (48 mg, 0.42 mmol) and acryloyl chloride (35 mg, 0.33 mmol) at 0° C. The reaction mixture was diluted with water and saturated aqueous NaHCO$_3$. Dichloromethane was added and the organic layer was washed with brine and dried. Then concentrated under reduced pressure and the residue was purified by silica gel chromatography to afford the compound as a white solid (25 mg, 20%). MS m/z 573 [M+H]$^+$.
$^1$H NMR (400 MHz, DMSO) δ 11.55 (s, 1H), 10.82 (s, 1H), 9.91 (s, 1H), 8.48 (s, 1H), 8.23 (d, J=9.0 Hz, 1H), 7.92 (d, J=8.4 Hz, 1H), 7.79 (d, J=8.2 Hz, 1H), 7.69 (s, 1H), 7.56 (d, J=8.2 Hz, 1H), 7.40 (t, J=8.2 Hz, 1H), 7.20 (t, J=7.8 Hz, 1H), 6.95-6.84 (m, 2H), 6.70-6.56 (m, 3H), 6.31 (dd, J=17.0, 1.6 Hz, 1H), 6.17 (s, 1H), 6.05 (d, J=16.4 Hz, 1H), 5.95 (d, J=16.4 Hz, 1H), 5.80 (d, J=10.0 Hz, 1H), 5.35 (d, J=16.7 Hz, 1H), 4.75 (br, 1H), 4.34 (d, J=11.6 Hz, 1H), 3.38 (m, 1H), 3.15 (m, 1H), 2.29 (s, 3H), 1.03 (d, J=6.8 Hz, 3H).

The synthesis of (R)-1-((6-acrylamidonaphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-38-R)

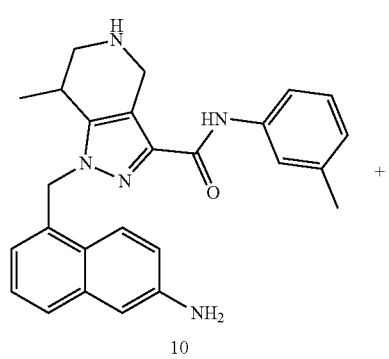

10

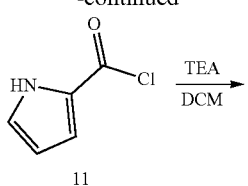

11

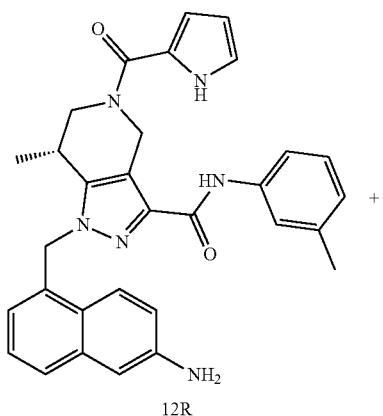

12R

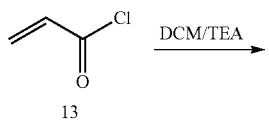

13

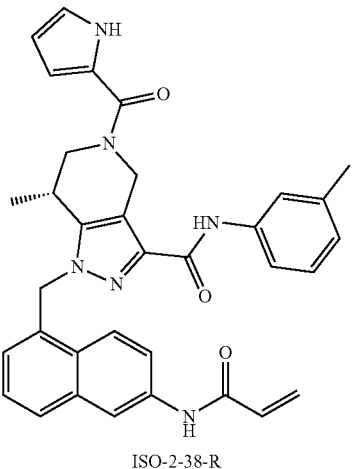

ISO-2-38-R

The 12R was purified by chiral column and then the final compound ISO-2-38-R was made with same procedure as ISO-2-38.

The synthesis of (S)-1-((6-acrylamidonaphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-38-S)

The 12S was purified by chiral column and then the final compound ISO-2-38-S was made with same procedure as ISO-2-38.

The synthesis of (E)-1-((6-(4-(dimethylamino)but-2-enamido)naphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-39)

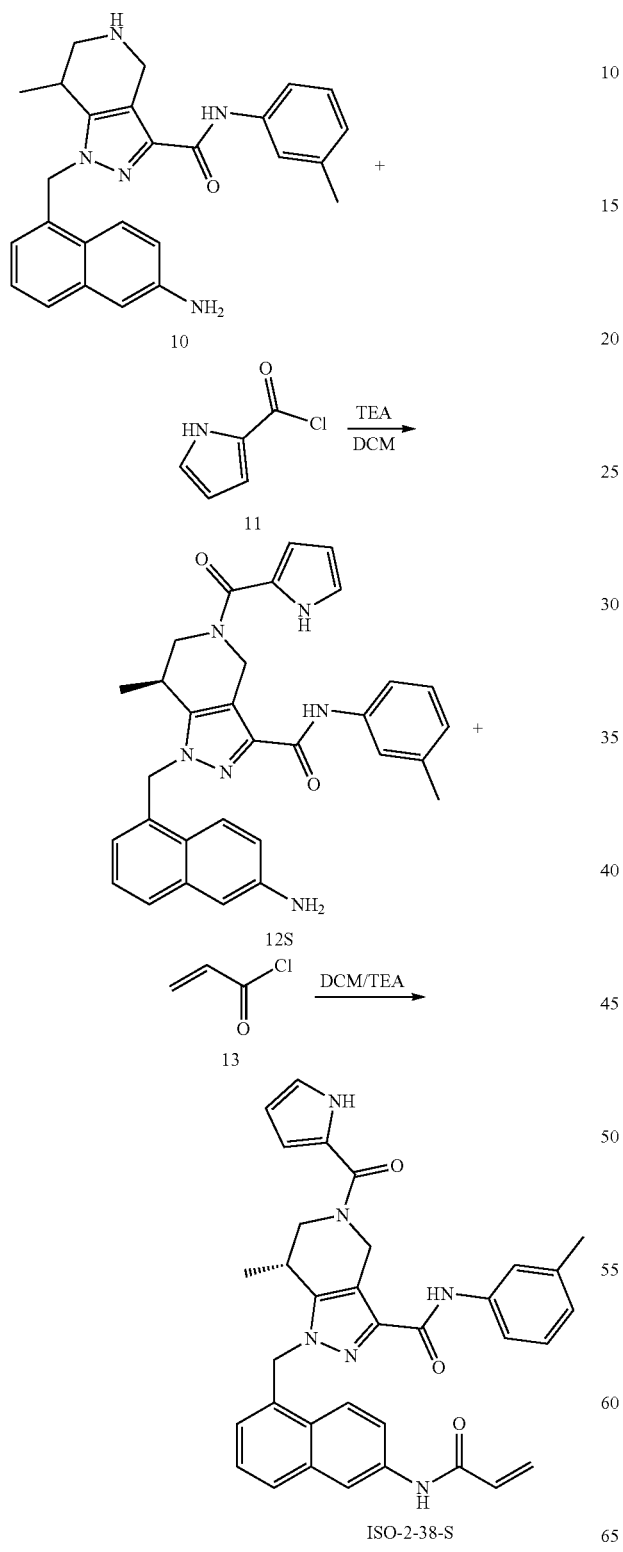

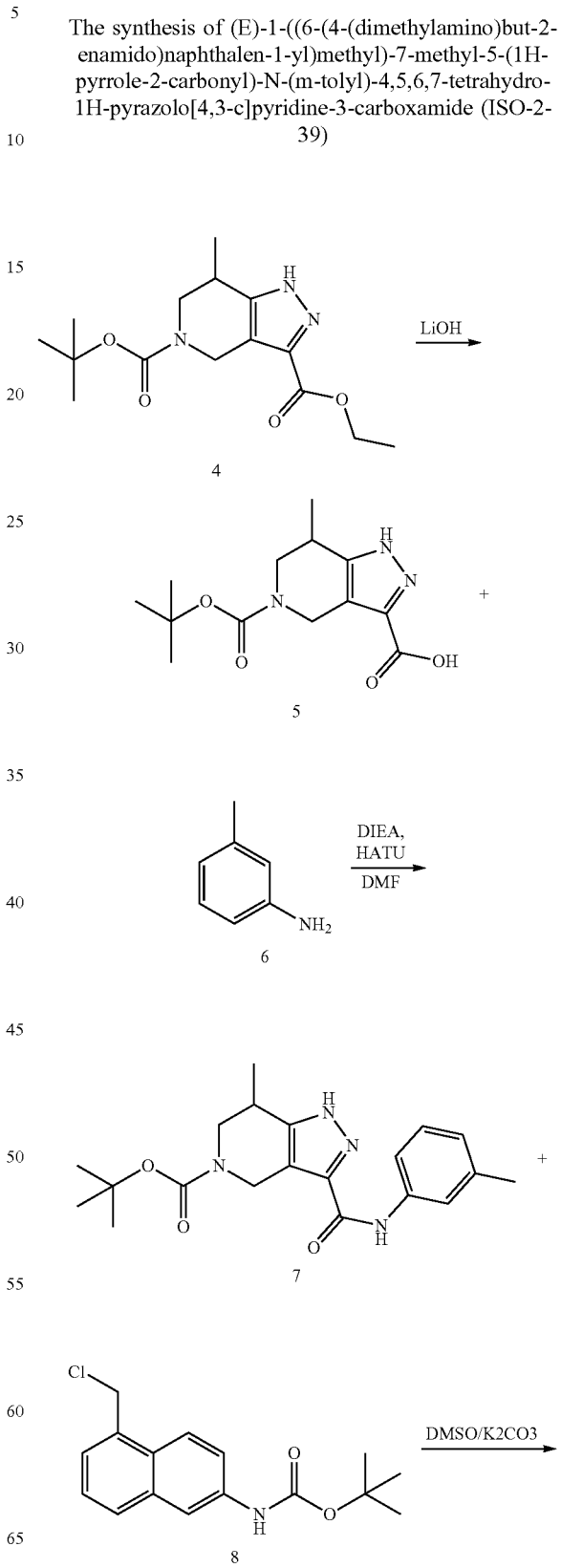

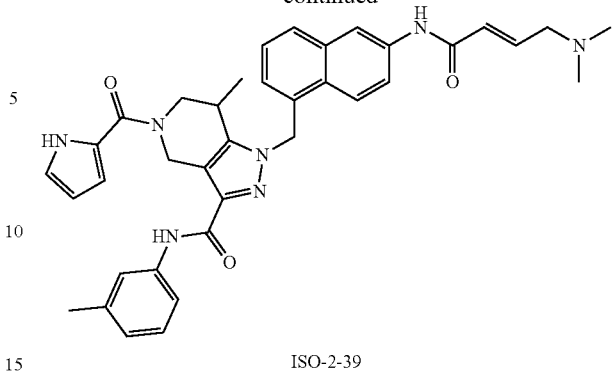

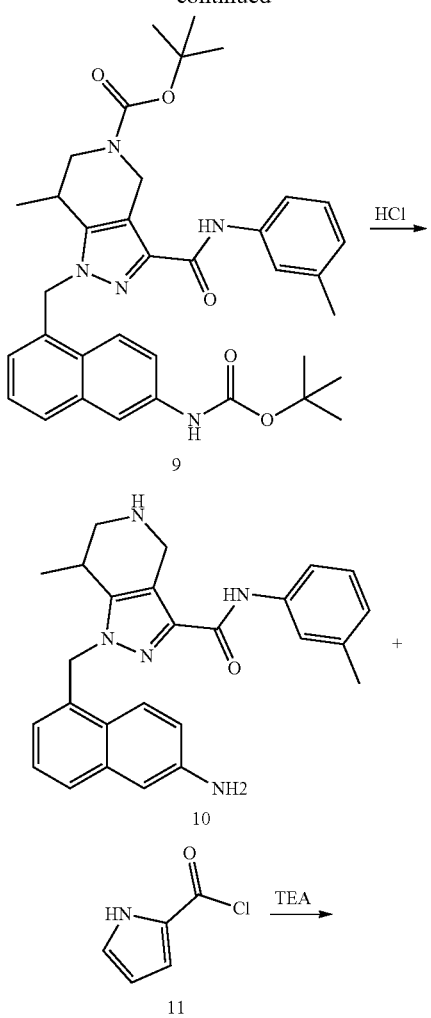

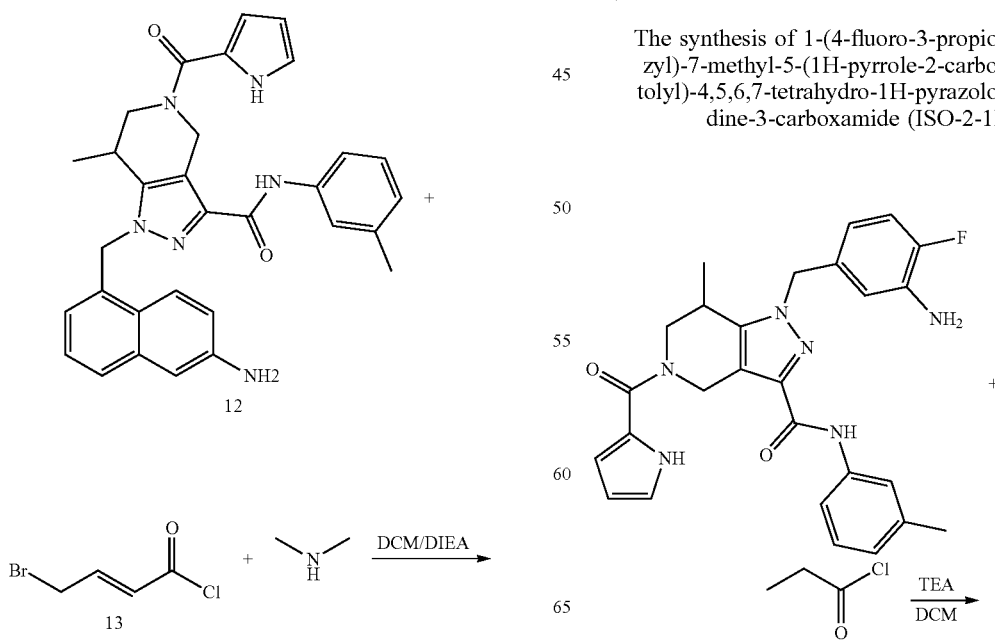

(E)-1-(((6-(4-(dimethylamino)but-2-enamido)naphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-39) To a solution of 1-((6-aminonaphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (12) (200 mg, 0.38 mmol) in dichloromethane (5 mL) was added DIEA (100 mg, 0.78 mmol) and (E)-4-bromobut-2-enoyl chloride (106 mg, 0.78 mmol) at 0° C. 10 min later dimethylamine (2 N in THF, 10 mL) was added. The reaction mixture was diluted with water and saturated aqueous NaHCO$_3$, dichloromethane was added and the organic layer was washed with brine and dried. Then concentrated under reduced pressure and the residue was purified by silica gel chromatography to afford the compound as a white solid (25 mg, 10%). MS m/z 630 [M+H]+. $^1$H NMR (400 MHz, DMSO-d6) δ 11.54 (s, 1H), 10.53 (s, 1H), 9.90 (s, 1H), 8.43 (s, 1H), 8.23 (d, J=9.1 Hz, 1H), 7.84 (m, 2H), 7.68 (s, 1H), 7.56 (d, J=8.2 Hz, 1H), 7.40 (t, J=8.2 Hz, 1H), 7.20 (t, J=7.8 Hz, 1H), 6.99-6.87 (m, 2H), 6.87-6.77 (m, 1H), 6.67 (d, J=7.1 Hz, 1H), 6.59 (m, 1H), 6.45 (d, J=15.6 Hz, 1H), 6.19 (s, 1H), 6.05 (d, J=16.4 Hz, 1H), 5.87 (d, J=16.0 Hz, 1H), 5.34 (d, J=16.8 Hz, 1H), 4.71 (br, 1H), 4.33 (d, J=13.6 Hz, 1H), 3.49 (s, 2H), 3.33 (m 1H), 3.14 (m, 1H), 2.47 (s, 6H), 2.29 (s, 3H), 1.02 (d, J=6.8 Hz, 3H).

The synthesis of 1-(4-fluoro-3-propionamidobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-1Rev)

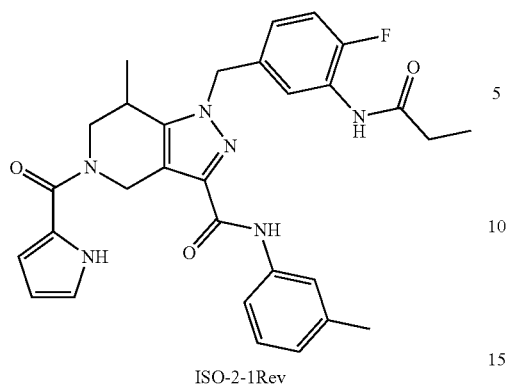

ISO-2-1Rev

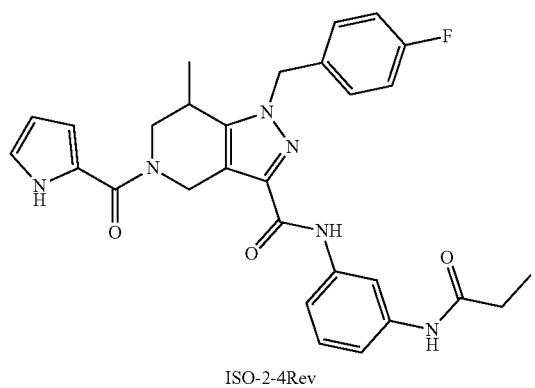

ISO-2-4Rev 1-(4-fluoro-3-propionamidobenzyl)-7-methyl-5-(1H-pyrrole-2-carbonyl)-N-(m-tolyl)-4,5,6,7-tetrahydro-1H-pyrazolo[4,3-c]pyridine-3-carboxamide (ISO-2-1Rev) To a solution of 1-(3-acrylamido-4-fluorobenzyl)-7-methyl-5-(1H-pyrrole-2-carbonyl)-N-(m-tolyl)-4,5,6,7-tetrahydro-1H-pyrazolo[4,3-c]pyridine-3-carboxamide (0.2 g, 0.41 mmol) in DCM (10 mL) was added TEA (0.15 g, 1.40 mmol) and propionyl chloride (0.13 g, 1.4 mmol) at 0° C. The reaction mixture was diluted with water and saturated aqueous NaHCO$_3$ and extracted with DCM. The organic layer was washed with brine, dried over Na$_2$SO$_4$, concentrated under reduced pressure and the residue was purified by silica gel chromatography to afford the compound as a white solid (66 mg, 26%). MS m/z543[M+H]+. $^1$H NMR (400 MHz, DMSO-d6) δ 11.54 (s, 1H), 9.85 (s, 1H), 9.78 (s, 1H), 7.84 (d, J=6.4 Hz, 1H), 7.68 (s, 1H), 7.58 (d, J=8.0 Hz, 1H), 7.28-7.11 (m, 2H), 6.98-6.81 (m, 3H), 6.58 (s, 1H), 6.16 (s, 1H), 5.48-5.23 (m, 3H), 4.64 (br, 1H), 4.35 (d, J=12.4 Hz, 1H), 3.41 (m, 1H), 3.28 (m, 1H), 2.38 (q, J=7.6 Hz, 2H), 2.28 (s, 3H), 1.10 (d, J=6.8 Hz, 3H), 1.05 (t, J=7.5 Hz, 3H).

1-(4-fluorobenzyl)-7-methyl-N-(3-propionamidophenyl)-5-(1H-pyrrole-2-carbonyl)-4,5,6,7-tetrahydro-1H-pyrazolo[4,3-c]pyridine-3-carboxamide (ISO-2-4Rev) To a solution of N-(3-aminophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) (180 mg, 0.37 mmol) in DCM (20 mL) was added TEA (75 mg, 0.6 mmol) and propionyl chloride (50 mg, 0.4 mmol) at 0° C. The reaction mixture was diluted with water and saturated aqueous NaHCO$_3$ and extracted with DCM. The organic layer was washed with brine, dried over Na$_2$SO$_4$, concentrated under reduced pressure and the residue was purified by silica gel chromatography to afford the compound as a white solid (42 mg, 35%). MS m/z529[M+H]+. 1H NMR (400 MHz, DMSO-d6) δ 11.6 (s, 1H), 9.93 (s, 1H), 9.90 (s, 1H), 8.15 (s, 1H), 7.43 (d, J=8.0, Hz, 1H), 7.37-7.24 (m, 3H), 7.19 (m, 3H), 6.91 (s, 1H), 6.58 (m, 1H), 6.18 (m, 1H), 5.45 (q, J=16.4 Hz, 2H), 5.31 (d, J=16.4 Hz, 1H), 4.67 (br, 1H), 4.35 (m, 1H), 3.38 (d, J=13.2 Hz, 1H), 3.21-3.10 (m, 1H), 2.32 (m, 2H), 1.12-1.00 (m, 6H).

The synthesis of 1-(4-fluorobenzyl)-7-methyl-N-(3-propionamidophenyl)-5-(1H-pyrrole-2-carbonyl)-4,5,6,7-tetrahydro-1H-pyrazolo[4,3-c]pyridine-3-carboxamide (ISO-2-4Rev)

The synthesis of 1-(4-fluorobenzyl)-7-methyl-N-(4-propionamidophenyl)-5-(1H-pyrrole-2-carbonyl)-4,5,6,7-tetrahydro-1H-pyrazolo[4,3-c]pyridine-3-carboxamide (ISO-2-25Rev)

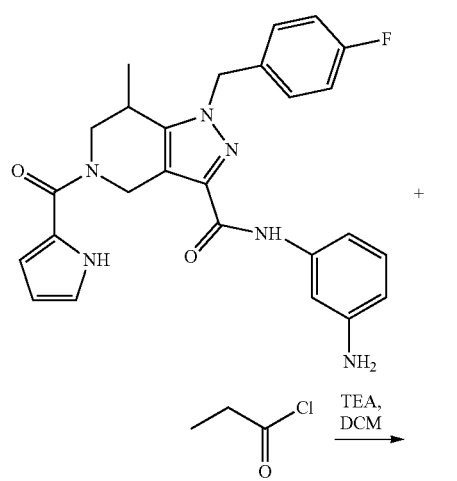

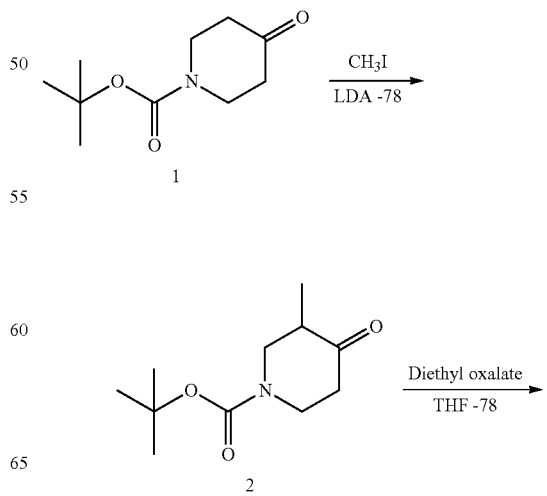

-continued
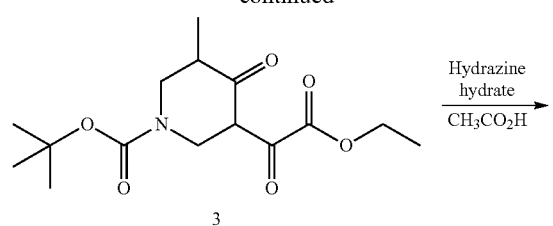
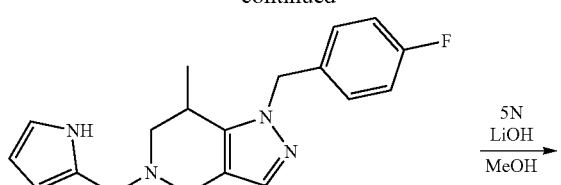
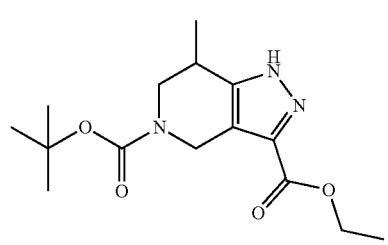
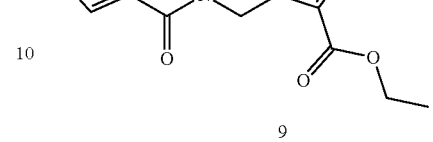
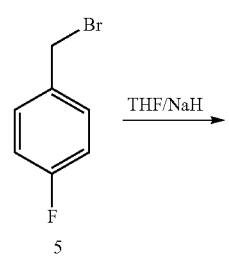
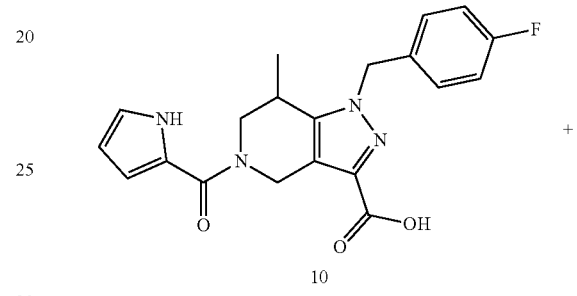
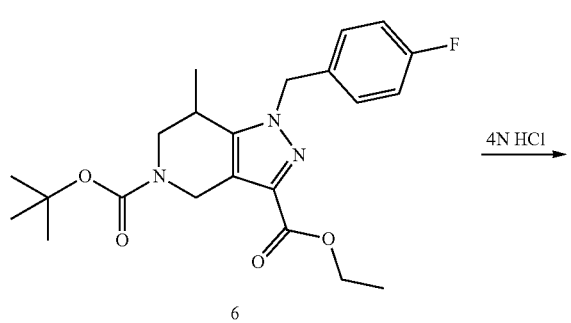
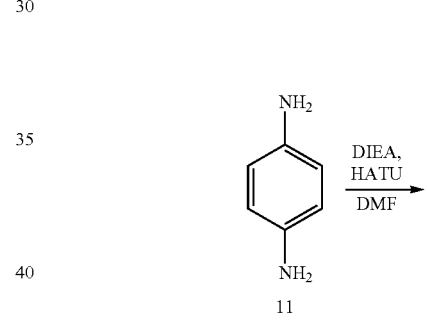
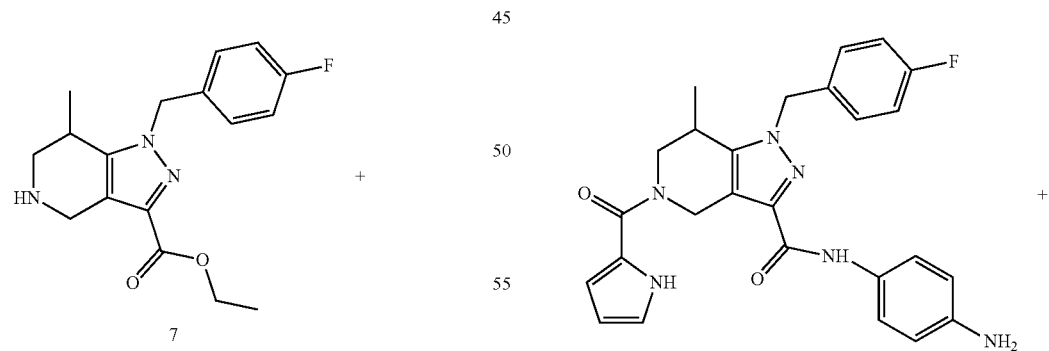
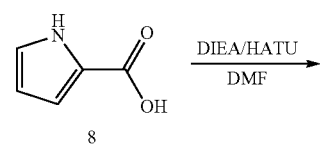
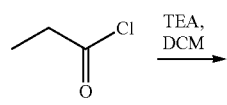

143

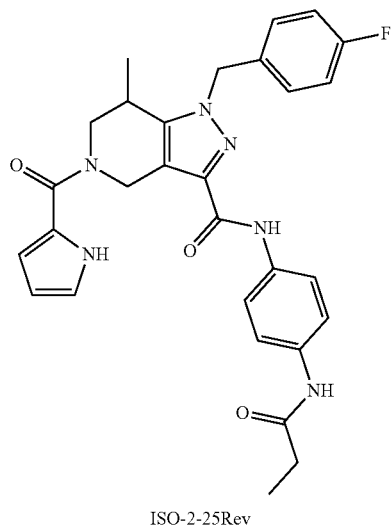

ISO-2-25Rev 1-(4-fluorobenzyl)-7-methyl-N-(4-propionamidophenyl)-5-(1H-pyrrole-2-carbonyl)-4,5,6,7-tetrahydro-1H-pyrazolo[4,3-c]pyridine-3-carboxamide (ISO-2-25Rev) To a solution of N-(3-aminophenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (12) (90 mg, 0.18 mmol) in DCM (5 mL) was added TEA (44 mg, 0.4 mmol) and propionyl chloride (30 mg, 0.3 mmol) at 0° C. The reaction mixture was diluted with water and saturated aqueous NaHCO₃ and extracted with DCM. The organic layer was washed with brine and dried. Then concentrated under reduced pressure and the residue was purified by silica gel chromatography to afford the compound as a white solid (36 mg, 25%). MS m/z 529[M+H]$^+$. $^1$H NMR (400 MHz, DMSO) δ 11.53 (s, 1H), 9.94 (s, 1H), 9.86 (s, 1H), 7.70 (d, J=9.0 Hz, 2H), 7.53 (d, J=8.9 Hz, 2H), 7.26 (m, 2H), 7.19 (m, 2H), 6.91 (s, 1H), 6.58 (s, 1H), 6.16 (m, 1H), 5.44 (q, J=16.4 Hz, 2H), 5.30 (d, J=16.4 Hz, 1H), 4.65 (br, 1H), 4.35 (d, J=12.0 Hz, 1H), 3.38 (m, 1H), 3.17 (m, J=5.0 Hz, 1H), 2.36-2.24 (m, 2H), 1.12-1.04 (m, 6H).

The synthesis of 1-(4-fluorobenzyl)-N-(4-methoxy-3-propionamidophenyl)-7-methyl-5-(1H-pyrrole-2-carbonyl)-4,5,6,7-tetrahydro-1H-pyrazolo[4,3-c]pyridine-3-carboxamide (ISO-2-30Rev)

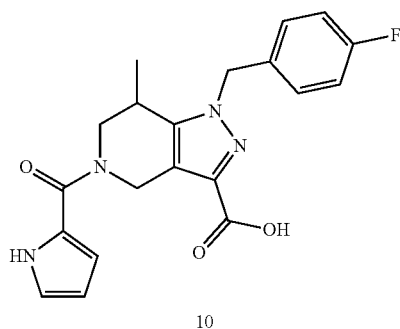

10

144

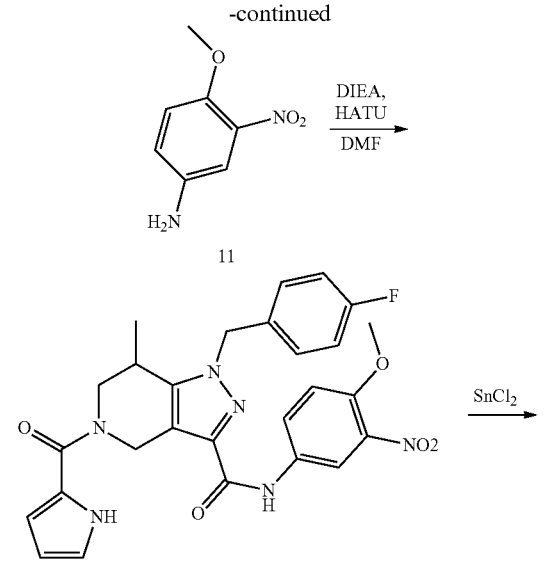

1-(4-fluorobenzyl)-N-(4-methoxy-3-propionamidophenyl)-7-methyl-5-(1H-pyrrole-2-carbonyl)-4,5,6,7-tetrahydro-1H-pyrazolo[4,3-c]pyridine-3-carboxamide (ISO-2-30Rev) To a solution of N-(3-amino-4-methoxyphenyl)-1-(4-fluorobenzyl)-7-methyl-5-(1H-pyrrole-2-carbonyl)-4,5,6,7-tetrahydro-1H-pyrazolo[4,3-c]pyridine-3-carboxamide (13) (110 mg, 0.21 mmol) in dichloromethane (5 mL) was added TEA (48 mg, 0.42 mmol) and propionyl chloride (35 mg, 0.33 mmol) at 0° C. The reaction mixture was diluted with water and saturated aqueous NaHCO₃. Dichloromethanane was added and the organic layer was washed with brine and dried. Then concentrated under reduced pressure and the residue was purified by silica gel chromatography to afford the compound as a white solid (42 mg, 36%). MS m/z559 [M+H]+. 1H NMR (400 MHz, DMSO) δ 11.53 (s, 1H), 9.82 (s, 1H), 9.01 (s, 1H), 8.34 (s, 1H), 7.47 (m, 1H), 7.33-7.23 (m, 2H), 7.23-7.14 (m, 2H), 6.97 (d, J=9.0 Hz, 1H), 6.91 (m, 1H), 6.58 (m, 1H), 6.17 (m, 1H), 5.43 (q, J=16.4 Hz, 2H), 5.29 (d, J=16.4 Hz, 1H), 4.66 (s, 1H), 4.34 (m, 1H), 3.81 (s, 3H), 3.37 (m, 1H), 3.16 (m, 1H), 2.39 (m, 2H), 1.07 (m, 6H).

The synthesis of 7-methyl-1-((6-propionamidonaphthalen-1-yl)methyl)-5-(1H-pyrrole-2-carbonyl)-N-(m-tolyl)-4,5,6,7-tetrahydro-1H-pyrazolo[4,3-c]pyridine-3-carboxamide (ISO-2-38Rev)

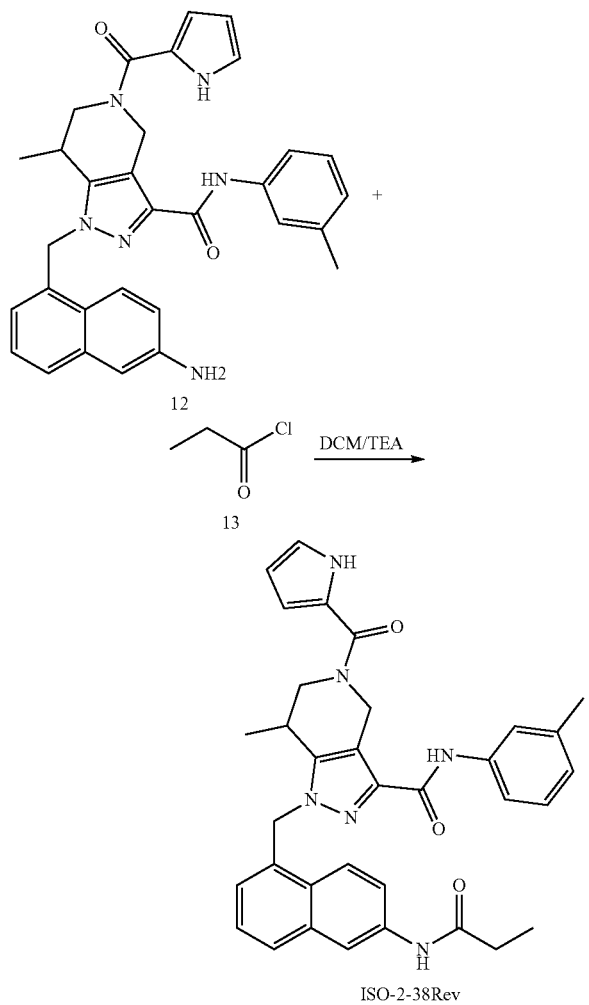

7-methyl-1-((6-propionamidonaphthalen-1-yl)methyl)-5-(1H-pyrrole-2-carbonyl)-N-(m-tolyl)-4,5,6,7-tetrahydro-1H-pyrazolo[4,3-c]pyridine-3-carboxamide (ISO-2-38Rev) To a solution of 1-((6-aminonaphthalen-1-yl)methyl)-7-methyl-5-(1H-pyrrole-2-carbonyl)-N-(m-tolyl)-4,5,6,7-tetrahydro-1H-pyrazolo[4,3-c]pyridine-3-carboxamide (12) (110 mg, 0.21 mmol) in dichloromethane (5 mL) was added TEA (48 mg, 0.42 mmol) and propionyl chloride (35 mg, 0.33 mmol) at 0° C. The reaction mixture was diluted with water and saturated aqueous NaHCO3. Dichloromethane was added and the organic layer was washed with brine and dried. Then concentrated under reduced pressure and the residue was purified by silica gel chromatography to afford the compound as a yellow solid (25 mg, 20%). MS m/z575 [M+H]+. 1H NMR (400 MHz, DMSO) δ 11.53 (s, 1H), 10.20 (s, 1H), 9.88 (s, 1H), 8.35 (s, 1H), 8.19 (d, J=9.1 Hz, 1H), 7.75 (m, 2H), 7.68 (s, 1H), 7.56 (d, J=7.4 Hz, 1H), 7.38 (t, J=8.0 Hz, 1H), 7.18 (t, J=7.8 Hz, 1H), 6.91 (m, 2H), 6.64 (d, J=7.2 Hz, 1H), 6.59 (s, 1H), 6.17 (m, 1H), 6.05 (d, J=16.4 Hz, 1H), 5.85 (d, J=16.4 Hz, 1H), 5.34 (d, J=16.4 Hz, m, 1H), 4.71 (br, 1H), 4.33 (d, J=12.0 Hz, 1H), 3.38 (m, 1H), 3.13 (m, 1H), 2.40 (q, J=7.2 Hz, 2H), 2.29 (s, 3H), 1.13 (t, J=7.6 Hz, 3H), 1.02 (d, J=6.8 Hz, 3H).

Separation of Enantiomers

| | |
|---|---|
| Column | CHIRALPAK IE(IE00CD-TB005) |
| Column size | 0.46 cm I.D. × 15 cm L |
| Injection | 10.0 μL or 20 μL |
| Mobile phase | DCM/MeOH = 95/5(V/V) |
| Flow rate | 1.0 mL/min |
| Wave length | UV 254 nm |
| Temperature | 35° C. |
| HPLC equipment | Shimadzu LC-20AD CP-HPLC-07 |
| HPLC equipment | Shimadzu LC-20AD CP-HPLC-06 |

MALDI TOF Method for IsoCure Intact Mw Analysis

Experimental: Analyses were performed on a Shimadzu Biotech Axima TOF2 (Shimadzu Instruments) matrix-assisted-laser desorption/ionization time-of-flight (MALDI-TOF) mass spectrometer. Proteins were analyzed in positive ion linear mode. For intact protein mass measurement the instrument was set with a mass range extending up to 75000 m/z using a pulsed extraction setting of 47000 and apomyoglobin as the standard to calibrate the instrument. A 3 μl aliquot of each sample was diluted with 7 μL of 0.1% TFA prior to micro C4 Zip Tip desalting and deposition directly onto the MALDI target using Sinapinic acid as the desorption matrix (10 mg/mL in 0.1% TFA:Acetonitrile 50:50).

In Solution Digestion

A 5 μL aliquot of each sample was added to 20 μL of 0.1% ProteaseMAX Surfactant (Promega) in 50 mM Ammonium Bicarbonate to initially dissolve and denature the proteins. An additional aliquot of 20 μL of 50 mM Ammonium Bicarbonate was then added. For reduction a 2 μL aliquot of 45 mM DTT was added and the samples were incubated at 50° C. for 30 min. For alkylation of cysteine a 2 μL aliquot of 100 mM iodoacetamide was added and the samples were incubated at room temperature for 30 min. Tryptic digestion was initiated with a 1 μL aliquot of Trypsin (0.2 μg/μL Sigma Proteomics grade). Samples were incubated at 37° C. for 18 h. Tryptic digests were acidified with 4 μL of 5% trifluoroacetic acid (TFA).

LC/MS/MS on Q Exactive

A 2.5 μL aliquot was directly injected onto a custom packed 2 cm×100 μm C18 Magic 5μ particle trap column. Peptides were then eluted and sprayed from a custom packed emitter (75 μm×25 cm C18 Magic 3 μm particle) with a linear gradient from 95% solvent A (0.1% formic acid in water) to 35% solvent B (0.1% formic acid in Acetonitrile) in 35 min at a flow rate of 300 nanoliters per minute on a Waters Nano Acquity UPLC system. Data dependent acquisitions were performed on a Q Exactive mass spectrometer (Thermo Scientific) according to an experiment where full MS scans from 300-1750 m/z were acquired at a resolution of 70,000 followed by 10 MS/MS scans acquired under HCD fragmentation at a resolution of 17,500 with an isolation width of 1.6 Da. Raw data files were processed with Proteome Discoverer (version 2.1) prior to searching with Mascot Server (version 2.5) against the SwissProt Human database. Search parameters utilized were tryptic with 2 missed cleavages, parent mass tolerances of 10 ppm and fragment mass tolerances of 0.05 Da. A fixed modification of carbamidomethyl cysteine and variable modifications of acetyl (protein N-term), pyro glutamic for N-term glutamine, oxidation of methionine, and 3 different Isocure compounds were considered. Search results were loaded into the Scaffold Viewer (Proteome Software, Inc.) for assessment of protein identification probabilities and label free quantitation.

Testing for Biological Activities

Compounds were tested against 3 enzymes, as provided below.

Compounds were tested in 10-dose IC50 mode with 3-fold serial dilution at a starting concentration of 10 µM.

Control Compounds were tested in 10-dose IC50 mode with 3-fold serial dilution starting at 1 mM or 10 mM.

Assay Format: The production or depletion of NADPH by IDH enzymes was measured by diaphorase/resazurin coupled detection.

Fluorescence measurement: Ex/Em=535/590 by EnVision.

Compounds were pre-incubated with enzyme for 1 h at room temperature.

Standard substrate: 1500 µM a-Ketoglutarate+15 µM NADPH for IDH1 (R132H). 500 µM a-Ketoglutarate+15 µM NADPH for IDH1 (R132C). 65 µM Isocitrate+50 µM NADP for IDH1.

Exemplary results are presented in Table 1 and FIGS. 2-7.

TABLE 1

Summary of Exemplary IC50 Results

| Compound ID: | Compound IC50 (nM) | | |
|---|---|---|---|
| | IDH1 (R132H) | IDH1 (R132C) | IDH1 |
| ISO-2-1 | 18 | 35 | >10000 |
| ISO-2-2 | 33 | 152 | >10000 |
| ISO-2-3 | 34 | 77 | 10000 |
| ISO-2-4 | 49 | 121 | >10000 |
| ISO-2-5 | 3 | 2 | >10000 |
| ISO-2-6 | >10000 | >10000 | >10000 |
| ISO-2-7 | 153 | 247 | >10000 |
| ISO-2-8 | 52 | 154 | >10000 |
| ISO-2-9 | >10000 | >10000 | >10000 |
| ISO-2-10 | >10000 | 9500 | >10000 |
| ISO-2-19 | 5.0 | 35 | 4780 |
| ISO-2-20 | 5480 | 7370 | >10000 |
| ISO-2-25 | 0.6 | 0.8 | 5740 |
| ISO-2-25-R | 10 | 21 | 2140 |
| ISO-2-25-S | 1360 | 7720 | |
| ISO-2-26 | >10000 | >10000 | >10000 |
| ISO-2-27 | 25 | 127 | >10000 |
| ISO-2-28 | 149 | 5550 | >10000 |
| ISO-2-29 | 14 | 61 | |
| ISO-2-30 | 1 | 8 | |
| ISO-2-30-R | 6 | 14 | 2210 |
| ISO-2-30-S | 839 | 1180 | |
| ISO-2-31 | 5 | 27 | |
| ISO-2-32 | 3150 | 7500 | |
| ISO-2-36 | 0.5 | 8 | |
| ISO-2-38 | 0.5 | 4 | |

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

Incorporation by Reference

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

Equivalents

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having the structural formula of (I):

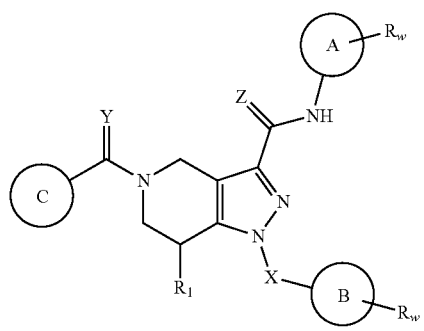

(I)

wherein,
Ring A is a 6-membered aryl ring, Ring B is a 6-membered aryl ring or is a bicyclic aryl group, and Ring C is a 5-membered heteroaryl ring;
$R_W$ of Ring B is a hydrogen, a halide, OH, $NH_2$, alkyl, alkyl amine, alkyl amide, or alkoxy, and $R_W$ of Ring A is an Electrophilic Group $R_E$ Selected from:

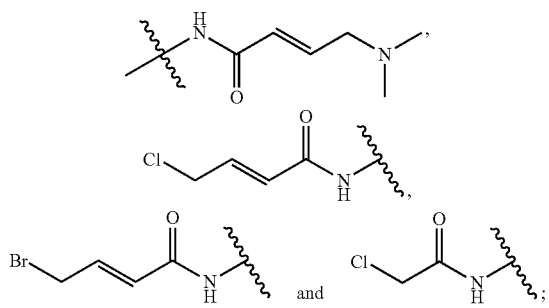

$R_1$ is H, halide, alkyl amine, methoxy, hydroxy or a $C_1$-$C_3$ alkyl group;
X is $CH_2$, NH, O, S or a single bond;
Y is $CH_2$, NH, O or S; and
Z is $CH_2$, NH, O or S, or a pharmaceutically acceptable form thereof.

2. The compound of claim 1, having the structure of:

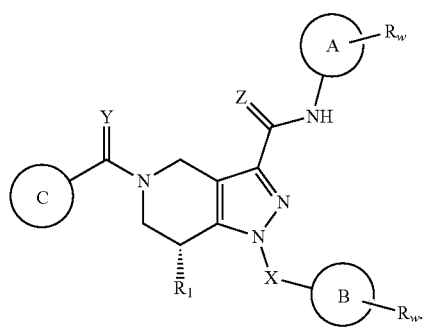

(II)

3. The compound of claim 1, wherein Ring C is pyrrolyl, X is $CH_2$, and each of Y and Z is O.

4. The compound of claim 3, having the structural formula of:

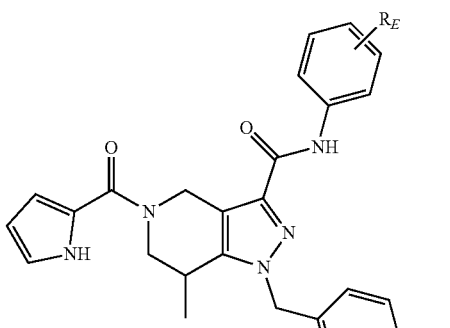

5. The compound of claim 4, having the structural formula of:

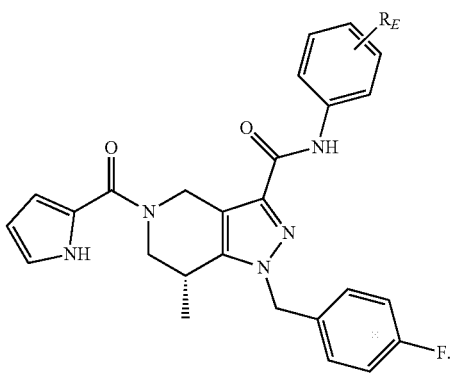

6. A pharmaceutical composition comprising a compound of claim 1 and a pharmaceutically acceptable excipient, carrier, or diluent.

7. A unit dosage form comprising a pharmaceutical composition according to claim 6.

* * * * *